US006333303B1

(12) United States Patent
Borgford

(10) Patent No.: US 6,333,303 B1
(45) Date of Patent: Dec. 25, 2001

(54) ANTIVIRAL RICIN-LIKE PROTEINS

(75) Inventor: Thor Borgford, Burnaby (CA)

(73) Assignee: Twinstrand Therapeutics Inc., Vancouver (CA)

( * ) Notice: Subject to any disclaimer, the term of this patent is extended or adjusted under 35 U.S.C. 154(b) by 0 days.

(21) Appl. No.: 09/147,208

(22) PCT Filed: Apr. 29, 1997

(86) PCT No.: PCT/CA97/00288

§ 371 Date: Mar. 2, 1999

§ 102(e) Date: Mar. 2, 1999

(87) PCT Pub. No.: WO97/41233

PCT Pub. Date: Nov. 6, 1997

Related U.S. Application Data
(60) Provisional application No. 60/016,509, filed on Apr. 30, 1996.

(51) Int. Cl.[7] .................................................. A61N 37/18
(52) U.S. Cl. ........................ 514/2; 536/23.2; 536/23.4; 536/23.6; 530/350; 530/370; 435/320.1; 424/94.1
(58) Field of Search ............................. 435/320.1; 514/2; 424/94.1; 530/350, 370; 536/23.2, 23.4, 23.6

(56) References Cited

U.S. PATENT DOCUMENTS

| | | | |
|---|---|---|---|
| 5,128,460 | 7/1992 | Pirtak, Jr. et al. | 536/27 |
| 5,235,039 | 8/1993 | Heath, Jr. et al. | 530/328 |
| 5,668,255 | * 9/1997 | Murphy | 530/350 |
| 5,677,274 | * 10/1997 | Leppla et al. | 514/2 |

FOREIGN PATENT DOCUMENTS

| | | |
|---|---|---|
| 145111 | 6/1985 | (EP) . |
| PCT/US88/01849 | 12/1988 | (WO) . |
| WO 89/01037 | 2/1989 | (WO) . |
| WO 90/10457 | 9/1990 | (WO) . |

OTHER PUBLICATIONS

Chrigwin et al., *Biochemistry,* 18, 5294–5299 (1979).
Cook, J.P. et al., *Bioconjucate Chemistry,* vol. 4, No. 6, pp. 440–447 (1993).
Endo, Y. & Tsurugi, K.J. *Bio. Chem.* 262:8128 (1987).
Ferrini et al., *Eur. J. Biochem.* 233:772–777 (1995).
Glück, A. and Wool, I.G., *J. Mol. Biol.* 256:838–848 (1996).
Halling et al., *Nucleic Acids Research,* 13:8019–8033 (1985).
Lamb et al., *Eur. J. Biochem.* 148:265–270 (1985).
Leppla S. et al., Zentralblatt Für Bakteriologie, vol. 24, pp. 431–442 (1994).
Lord, J.M. *Eur. J. Biochem.* 146:403–409 (1985).
Lord, J.M. *Eur. J. Biochem.* 146:411–416 (1985).
Lord, J.M. et al., *FASAB Journal* 8:201–208 (1984).
Murakami, S. et al., *Mol. Cel. Biol.* 2:588–592 (1982).
Olsnes, S & Phil, A., in *Molecular action of toxins and viruses* (eds. Cohen, P. & van Heyninger, S.); 51–105 (Elsevier Biomedical Press, Amsterdam, 1982.
Olson et al., *AIDS Res. and Human Retroviruses* 7:1025–1030 (1991).
O'Hare M. et al. *FEBS Lett.* 273:200–204 (1990).
Pastan et al., *Annals New York Academy of Sciences* 758:345–353 (1995).
Richardson, P.T. et al. *FEBS Lett.* 255:15–20 (1989).
Rutenber, E., et al. *Proteins* 10:240–250 (1991).
Saelinger, C.B. in *Trafficking of Bacterial Toxins* (eds. Saelinger, C.B.) 1–13 (CRC Press Inc., Boca Raton, Florida, 1990.
Simmons et al. *Biol. Chem.* 261:7912 (1986).
Sinkar et al., *J. Biosci* (Bangalore) 11:47–58 (1987).
Skalka et al., *Cell,* 56:911–913 (1989).
Spooner et al., *Mol. Immunol.* 31:117–125 (1994).
Vitetta et al., *Science* 238:1098–1104 (1987).
Vitteta et al., *Immunology Today* 14:252–259 (1993).
Vitetta & Thorpe *Seminars in Cell Biology* 2:47–58 (1991).
Westby et al. Bioconjugate Chm. 3:375–381 (1992).
Weston et al., *Mol. Bio.* 244:410–422 (1994).

* cited by examiner

Primary Examiner—Jeffrey Stucker
(74) *Attorney, Agent, or Firm*—Micheline Gravelle; Bereskin & Parr

(57) ABSTRACT

The present invention provides a protein having an A chain of a ricin-like toxin, a B chain of a ricin-like toxin and a heterologous linker amino acid sequence, linking the A and B chains. The linker sequence contains a cleavage recognition site for a retroviral protease. The invention also relates to a nucleic acid molecule encoding the protein and to expression vectors incorporating the nucleic acid molecule. Also provided is a method of inhibiting or destroying mammalian cells infected with a retrovirus utilizing the proteins of the invention and pharmaceutical compositions for treating HIV infection.

28 Claims, 47 Drawing Sheets

WT preproricin linker

```
                        primer HIVA1
                   5'- TATCCAATAGTGCAAAATTTTAATGCTGAT -3'
                          *  *  *              *
         TCTTTGCTTATA

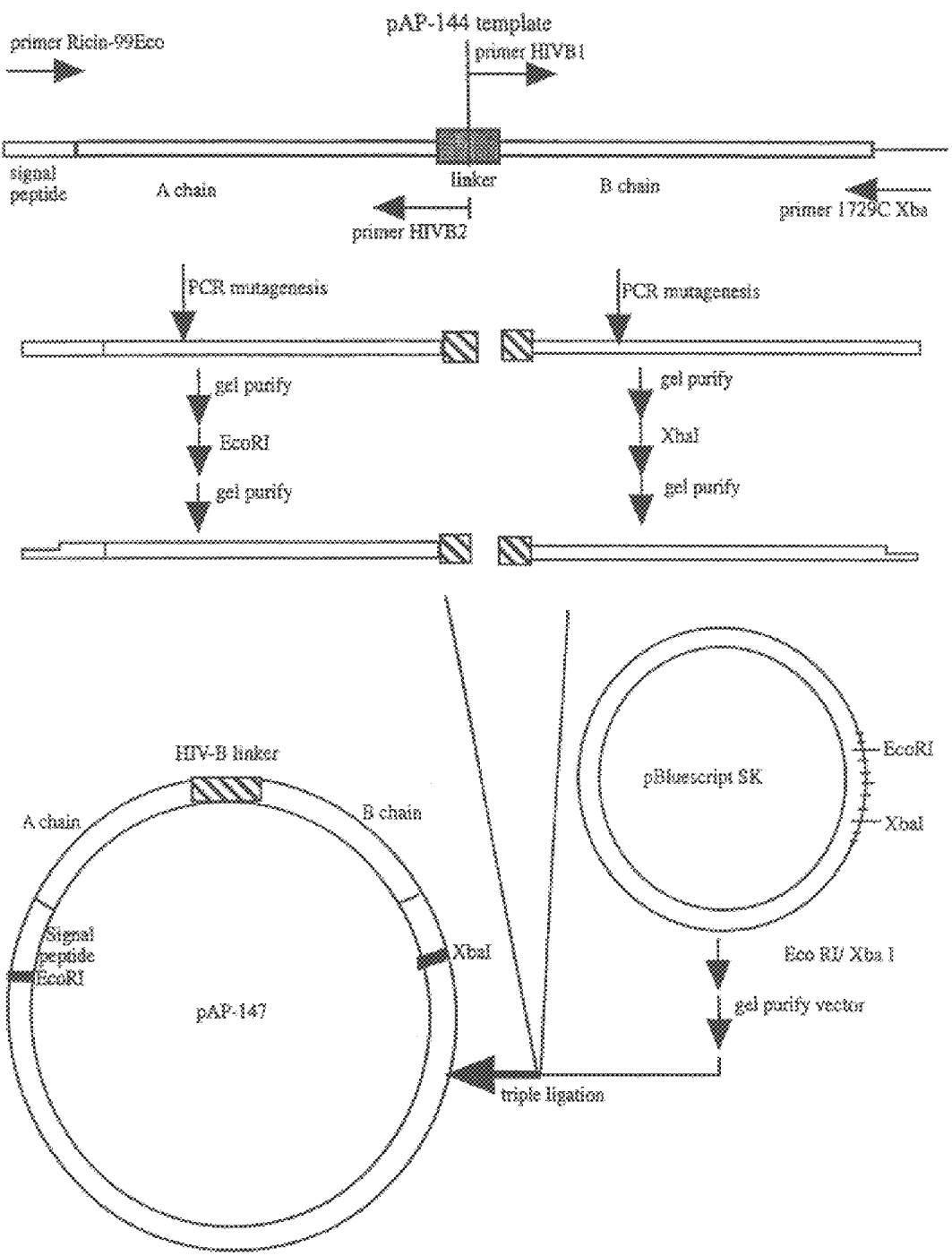

FIGURE 2B

WT preproricin linker primer HIVB1

5'- GCGGAGGCAATGT

FIGURE 3A

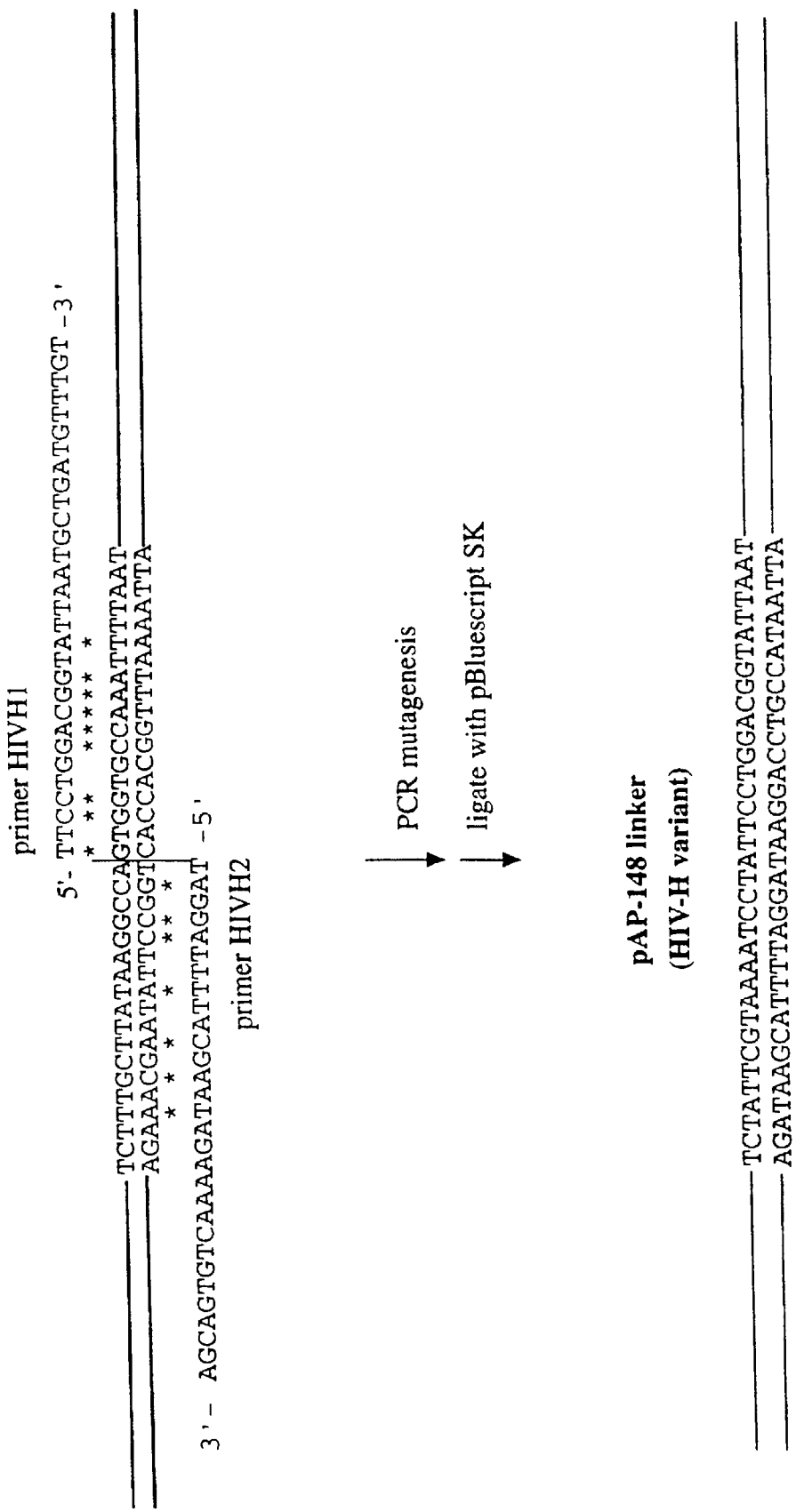

FIGURE 4

Wild type Ricin linker:  A chain- S L L I R P V V P N F N -B chain pAP-146 linker:  A chain- V S Q N Y P I V Q N F N -B chain pAP-147 linker:  A chain- S K A R V L A E A M S N -B chain pAP-148 linker:  A chain- S I R K I L F L D G I N -B chain pAP-146= Ricin cDNA mutant with HIV-A protease linker sequence
pAP-147= Ricin cDNA mutant with HIV-B protease linker sequence
pAP-148= Ricin cDNA mutant with HIV-H protease linker sequence

FIGURE 8

```
              10          20          30          40          50
               |           |           |           |           |
  1  GAATTCCCCTCGAGACGCGTCGACCCGGAGATGAAACCGGGAGGAAATAC
     CTTAAGGGGAGCTCTGCGCAGCTGGGCCTCTACTTTGGCCCTCCTTTATG

51  TATTGTAATATGGATGTATGCAGTGGCAACATGGCTTTGTTTTGGATCCA
     ATAACATTATACCTACATACGTCACCGTTGTACCGAAACAAAACCTAGGT

101  CCTCAGGGTGGTCTTTCACATTAGAGGATAACAACATATTCCCCAAACAA
     GGAGTCCCACCAGAAAGTGTAATCTCCTATTGTTGTATAAGGGGTTTGTT

151  TACCCAATTATAAACTTTACCACAGCGGGTGCCACTGTGCAAAGCTACAC
     ATGGGTTAATATTTGAAATGGTGTCGCCCACGGTGACACGTTTCGATGTG

201  AAACTTTATCAGAGCTGTTCGCGGTCGTTTAACAACTGGAGCTGATGTGA
     TTTGAAATAGTCTCGACAAGCGCCAGCAAATTGTTGACCTCGACTACACT

251  GACATGATATACCAGTGTTGCCAAACAGAGTTGGTTTGCCTATAAACCAA
     CTGTACTATATGGTCACAACGGTTTGTCTCAACCAAACGGATATTTGGTT

301  CGGTTTATTTTAGTTGAACTCTCAAATCATGCAGAGCTTTCTGTTACATT
     GCCAAATAAAATCAACTTGAGAGTTTAGTACGTCTCGAAAGACAATGTAA

351  AGCGCTGGATGTCACCAATGCATATGTGGTCGGCTACCGTGCTGGAAATA
     TCGCGACCTACAGTGGTTACGTATACACCAGCCGATGGCACGACCTTTAT

401  GCGCATATTTCTTTCATCCTGACAATCAGGAAGATGCAGAAGCAATCACT
     CGCGTATAAAGAAAGTAGGACTGTTAGTCCTTCTACGTCTTCGTTAGTGA

451  CATCTTTTCACTGATGTTCAAAATCGATATACATTCGCCTTTGGTGGTAA
     GTAGAAAAGTGACTACAAGTTTTAGCTATATGTAAGCGGAAACCACCATT

501  TTATGATAGACTTGAACAACTTGCTGGTAATCTGAGAGAAAATATCGAGT
     AATACTATCTGAACTTGTTGAACGACCATTAGACTCTCTTTTATAGCTCA

551  TGGGAAATGGTCCACTAGAGGAGGCTATCTCAGCGCTTTATTATTACAGT
     ACCCTTTACCAGGTGATCTCCTCCGATAGAGTCGCGAAATAATAATGTCA

601  ACTGGTGGCACTCAGCTTCCAACTCTGGCTCGTTCCTTTATAATTTGCAT
     TGACCACCGTGAGTCGAAGGTTGAGACCGAGCAAGGAAATATTAAACGTA

651  CCAAATGATTTCAGAAGCAGCAAGATTCCAATATATTGAGGGAGAAATGC
     GGTTTACTAAAGTCTTCGTCGTTCTAAGGTTATATAACTCCCTCTTTACG

701  GCACGAGAATTAGGTACAACCGGAGATCTGCACCAGATCCTAGCGTAATT
     CGTGCTCTTAATCCATGTTGGCCTCTAGACGTGGTCTAGGATCGCATTAA

751  ACACTTGAGAATAGTTGGGGGAGACTTTCCACTGCAATTCAAGAGTCTAA
     TGTGAACTCTTATCAACCCCCTCTGAAAGGTGACGTTAAGTTCTCAGATT

801  CCAAGGAGCCTTTGCTAGTCCAATTCAACTGCAAAGACGTAATGGTTCCA
     GGTTCCTCGGAAACGATCAGGTTAAGTTGACGTTTCTGCATTACCAAGGT

851  AATTCAGTGTGTACGATGTGAGTATATTAATCCCTATCATAGCTCTCATG
     TTAAGTCACACATGCTACACTCATATAATTAGGGATAGTATCGAGAGTAC

901  GTGTATAGATGCGCACCTCCACCATCGTCACAGTTTGTTTCGCAGAACTA
     CACATATCTACGCGTGGAGGTGGTAGCAGTGTCAAACAAAGCGTCTTGAT
```

FIGURE 8 (Cont'd)

```
 951 TCCAATAGTGCAAAATTTTAATGCTGATGTTTGTATGGATCCTGAGCCCA
     AGGTTATCACGTTTTAAAATTACGACTACAAACATACCTAGGACTCGGGT

1001 TAGTGCGTATCGTAGGTCGAAATGGTCTATGTGTTGATGTTAGGGATGGA
     ATCACGCATAGCATCCAGCTTTACCAGATACACAACTACAATCCCTACCT

1051 AGATTCCACAACGGAAACGCAATACAGTTGTGGCCATGCAAGTCTAATAC
     TCTAAGGTGTTGCCTTTGCGTTATGTCAACACCGGTACGTTCAGATTATG

1101 AGATGCAAATCAGCTCTGGACTTTGAAAAGAGACAATACTATTCGATCTA
     TCTACGTTTAGTCGAGACCTGAAACTTTTCTCTGTTATGATAAGCTAGAT

1151 ATGGAAAGTGTTTAACTACTTACGGGTACAGTCCGGGAGTCTATGTGATG
     TACCTTTCACAAATTGATGAATGCCCATGTCAGGCCCTCAGATACACTAC

1201 ATCTATGATTGCAATACTGCTGCAACTGATGCCACCCGCTGGCAAATATG
     TAGATACTAACGTTATGACGACGTTGACTACGGTGGGCGACCGTTTATAC

1251 GGATAATGGAACCATCATAAATCCCAGATCTAGTCTAGTTTTAGCAGCGA
     CCTATTACCTTGGTAGTATTTAGGGTCTAGATCAGATCAAAATCGTCGCT

1301 CATCAGGGAACAGTGGTACCACACTTACAGTGCAAACCAACATTTATGCC
     GTAGTCCCTTGTCACCATGGTGTGAATGTCACGTTTGGTTGTAAATACGG

1351 GTTAGTCAAGGTTGGCTTCCTACTAATAATACACAACCTTTTGTTACAAC
     CAATCAGTTCCAACCGAAGGATGATTATTATGTGTTGGAAAACAATGTTG

1401 CATTGTTGGGCTATATGGTCTGTGCTTGCAAGCAAATAGTGGACAAGTAT
     GTAACAACCCGATATACCAGACACGAACGTTCGTTTATCACCTGTTCATA

1451 GGATAGAGGACTGTAGCAGTGAAAAGGCTGAACAACAGTGGGCTCTTTAT
     CCTATCTCCTGACATCGTCACTTTTCCGACTTGTTGTCACCCGAGAAATA

1501 GCAGATGGTTCAATACGTCCTCAGCAAAACCGAGATAATTGCCTTACAAG
     CGTCTACCAAGTTATGCAGGAGTCGTTTTGGCTCTATTAACGGAATGTTC

1551 TGATTCTAATATACGGGAAACAGTTGTTAAGATCCTCTCTTGTGGCCCTG
     ACTAAGATTATATGCCCTTTGTCAACAATTCTAGGAGAGAACACCGGGAC

1601 CATCCTCTGGCCAACGATGGATGTTCAAGAATGATGGAACCATTTTAAAT
     GTAGGAGACCGGTTGCTACCTACAAGTTCTTACTACCTTGGTAAAATTTA

1651 TTGTATAGTGGATTGGTGTTAGATGTGAGGCGATCGGATCCGAGCCTTAA
     AACATATCACCTAACCACAATCTACACTCCGCTAGCCTAGGCTCGGAATT

1701 ACAAATCATTCTTTACCCTCTCCATGGTGACCCAAACCAAATATGGTTAC
     TGTTTAGTAAGAAATGGGAGAGGTACCACTGGGTTTGGTTTATACCAATG

1751 CATTATTTTGATAGACAGATTACTCTCTTGCAGTGTGTGTGTCCTGCCAT
     GTAATAAAACTATCTGTCTAATGAGAGAACGTCACACACACAGGACGGTA

1801 GAAAATAGATGGCTTAAATAAAAAGGACATTGTAAATTTTGTAACTGAAA
     CTTTTATCTACCGAATTTATTTTTCCTGTAACATTTAAAACATTGACTTT

1851 GGACAGCAAGTTATATCGAATTCCTGCAG
     CCTGTCGTTCAATATAGCTTAAGGACGTC
```

FIGURE 9

```
            10         20         30         40         50
             |          |          |          |          |
  1 GAATTCCCCTCGAGACGCGTCGACCCGGAGATGAAACCGGGAGGAAATAC
    CTTAAGGGGAGCTCTGCGCAGCTGGGCCTCTACTTTGGCCCTCCTTTATG

51 TATTGTAATATGGATGTATGCAGTGGCAACATGGCTTTGTTTTGGATCCA
    ATAACATTATACCTACATACGTCACCGTTGTACCGAAACAAAACCTAGGT

101 CCTCAGGGTGGTCTTTCACATTAGAGGATAACAACATATTCCCCAAACAA
    GGAGTCCCACCAGAAAGTGTAATCTCCTATTGTTGTATAAGGGGTTTGTT

151 TACCCAATTATAAACTTTACCACAGCGGGTGCCACTGTGCAAAGCTACAC
    ATGGGTTAATATTTGAAATGGTGTCGCCCACGGTGACACGTTTCGATGTG

201 AAACTTTATCAGAGCTGTTCGCGGTCGTTTAACAACTGGAGCTGATGTGA
    TTTGAAATAGTCTCGACAAGCGCCAGCAAATTGTTGACCTCGACTACACT

251 GACATGATATACCAGTGTTGCCAAACAGAGTTGGTTTGCCTATAAACCAA
    CTGTACTATATGGTCACAACGGTTTGTCTCAACCAAACGGATATTTGGTT

301 CGGTTTATTTTAGTTGAACTCTCAAATCATGCAGAGCTTTCTGTTACATT
    GCCAAATAAAATCAACTTGAGAGTTTAGTACGTCTCGAAAGACAATGTAA

351 AGCGCTGGATGTCACCAATGCATATGTGGTCGGCTACCGTGCTGGAAATA
    TCGCGACCTACAGTGGTTACGTATACACCAGCCGATGGCACGACCTTTAT

401 GCGCATATTTCTTTCATCCTGACAATCAGGAAGATGCAGAAGCAATCACT
    CGCGTATAAAGAAAGTAGGACTGTTAGTCCTTCTACGTCTTCGTTAGTGA

451 CATCTTTTCACTGATGTTCAAAATCGATATACATTCGCCTTTGGTGGTAA
    GTAGAAAAGTGACTACAAGTTTTAGCTATATGTAAGCGGAAACCACCATT

501 TTATGATAGACTTGAACAACTTGCTGGTAATCTGAGAGAAAATATCGAGT
    AATACTATCTGAACTTGTTGAACGACCATTAGACTCTCTTTTATAGCTCA

551 TGGGAAATGGTCCACTAGAGGAGGCTATCTCAGCGCTTTATTATTACAGT
    ACCCTTTACCAGGTGATCTCCTCCGATAGAGTCGCGAAATAATAATGTCA

601 ACTGGTGGCACTCAGCTTCCAACTCTGGCTCGTTCCTTTATAATTTGCAT
    TGACCACCGTGAGTCGAAGGTTGAGACCGAGCAAGGAAATATTAAACGTA

651 CCAAATGATTTCAGAAGCAGCAAGATTCCAATATATTGAGGGAGAAATGC
    GGTTTACTAAAGTCTTCGTCGTTCTAAGGTTATATAACTCCCTCTTTACG

701 GCACGAGAATTAGGTACAACCGGAGATCTGCACCAGATCCTAGCGTAATT
    CGTGCTCTTAATCCATGTTGGCCTCTAGACGTGGTCTAGGATCGCATTAA

751 ACACTTGAGAATAGTTGGGGGAGACTTTCCACTGCAATTCAAGAGTCTAA
    TGTGAACTCTTATCAACCCCCTCTGAAAGGTGACGTTAAGTTCTCAGATT

801 CCAAGGAGCCTTTGCTAGTCCAATTCAACTGCAAAGACGTAATGGTTCCA
    GGTTCCTCGGAAACGATCAGGTTAAGTTGACGTTTCTGCATTACCAAGGT

851 AATTCAGTGTGTACGATGTGAGTATATTAATCCCTATCATAGCTCTCATG
    TTAAGTCACACATGCTACACTCATATAATTAGGGATAGTATCGAGAGTAC

901 GTGTATAGATGCGCACCTCCACCATCGTCACAGTTTTCTAAGGCTCGAGT
    CACATATCTACGCGTGGAGGTGGTAGCAGTGTCAAAAGATTCCGAGCTCA

951 GCTAGCGGAGGCAATGTCTAATGCTGATGTTTGTATGGATCCTGAGCCCA
```

FIGURE 9 (Cont'd)

```
       CGATCGCCTCCGTTACAGATTACGACTACAAACATACCTAGGACTCGGGT

1001   TAGTGCGTATCGTAGGTCGAAATGGTCTATGTGTTGATGTTAGGGATGGA
       ATCACGCATAGCATCCAGCTTTACCAGATACACAACTACAATCCCTACCT

1051   AGATTCCACAACGGAAACGCAATACAGTTGTGGCCATGCAAGTCTAATAC
       TCTAAGGTGTTGCCTTTGCGTTATGTCAACACCGGTACGTTCAGATTATG

1101   AGATGCAAATCAGCTCTGGACTTTGAAAAGAGACAATACTATTCGATCTA
       TCTACGTTTAGTCGAGACCTGAAACTTTTCTCTGTTATGATAAGCTAGAT

1151   ATGGAAAGTGTTTAACTACTTACGGGTACAGTCCGGGAGTCTATGTGATG
       TACCTTTCACAAATTGATGAATGCCCATGTCAGGCCCTCAGATACACTAC

1201   ATCTATGATTGCAATACTGCTGCAACTGATGCCACCCGCTGGCAAATATG
       TAGATACTAACGTTATGACGACGTTGACTACGGTGGGCGACCGTTTATAC

1251   GGATAATGGAACCATCATAAATCCCAGATCTAGTCTAGTTTTAGCAGCGA
       CCTATTACCTTGGTAGTATTTAGGGTCTAGATCAGATCAAAATCGTCGCT

1301   CATCAGGGAACAGTGGTACCACACTTACAGTGCAAACCAACATTTATGCC
       GTAGTCCCTTGTCACCATGGTGTGAATGTCACGTTTGGTTGTAAATACGG

1351   GTTAGTCAAGGTTGGCTTCCTACTAATAATACACAACCTTTTGTTACAAC
       CAATCAGTTCCAACCGAAGGATGATTATTATGTGTTGGAAAACAATGTTG

1401   CATTGTTGGGCTATATGGTCTGTGCTTGCAAGCAAATAGTGGACAAGTAT
       GTAACAACCCGATATACCAGACACGAACGTTCGTTTATCACCTGTTCATA

1451   GGATAGAGGACTGTAGCAGTGAAAAGGCTGAACAACAGTGGGCTCTTTAT
       CCTATCTCCTGACATCGTCACTTTTCCGACTTGTTGTCACCCGAGAAATA

1501   GCAGATGGTTCAATACGTCCTCAGCAAAACCGAGATAATTGCCTTACAAG
       CGTCTACCAAGTTATGCAGGAGTCGTTTTGGCTCTATTAACGGAATGTTC

1551   TGATTCTAATATACGGGAAACAGTTGTTAAGATCCTCTCTTGTGGCCCTG
       ACTAAGATTATATGCCCTTTGTCAACAATTCTAGGAGAGAACACCGGGAC

1601   CATCCTCTGGCCAACGATGGATGTTCAAGAATGATGGAACCATTTTAAAT
       GTAGGAGACCGGTTGCTACCTACAAGTTCTTACTACCTTGGTAAAATTTA

1651   TTGTATAGTGGATTGGTGTTAGATGTGAGGCGATCGGATCCGAGCCTTAA
       AACATATCACCTAACCACAATCTACACTCCGCTAGCCTAGGCTCGGAATT

1701   ACAAATCATTCTTTACCCTCTCCATGGTGACCCAAACCAAATATGGTTAC
       TGTTTAGTAAGAAATGGGAGAGGTACCACTGGGTTTGGTTTATACCAATG

1751   CATTATTTTGATAGACAGATTACTCTCTTGCAGTGTGTGTGTCCTGCCAT
       GTAATAAAACTATCTGTCTAATGAGAGAACGTCACACACACAGGACGGTA

1801   GAAAATAGATGGCTTAAATAAAAAGGACATTGTAAATTTTGTAACTGAAA
       CTTTTATCTACCGAATTTATTTTTCCTGTAACATTTAAAACATTGACTTT

1851   GGACAGCAAGTTATATCGAATTCCTGCAG
       CCTGTCGTTCAATATAGCTTAAGGACGTC
```

FIGURE 10

```
                10        20        30        40        50
                 |         |         |         |         |
  1  GAATTCCCCTCGAGACGCGTCGACCCGGAGATGAAACCGGGAGGAAATAC
     CTTAAGGGGAGCTCTGCGCAGCTGGGCCTCTACTTTGGCCCTCCTTTATG

51  TATTGTAATATGGATGTATGCAGTGGCAACATGGCTTTGTTTTGGATCCA
     ATAACATTATACCTACATACGTCACCGTTGTACCGAAACAAAACCTAGGT

101  CCTCAGGGTGGTCTTTCACATTAGAGGATAACAACATATTCCCCAAACAA
     GGAGTCCCACCAGAAAGTGTAATCTCCTATTGTTGTATAAGGGGTTTGTT

151  TACCCAATTATAAACTTTACCACAGCGGGTGCCACTGTGCAAAGCTACAC
     ATGGGTTAATATTTGAAATGGTGTCGCCCACGGTGACACGTTTCGATGTG

201  AAACTTTATCAGAGCTGTTCGCGGTCGTTTAACAACTGGAGCTGATGTGA
     TTTGAAATAGTCTCGACAAGCGCCAGCAAATTGTTGACCTCGACTACACT

251  GACATGATATACCAGTGTTGCCAAACAGAGTTGGTTTGCCTATAAACCAA
     CTGTACTATATGGTCACAACGGTTTGTCTCAACCAAACGGATATTTGGTT

301  CGGTTTATTTTAGTTGAACTCTCAAATCATGCAGAGCTTTCTGTTACATT
     GCCAAATAAAATCAACTTGAGAGTTTAGTACGTCTCGAAAGACAATGTAA

351  AGCGCTGGATGTCACCAATGCATATGTGGTCGGCTACCGTGCTGGAAATA
     TCGCGACCTACAGTGGTTACGTATACACCAGCCGATGGCACGACCTTTAT

401  GCGCATATTTCTTTCATCCTGACAATCAGGAAGATGCAGAAGCAATCACT
     CGCGTATAAAGAAAGTAGGACTGTTAGTCCTTCTACGTCTTCGTTAGTGA

451  CATCTTTTCACTGATGTTCAAAATCGATATACATTCGCCTTTGGTGGTAA
     GTAGAAAAGTGACTACAAGTTTTAGCTATATGTAAGCGGAAACCACCATT

501  TTATGATAGACTTGAACAACTTGCTGGTAATCTGAGAGAAAATATCGAGT
     AATACTATCTGAACTTGTTGAACGACCATTAGACTCTCTTTTATAGCTCA

551  TGGGAAATGGTCCACTAGAGGAGGCTATCTCAGCGCTTTATTATTACAGT
     ACCCTTTACCAGGTGATCTCCTCCGATAGAGTCGCGAAATAATAATGTCA

601  ACTGGTGGCACTCAGCTTCCAACTCTGGCTCGTTCCTTTATAATTTGCAT
     TGACCACCGTGAGTCGAAGGTTGAGACCGAGCAAGGAAATATTAAACGTA

651  CCAAATGATTTCAGAAGCAGCAAGATTCCAATATATTGAGGGAGAAATGC
     GGTTTACTAAAGTCTTCGTCGTTCTAAGGTTATATAACTCCCTCTTTACG

701  GCACGAGAATTAGGTACAACCGGAGATCTGCACCAGATCCTAGCGTAATT
     CGTGCTCTTAATCCATGTTGGCCTCTAGACGTGGTCTAGGATCGCATTAA

751  ACACTTGAGAATAGTTGGGGGAGACTTTCCACTGCAATTCAAGAGTCTAA
     TGTGAACTCTTATCAACCCCCTCTGAAAGGTGACGTTAAGTTCTCAGATT

801  CCAAGGAGCCTTTGCTAGTCCAATTCAACTGCAAAGACGTAATGGTTCCA
     GGTTCCTCGGAAACGATCAGGTTAAGTTGACGTTTCTGCATTACCAAGGT

851  AATTCAGTGTGTACGATGTGAGTATATTAATCCCTATCATAGCTCTCATG
     TTAAGTCACACATGCTACACTCATATAATTAGGGATAGTATCGAGAGTAC

901  GTGTATAGATGCGCACCTCCACCATCGTCACAGTTTTCTATTCGTAAAAT
     CACATATCTACGCGTGGAGGTGGTAGCAGTGTCAAAAGATAAGCATTTTA

951  CCTATTCCTGGACGGTATTAATGCTGATGTTTGTATGGATCCTGAGCCCA
```

FIGURE 10 (Cont'd)

```
     GGATAAGGACCTGCCATAATTACGACTACAAACATACCTAGGACTCGGGT
1001 TAGTGCGTATCGTAGGTCGAAATGGTCTATGTGTTGATGTTAGGGATGGA
     ATCACGCATAGCATCCAGCTTTACCAGATACACAACTACAATCCCTACCT
1051 AGATTCCACAACGGAAACGCAATACAGTTGTGGCCATGCAAGTCTAATAC
     TCTAAGGTGTTGCCTTTGCGTTATGTCAACACCGGTACGTTCAGATTATG
1101 AGATGCAAATCAGCTCTGGACTTTGAAAAGAGACAATACTATTCGATCTA
     TCTACGTTTAGTCGAGACCTGAAACTTTTCTCTGTTATGATAAGCTAGAT
1151 ATGGAAAGTGTTTAACTACTTACGGGTACAGTCCGGGAGTCTATGTGATG
     TACCTTTCACAAATTGATGAATGCCCATGTCAGGCCCTCAGATACACTAC
1201 ATCTATGATTGCAATACTGCTGCAACTGATGCCACCCGCTGGCAAATATG
     TAGATACTAACGTTATGACGACGTTGACTACGGTGGGCGACCGTTTATAC
1251 GGATAATGGAACCATCATAAATCCCAGATCTAGTCTAGTTTTAGCAGCGA
     CCTATTACCTTGGTAGTATTTAGGGTCTAGATCAGATCAAAATCGTCGCT
1301 CATCAGGGAACAGTGGTACCACACTTACAGTGCAAACCAACATTTATGCC
     GTAGTCCCTTGTCACCATGGTGTGAATGTCACGTTTGGTTGTAAATACGG
1351 GTTAGTCAAGGTTGGCTTCCTACTAATAATACACAACCTTTTGTTACAAC
     CAATCAGTTCCAACCGAAGGATGATTATTATGTGTTGGAAAACAATGTTG
1401 CATTGTTGGGCTATATGGTCTGTGCTTGCAAGCAAATAGTGGACAAGTAT
     GTAACAACCCGATATACCAGACACGAACGTTCGTTTATCACCTGTTCATA
1451 GGATAGAGGACTGTAGCAGTGAAAAGGCTGAACAACAGTGGGCTCTTTAT
     CCTATCTCCTGACATCGTCACTTTTCCGACTTGTTGTCACCCGAGAAATA
1501 GCAGATGGTTCAATACGTCCTCAGCAAAACCGAGATAATTGCCTTACAAG
     CGTCTACCAAGTTATGCAGGAGTCGTTTTGGCTCTATTAACGGAATGTTC
1551 TGATTCTAATATACGGGAAACAGTTGTTAAGATCCTCTCTTGTGGCCCTG
     ACTAAGATTATATGCCCTTTGTCAACAATTCTAGGAGAGAACACCGGGAC
1601 CATCCTCTGGCCAACGATGGATGTTCAAGAATGATGGAACCATTTTAAAT
     GTAGGAGACCGGTTGCTACCTACAAGTTCTTACTACCTTGGTAAAATTTA
1651 TTGTATAGTGGATTGGTGTTAGATGTGAGGCGATCGGATCCGAGCCTTAA
     AACATATCACCTAACCACAATCTACACTCCGCTAGCCTAGGCTCGGAATT
1701 ACAAATCATTCTTTACCCTCTCCATGGTGACCCAAACCAAATATGGTTAC
     TGTTTAGTAAGAAATGGGAGAGGTACCACTGGGTTTGGTTTATACCAATG
1751 CATTATTTTGATAGACAGATTACTCTCTTGCAGTGTGTGTGTCCTGCCAT
     GTAATAAAACTATCTGTCTAATGAGAGAACGTCACACACACAGGACGGTA
1801 GAAAATAGATGGCTTAAATAAAAAGGACATTGTAAATTTTGTAACTGAAA
     CTTTTATCTACCGAATTTATTTTTCCTGTAACATTTAAAACATTGACTTT
1851 GGACAGCAAGTTATATCGAATTCCTGCAG
     CCTGTCGTTCAATATAGCTTAAGGACGTC
```

FIGURE 11

```
ID    PVL1393    preliminary; circular DNA; SYN;
9632 BP.
XX
AC    IG1137;
XX
DT    01-FEB-1993 (Rel. 7, Created)
DT    01-JUL-1995 (Rel. 12, Last updated, Version 1)
XX
DE    E. coli plasmid vector pVL1393 - complete.
XX
KW    cloning vector.
XX
OS    Cloning vector
OC    Artificial sequences; Cloning vehicles.
XX
RN    [1]
RC    p2Bac from baculovirus
RC    p2Blue from p2Bac
RC    pBlueBac from AcNPV
RC    pBlueBac2 from AcNPV
RC    pBlueBacIII from AcNPV
RC    pBlueBacHisA from AcNPV
RC    pBlueBacHisB from AcNPV
RC    pBlueBacHisC from AcNPV
RC    pVL1392, pVL1393 from pAc360
RA    ;
RT    ;
RL    The Digest 5:2-2(1992).
XX
CC    NM (pVL1393)
CC    CM (yes)
CC    NA (ds-DNA)
CC    TP (circular)
CC    ST ()
CC    TY (plasmid)
CC    SP (British Biotechnology)(Invitrogen)
CC    HO (E.coli NM522)(E.coli INValphaF')(insect)
CC    CP ()
CC    FN (expression)(transfer)
CC    SE ()
CC    PA (pAC360)
CC    BR (pVL1392)
CC    OF ()
CC    OR ()
XX
FH    Key           Location/Qualifiers
FH
```

FIGURE 11 (Cont'd)

```
FT   misc_feature         0..0
FT                        /note="1. pAc360, ori/amp/AcMNPV
polyhedrin gene
FT                        -> pVL1393 9632bp"
FT   transposon           0..0
FT                        /note="TRN AcMNPV"
FT   misc_binding         868..868
FT                        /note="SIT SacII"
FT   misc_binding         1395..1395
FT                        /note="SIT ApaI"
FT   misc_binding         1901..1901
FT                        /note="SIT XhoI"
FT   promoter             0..0
FT                        /note="PRO AcMNPV polyhedrin gene"
FT   misc_binding         0..0
FT                        /note="MCS
FT                        BamHI-SmaI-XbaI-EcoRI-NotI-XmaIII-PstI-
BglII"
FT   rep_origin           0..0
FT                        /note="ORI E. coli pMB1 (ColE1 and
pBR322)"
FT   CDS                  complement(0..0)
FT                        /note="ANT E. coli beta-lactamase gene
(bla)
FT                        ampicillin resistance gene (apr/amp)"
XX
SQ   Sequence 9632 BP; 2602 A; 2122 C; 2176 G; 2732 T; 0
other;
        aagctttact cgtaaagcga gttgaaggat catatttagt tgcgtttatg
        agataagatt gaaagcacgt gtaaatgtt tcccgcgcgt tggcacaact
        atttacaatg cggccaagtt ataaagatt ctaatctgat atgttttaaa
        acacctttgc ggcccgagtt gtttgcgtac gtgactagcg aagaagatgt
        gtggaccgca gaacagatag taaaacaaaa ccctagtatt ggagcaataa
        tcgatttaac caacacgtct aaatattatg atggtgtgca ttttttgcgg
        gcgggcctgt tatacaaaaa aattcaagta cctggccaga cttttgccgcc
        tgaaagcata gttcaagaat ttattgacac ggtaaaagaa tttacagaaa
        agtgtcccgg catgttggtg ggcgtgcact gcacacacgg tattaatcgc
        accggttaca tggtgtgcag atatttaatg cacaccctgg gtattgcgcc
        gcaggaagcc atagatagat tcgaaaaagc cagaggtcac aaaattgaaa
        gacaaaatta cgttcaagat ttattaattt aattaatatt atttgcattc
        tttaacaaat actttatcct attttcaaat tgttgcgctt cttccagcga
        accaaaacta tgcttcgctt gctccgttta gcttgtagcc gatcagtggc
        gttgttccaa tcgacggtag gattaggccg gatattctcc accacaatgt
        tggcaacgtt gatgttacgt ttatgctttt ggttttccac gtacgtcttt
        tggccggtaa tagccgtaaa cgtagtgccg tcgcgcgtca cgcacaacac
        cggatgtttg cgcttgtccg cggggtattg aaccgcgcga tccgacaaat
        ccaccacttt ggcaactaaa tcggtgacct gcgcgtcttt tttctgcatt
        atttcgtctt tcttttgcat ggtttcctgg aagccggtgt acatgcggtt
        tagatcagtc atgacgcgcg tgacctgcaa atctttggcc tcgatctgct
        tgtccttgat ggcaacgatg cgttcaataa actcttgttt tttaacaagt
        tcctcggttt tttgcgccac caccgcttgc agcgcgtttg tgtgctcggt
        gaatgtcgca atcagcttag tcaccaactg tttgctctcc tcctcccgtt
        gtttgatcgc gggatcgtac ttgccggtgc agagcacttg aggaattact
        tcttctaaaa gccattcttg taattctatg gcgtaaggca atttggactt
```

FIGURE 11 (Cont'd)

```
cataatcagc tgaatcacgc cggatttagt aatgagcact gtatgcggct
gcaaatacag cgggtcgccc cttttcacga cgctgttaga ggtagggccc
ccattttgga tggtctgctc aaataacgat ttgtatttat tgtctacatg
aacacgtata gctttatcac aaactgtata ttttaaactg ttagcgacgt
ccttggccac gaaccggacc tgttggtcgc gctctagcac gtaccgcagg
ttgaacgtat cttctccaaa tttaaattct ccaattttaa cgcgagccat
tttgatacac gtgtgtcgat tttgcaacaa ctattgtttt ttaacgcaaa
ctaaacttat tgtggtaagc aataattaaa tatgggggaa catgcgccgc
tacaacactc gtcgttatga acgcagacgg cgccggtctc ggcgcaagcg
gctaaaacgt gttgcgcgtt caacgcggca aacatcgcaa aagccaatag
tacagttttg atttgcatat taacggcgat tttttaaatt atcttattta
ataaatagtt atgacgccta caactcccg cccgcgttga ctcgctgcac
ctcgagcagt tcgttgacgc cttcctccgt gtggccgaac acgtcgagcg
ggtggtcgat gaccagcggc gtgccgcacg cgacgcacaa gtatctgtac
accgaatgat cgtcgggcga aggcacgtcg gcctccaagt ggcaatattg
gcaaattcga aaatatatac agttgggttg tttgcgcata tctatcgtgg
cgttgggcat gtacgtccga acgttgattt gcatgcaagc cgaaattaaa
tcattgcgat tagtgcgatt aaaacgttgt acatcctcgc ttttaatcat
gccgtcgatt aaatcgcgca atcgagtcaa gtgatcaaag tgtggaataa
tgttttcttt gtattcccga gtcaagcgca gcgcgtattt taacaaacta
gccatcttgt aagttagttt catttaatgc aactttatcc aataatatat
tatgtatcgc acgtcaagaa ttaacaatgc gcccgttgtc gcatctcaac
acgactatga tagagatcaa ataaagcgcg aattaaatag cttgcgacgc
aacgtgcacg atctgtgcac gcgttccggc acgagctttg attgtaataa
gttttacga agcgatgaca tgaccccgt agtgacaacg atcacgccca
aaagaactgc cgactacaaa attaccgagt atgtcggtga cgttaaaact
attaagccat ccaatcgacc gttagtcgaa tcaggaccgc tggtgcgaga
agccgcgaag tatggcgaat gcatcgtata acgtgtggag tccgctcatt
agagcgtcat gtttagacaa gaaagctaca tatttaattg atcccgatga
ttttattgat aaattgaccc taactccata cacggtattc tacaatggcg
gggttttggt caaaatttcc ggactgcgat tgtacatgct gttaacggct
ccgcccacta ttaatgaaat taaaaattcc aattttaaaa aacgcagcaa
gagaaacatt tgtatgaaag aatgcgtaga aggaaagaaa aatgtcgtcg
acatgctgaa caacaagatt aatatgcctc cgtgtataaa aaaaatattg
aacgatttga aagaaaacaa tgtaccgcgc ggcggtatgt acaggaagag
gtttatacta aactgttaca ttgcaaacgt ggtttcgtgt gccaagtgtg
aaaaccgatg tttaatcaag gctctgacgc atttctacaa ccacgactcc
aagtgtgtgg gtgaagtcat gcatcttta atcaaatccc aagatgtgta
taaaccacca aactgccaaa aaatgaaaac tgtcgacaag ctctgtccgt
ttgctggcaa ctgcaagggt ctcaatccta tttgtaatta ttgaataata
aaacaattat aaatgctaaa tttgtttttt attaacgata caaaccaaac
gcaacaagaa catttgtagt attatctata attgaaaacg cgtagttata
atcgctgagg taatatttaa aatcattttc aaatgattca cagttaattt
gcgacaatat aatttatttt tcacataaac tagacgcctt gtcgtcttct
tcttcgtatt ccttctcttt ttcattttttc tcctcataaa aattaacata
gttattatcg tatccatata tgtatctatc gtatagagta aatttttttgt
tgtcataaat atatatgtct tttttaatgg ggtgtatagt accgctgcgc
atagtttttc tgtaatttac aacagtgcta ttttctggta gttcttcgga
gtgtgttgct ttaattatta aatttatata atcaatgaat ttgggatcgt
cggttttgta caatatgttg ccggcatagt
acgcagcttc ttctagttca attaccacat tttttagcag caccggatta
acataacttt ccaaaatgtt gtacgaaccg ttaaacaaaa acagttcacc
tcccttttct atactattgt ctgcgagcag ttgtttgttg ttaaaaataa
cagccattgt aatgagacgc acaaactaat atcacaaact ggaaatgtct
```

FIGURE 11 (Cont'd)

```
ctgtcccgat ttatttgaaa cactacaaat taaaggcgag cttTcgtacc
aacttgttag caatattatt agacagctgt gtgaagcgct caacgatttg
cacaagcaca atttcataca caacgacata aaactcgaaa atgtcttata
tttcgaagca cttgatcgcg tgtatgtttg cgattacgga ttgtgcaaac
acgaaaactc acttagcgtg cacgacggca cgttggagta ttttagtccg
gaaaaattc  gacacacaac tatgcacgtt tcgtttgact ggtacgcggc
gtgttaacat acaagttgct aacgtaatca tggtcatagc tgtttcctgt
gtgaaattgt tatccgctca caattccaca caacatacga gccggaagca
taaagtgtaa agcctggggt gcctaatgag tgagctaact cacattaatt
gcgttgcgct cactgcccgc tttccagtcg ggaacctgt  cgtgccagct
gcattaatga atcggccaac gcgcggggag aggcggtttg cgtattgggc
gctcttccgc ttcctcgctc actgactcgc tgcgctcggt cgttcggctg
cggcgagcgg tatcagctca ctcaaaggcg gtaatacggt tatccacaga
atcagggat  aacgcaggaa agaacatgtg agcaaaggc  cagcaaaagg
ccaggaaccg taaaaaggcc gcgttgctgg cgttttcca  taggctccgc
ccccctgacg agcatcacaa aaatcgacgc tcaagtcaga ggtggcgaaa
cccgacagga ctataaagat accaggcgtt tccccctgga agctccctcg
tgcgctctcc tgttccgacc ctgccgctta ccggatacct gtccgccttt
ctcccttcgg gaagcgtggc gctttctcat agctcacgct gtaggtatct
cagttcggtg taggtcgttc gctccaagct gggctgtgtg cacgaacccc
ccgttcagcc cgaccgctgc gccttatccg gtaactatcg tcttgagtcc
aacccggtaa
gacacgactt atcgccactg gcagcagcca ctggtaacag gattagcaga
gcgaggtatg taggcggtgc tacagagttc ttgaagtggt ggcctaacta
cggctacact agaaggacag tatttggtat ctgcgctctg ctgaagccag
ttaccttcgg aaaaagagtt ggtagctctt gatccggcaa acaaaccacc
gctggtagcg gtggtttttt tgtttgcaag cagcagatta cgcgcagaaa
aaaaggatct caagaagatc ctttgatctt ttctacgggg tctgacgctc
agtggaacga aaactcacgt taagggattt tggtcatgag attatcaaaa
aggatcttca cctagatcct tttaaattaa aatgaagtt  ttaaatcaat
ctaaagtata tatgagtaaa cttggtctga cagttaccaa tgcttaatca
gtgaggcacc tatctcagcg atctgtctat ttcgttcatc catagttgcc
tgactccccg tcgtgtagat aactacgata cgggagggct taccatctgg
ccccagtgct gcaatgatac cgcgagaccc acgctcaccg gctccagatt
tatcagcaat aaaccagcca gccggaaggg ccgagcgcag aagtggtcct
gcaactttat ccgcctccat ccagtctatt aattgttgcc gggaagctag
agtaagtagt tcgccagtta atagtttgcg caacgttgtt gccattgcta
caggcatcgt ggtgtcacgc tcgtcgtttg gtatggcttc attcagctcc
ggttcccaac gatcaaggcg agttacatga tcccccatgt tgtgcaaaaa
agcggttagc tccttcggtc ctccgatcgt tgtcagaagt aagttggccg
cagtgttatc actcatggtt atggcagcac tgcataattc tcttactgtc
atgccatccg taagatgctt ttctgtgact ggtgagtact caaccaagtc
attctgagaa tagtgtatgc ggcgaccgag ttgctcttgc ccggcgtcaa
tacgggataa taccgcgcca catagcagaa ctttaaaagt gctcatcatt
ggaaaacgtt cttcggggcg aaaactctca aggatcttac cgctgttgag
atccagttcg atgtaaccca ctcgtgcacc caactgatct tcagcatctt
ttactttcac cagcgtttct gggtgagcaa aacaggaag  gcaaaatgcc
gcaaaaaagg gaataagggc gacacggaaa tgttgaatac tcatactctt
cctttttcaa tattattgaa gcatttatca gggttattgt ctcatgagcg
gatacatatt tgaatgtatt tagaaaaata acaaatagg  ggttccgcgc
acatttcccc gaaaagtgcc acctgacgtc taagaaacca ttattatcat
gacattaacc tataaaaata ggcgtatcac gaggcccttt cgtctcgcgc
gtttcggtga tgacggtgaa aacctctgac acatgcagct cccggagacg
gtcacagctt gtctgtaagc ggatgccggg agcagacaag cccgtcaggg
```

FIGURE 11 (Cont'd)

```
atcaatatat agttgctgat atcatggaga taattaaaat gataaccatc
tcgcaaataa ataagtattt tactgttttc gtaacagttt tgtaataaaa
aaacctataa atattccgga ttattcatac cgtcccacca tcgggcgcgg
atcccgggta ccttctagaa ttccggagcg gccgctgcag atctgatcct
ttcctgggac ccggcaagaa ccaaaaactc actctcttca aggaaatccg
taatgttaaa cccgacacga tgaagcttgt cgttggatgg aaaggaaaag
agttctacag ggaaacttgg acccgcttca tggaagacag cttccccatt
gttaacgacc aagaagtgat ggatgttttc cttgttgtca acatgcgtcc
cactagaccc aaccgttgtt acaaattcct ggcccaacac gctctgcgtt
gcgaccccga ctatgtacct catgacgtga ttaggatcgt cgagccttca
tgggtgggca gcaacaacga gtaccgcatc agcctggcta agaagggcgg
cggctgccca ataatgaacc ttcactctga gtacaccaac tcgttcgaac
agttcatcga tcgtgtcatc tgggagaact tctacaagcc catcgtttac
atcggtaccg actctgctga agaggaggaa attctccttg aagtttccct
ggtgttcaaa gtaaaggagt tgcaccaga cgcacctctg ttcactggtc
cggcgtatta aaacacgata cattgttatt agtacattta ttaagcgcta
gattctgtgc gttgttgatt tacagacaat tgttgtacgt attttaataa
ttcattaaat ttataatctt tagggtggta tgttagagcg aaaatcaaat
gattttcagc gtctttatat ctgaatttaa atattaaatc ctcaatagat
ttgtaaaata ggtttcgatt agtttcaaac aagggttgtt tttccgaacc
gatggctgga ctatctaatg gattttcgct caacgccaca aaacttgcca
aatcttgtag cagcaatcta gctttgtcga tattcgtttg tgttttgttt
tgtaataaag gttcgacgtc gttcaaaata ttatgcgctt ttgtatttct
ttcatcactg tcgttagtgt acaattgact cgacgtaaac acgttaaata
aagcttggac atatttaaca tcgggcgtgt tagctttatt aggccgatta
tcgtcgtcgt cccaaccctc gtcgttagaa gttgcttccg aagacgattt
tgccatagcc acacgacgcc tattaattgt gtcggctaac acgtccgcga
tcaaatttgt agttgagctt tttggaatta tttctgattg cgggcgtttt
tgggcgggtt tcaatctaac tgtgcccgat tttaattcag acaacacgtt
agaaagcgat ggtgcaggcg gtggtaacat ttcagacggc aaatctacta
atggcggcgg tggtggagct gatgataaat ctaccatcgg tggaggcgca
ggcggggctg gcggcggagg cggaggcgga ggtggtggcg gtgatgcaga
cggcggttta ggctcaaatg tctctttagg caacacagtc ggcacctcaa
ctattgtact ggtttcgggc gccgttttg gtttgaccgg tctgagacga
gtgcgatttt tttcgtttct aatagcttcc aacaattgtt gtctgtcgtc
taaaggtgca gcgggttgag gttccgtcgg cattggtgga gcgggcggca
attcagacat cgatggtggt ggtggtggtg gaggcgctgg aatgttaggc
acgggagaag gtggtggcgg cggtgccgcc ggtataattt gttctggttt
agtttgttcg cgcacgattg tgggcaccgg cgcaggcgcc gctggctgca
caacggaagg tcgtctgctt cgaggcagcg cttggggtgg tggcaattca
atattataat tggaatacaa atcgtaaaaa tctgctataa gcattgtaat
ttcgctatcg tttaccgtgc cgatatttaa caaccgctca atgtaagcaa
ttgtattgta aagagattgt ctcaagctcg ccgcacgccg ataacaagcc
ttttcatttt tactacagca ttgtagtggc gagacacttc gctgtcgtcg
acgtacatgt atgctttgtt gtcaaaaacg tcgttggcaa gctttaaaat
atttaaaaga acatctctgt tcagcaccac tgtgttgtcg taaatgttgt
ttttgataat ttgcgcttcc gcagtatcga cacgttcaaa aaattgatgc
gcatcaattt tgttgttcct attattgaat aaataagatt gtacagattc
atatctacga ttcgtcatgg ccaccacaaa tgctacgctg caaacgctgg
tacaattttta cgaaaactgc aaaaacgtca aaactcggta taaaataatc
aacgggcgct ttggcaaaat atctatttta tcgcacaagc ccactagcaa
attgtatttg cagaaaacaa tttcggcgca caatttaac gctgacgaaa
taaaagttca ccagttaatg agcgaccacc caaatttat aaaaatctat
tttaatcacg gttccatcaa caaccaagtg atcgtgatgg actacattga
```

FIGURE 11 (Cont'd)

```
cgcgtcagcg ggtgttggcg ggtgtcgggg ctggcttaac tatgcggcat
cagagcagat tgtactgaga gtgcaccata tgcggtgtga ataccgcac
agatgcgtaa ggagaaaata ccgcatcagg cgccattcgc cattcaggct
gcgcaactgt tgggaagggc gatcggtgcg ggcctcttcg ctattacgcc
agctggcgaa aggggatgt gctgcaaggc gattaagttg ggtaacgcca
gggttttccc agtcacgacg ttgtaaaacg acggccagtg cc
```

FIGURE 13

Confirmation of pAP 190 purity by
Western analysis

| Fraction Numbers | 32 | 33 | 34 | A | 35 | 36 | 37 | 38 | 39 |

Purified pAP 190 variant →

Processed Material →

A. Ricin standard

Cleavage of pAP 190 by HIV protease

A. Ricin standard
B. pAP 190
C. pAP 190 + HIV protease (3 hours)
D. pAP 190
E. pAP 190 + HIV protease (30 minutes)
F. pAP 190 + HIV protease (1 hour)
G. pAP 190 + HIV protease (2 hours)

Activation of pAP 190

A. RNA Ladder
B. Ricin A chain
C. Negative control
D. 340 pg pAP 190 variant
E. 2.1 ng pAP 190 variant
F. 12.5 ng pAP 190 variant
G. 75 ng pAP 190 variant
H. 340 pg 190 + HIV protease
I. 2.1 ng 190 + HIV protease
J. 12.5 ng 190 + HIV protease
K. 75 ng 190 + HIV protease

FIGURE 16B

WT preproricin linker

```
                    primer HTLV1-A1
                      5'- CCGGTGATGCATCCTAATGCTGATGTTTGT -3'
                          **    ****   **
        TCTTTGCTTATAAGGCCAGTGGTGCCAAATTTTAAT
        AGAAACGAATATTCCGGTCACCACGGTTTAAAATTA
          **   *  **  **  *
3'- AGCAGTGTCAAAAGACGCGGAGTTCACGAT-5'
              primer HTLV1-A2
```

PCR mutagenesis ligate with pBluescript SK pAP 205 linker
(HTLV1-A variant)

```
TCTGCGCCTCAAGTGCTACCGGTGATGCATCCTAAT
AGACGCGGAGTTCACGATGGCCACTACGTAGGATTA
```

FIGURE 16D

```
              10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTGCGCCTCAAGTGCTACCGGTGATGCATCCTAATGC
    AGCAGTGTCAAAAGACGCGGAGTTCACGATGGCCACTACGTAGGATTACG

951 TGATGTTTGTATGGATCCTGAGCCCATAGTGCGTATCGTAGGTCGAAATG
```

FIGURE 16D (CONT'D)

```
           ACTACAAACATACCTAGGACTCGGGTATCACGCATAGCATCCAGCTTTAC
     1001  GTCTATGTGTTGATGTTAGGGATGGAAGATTCCACAACGGAAACGCAATA
           CAGATACACAACTACAATCCCTACCTTCTAAGGTGTTGCCTTTGCGTTAT
     1051  CAGTTGTGGCCATGCAAGTCTAATACAGATGCAAATCAGCTCTGGACTTT
           GTCAACACCGGTACGTTCAGATTATGTCTACGTTAGTCGAGACCTGAAA
     1101  GAAAAGAGACAATACTATTCGATCTAATGGAAAGTGTTTAACTACTTACG
           CTTTTCTCTGTTATGATAAGCTAGATTACCTTTCACAAATTGATGAATGC
     1151  GGTACAGTCCGGGAGTCTATGTGATGATCTATGATTGCAATACTGCTGCA
           CCATGTCAGGCCCTCAGATACACTACTAGATACTAACGTTATGACGACGT
     1201  ACTGATGCCACCCGCTGGCAAATATGGGATAATGGAACCATCATAAATCC
           TGACTACGGTGGGCGACCGTTTATACCCTATTACCTTGGTAGTATTTAGG
     1251  CAGATCTAGTCTAGTTTTAGCAGCGACATCAGGGAACAGTGGTACCACAC
           GTCTAGATCAGATCAAAATCGTCGCTGTAGTCCCTTGTCACCATGGTGTG
     1301  TTACAGTGCAAACCAACATTTATGCCGTTAGTCAAGGTTGGCTTCCTACT
           AATGTCACGTTTGGTTGTAAATACGGCAATCAGTTCCAACCGAAGGATGA
     1351  AATAATACACAACCTTTTGTTACAACCATTGTTGGGCTATATGGTCTGTG
           TTATTATGTGTTGGAAAACAATGTTGGTAACAACCCGATATACCAGACAC
     1401  CTTGCAAGCAAATAGTGGACAAGTATGGATAGAGGACTGTAGCAGTGAAA
           GAACGTTCGTTTATCACCTGTTCATACCTATCTCCTGACATCGTCACTTT
     1451  AGGCTGAACAACAGTGGGCTCTTTATGCAGATGGTTCAATACGTCCTCAG
           TCCGACTTGTTGTCACCCGAGAAATACGTCTACCAAGTTATGCAGGAGTC
     1501  CAAAACCGAGATAATTGCCTTACAAGTGATTCTAATATACGGGAAACAGT
           GTTTTGGCTCTATTAACGGAATGTTCACTAAGATTATATGCCCTTTGTCA
     1551  TGTTAAGATCCTCTCTTGTGGCCCTGCATCCTCTGGCCAACGATGGATGT
           ACAATTCTAGGAGAGAACACCGGGACGTAGGAGACCGGTTGCTACCTACA
     1601  TCAAGAATGATGGAACCATTTTAAATTTGTATAGTGGATTGGTGTTAGAT
           AGTTCTTACTACCTTGGTAAAATTTAAACATATCACCTAACCACAATCTA
     1651  GTGAGGCGATCGGATCCGAGCCTTAAACAAATCATTCTTTACCCTCTCCA
           CACTCCGCTAGCCTAGGCTCGGAATTTGTTTAGTAAGAAATGGGAGAGGT
     1701  TGGTGACCCAAACCAAATATGGTTACCATTATTTTGATAGACAGATTACT
           ACCACTGGGTTTGGTTTATACCAATGGTAATAAAACTATCTGTCTAATGA
     1751  CTCTTGCAGTGTGTGTCCTGCCATGAAAATAGATGGCTTAAATAAAAA
           GAGAACGTCACACACACAGGACGGTACTTTTATCTACCGAATTTATTTTT
     1801  GGACATTGTAAATTTTGTAACTGAAAGGACAGCAAGTTATATCGAATTCC
           CCTGTAACATTTAAAACATTGACTTTCCTGTCGTTCAATATAGCTTAAGG
     1851  TGCAG
           ACGTC
```

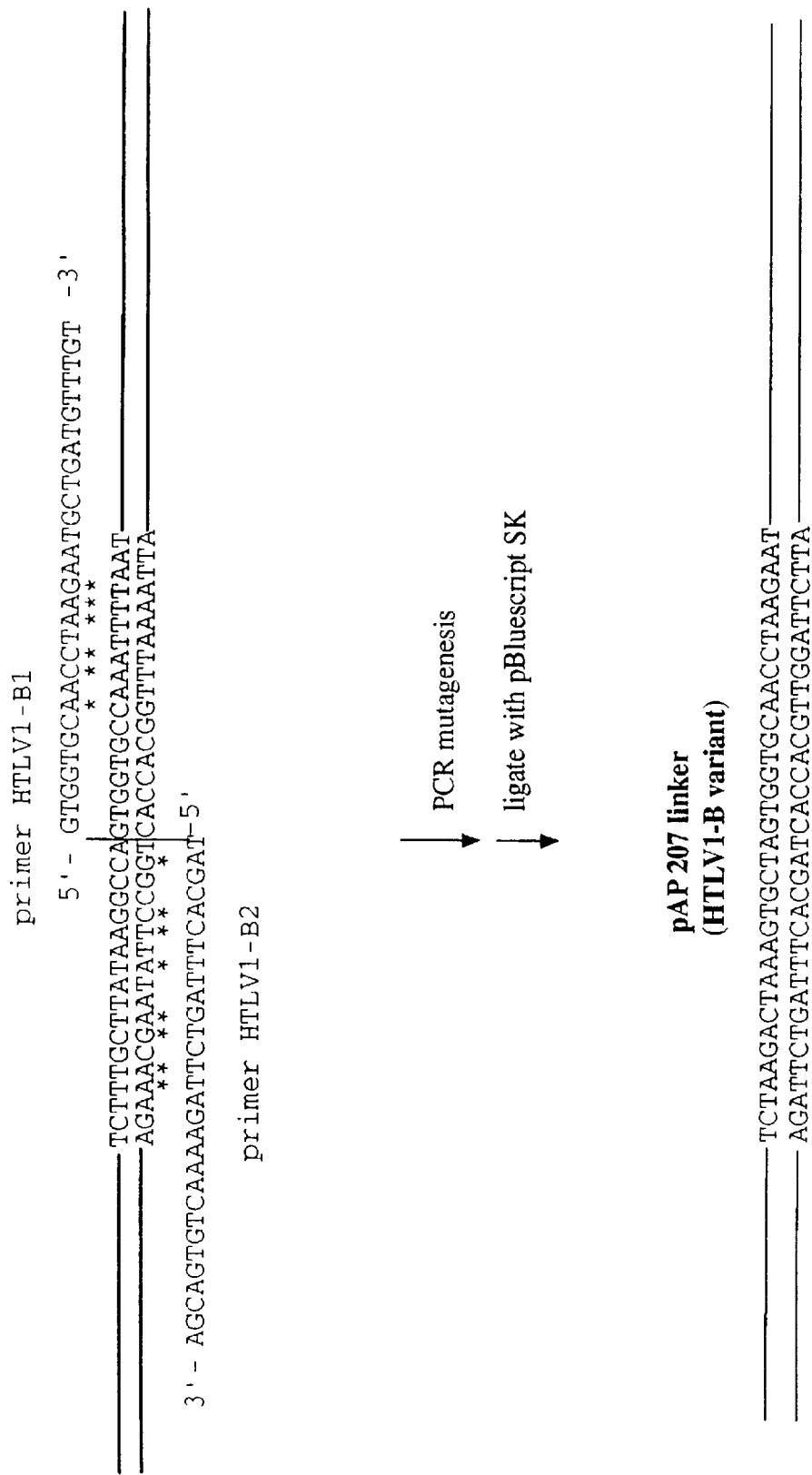

FIGURE 17D

```
              10         20         30         40         50
              |          |          |          |          |
    1   GAATTCATGAAACCGGGAGGAAATACTATTGTAATATGGATGTATGCAGT
        CTTAAGTACTTTGGCCCTCCTTTATGATAACATTATACCTACATACGTCA

51   GGCAACATGGCTTTGTTTTGGATCCACCTCAGGGTGGTCTTTCACATTAG
        CCGTTGTACCGAAACAAAACCTAGGTGGAGTCCCACCAGAAAGTGTAATC

101   AGGATAACAACATATTCCCCAAACAATACCCAATTATAAACTTTACCACA
        TCCTATTGTTGTATAAGGGGTTTGTTATGGGTTAATATTTGAAATGGTGT

151   GCGGGTGCCACTGTGCAAAGCTACACAAACTTTATCAGAGCTGTTCGCGG
        CGCCCACGGTGACACGTTTCGATGTGTTTGAAATAGTCTCGACAAGCGCC

201   TCGTTTAACAACTGGAGCTGATGTGAGACATGATATACCAGTGTTGCCAA
        AGCAAATTGTTGACCTCGACTACACTCTGTACTATATGGTCACAACGGTT

251   ACAGAGTTGGTTTGCCTATAAACCAACGGTTTATTTTAGTTGAACTCTCA
        TGTCTCAACCAAACGGATATTTGGTTGCCAAATAAAATCAACTTGAGAGT

301   AATCATGCAGAGCTTTCTGTTACATTAGCGCTGGATGTCACCAATGCATA
        TTAGTACGTCTCGAAAGACAATGTAATCGCGACCTACAGTGGTTACGTAT

351   TGTGGTCGGCTACCGTGCTGGAAATAGCGCATATTTCTTTCATCCTGACA
        ACACCAGCCGATGGCACGACCTTTATCGCGTATAAAGAAAGTAGGACTGT

401   ATCAGGAAGATGCAGAAGCAATCACTCATCTTTTCACTGATGTTCAAAAT
        TAGTCCTTCTACGTCTTCGTTAGTGAGTAGAAAAGTGACTACAAGTTTTA

451   CGATATACATTCGCCTTTGGTGGTAATTATGATAGACTTGAACAACTTGC
        GCTATATGTAAGCGGAAACCACCATTAATACTATCTGAACTTGTTGAACG

501   TGGTAATCTGAGAGAAAATATCGAGTTGGGAAATGGTCCACTAGAGGAGG
        ACCATTAGACTCTCTTTTATAGCTCAACCCTTTACCAGGTGATCTCCTCC

551   CTATCTCAGCGCTTTATTATTACAGTACTGGTGGCACTCAGCTTCCAACT
        GATAGAGTCGCGAAATAATAATGTCATGACCACCGTGAGTCGAAGGTTGA

601   CTGGCTCGTTCCTTTATAATTTGCATCCAAATGATTTCAGAAGCAGCAAG
        GACCGAGCAAGGAAATATTAAACGTAGGTTTACTAAAGTCTTCGTCGTTC

651   ATTCCAATATATTGAGGGAGAAATGCGCACGAGAATTAGGTACAACCGGA
        TAAGGTTATATAACTCCCTCTTTACGCGTGCTCTTAATCCATGTTGGCCT

701   GATCTGCACCAGATCCTAGCGTAATTACACTTGAGAATAGTTGGGGGAGA
        CTAGACGTGGTCTAGGATCGCATTAATGTGAACTCTTATCAACCCCCTCT

751   CTTTCCACTGCAATTCAAGAGTCTAACCAAGGAGCCTTTGCTAGTCCAAT
        GAAAGGTGACGTTAAGTTCTCAGATTGGTTCCTCGGAAACGATCAGGTTA

801   TCAACTGCAAAGACGTAATGGTTCCAAATTCAGTGTGTACGATGTGAGTA
        AGTTGACGTTTCTGCATTACCAAGGTTTAAGTCACACATGCTACACTCAT

851   TATTAATCCCTATCATAGCTCTCATGGTGTATAGATGCGCACCTCCACCA
        ATAATTAGGGATAGTATCGAGAGTACCACATATCTACGCGTGGAGGTGGT

901   TCGTCACAGTTTTCTAAGACTAAAGTGCTAGTGGTGCAACCTAAGAATGC
        AGCAGTGTCAAAAGATTCTGATTTCACGATCACCACGTTGGATTCTTACG

951   TGATGTTTGTATGGATCCTGAGCCCATAGTGCGTATCGTAGGTCGAAATG
        ACTACAAACATACCTAGGACTCGGGTATCACGCATAGCATCCAGCTTTAC
```

FIGURE 17D (CONT'D)

```
1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

FIGURE 18B

WT preproricin linker primer HTLV11-A1

```
5'-    GTGGTGCAACCTAGGAATGCTGATGTTTGT -3'
                    ||||||||||||||||
    TCTTTGCTTATAAGGCCCAGTGGTGCAACCTAGGAAATTTTAAT
    AGAAACGAATATTCCGGTCACCACG

FIGURE 18D

```
          10         20         30         40         50
           |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTAAGACTAAAGTGCTAGTGGTGCAACCTAGGAATGC
    AGCAGTGTCAAAAGATTCTGATTTCACGATCACCACGTTGGATCCTTACG

951 TGATGTTTGTATGGATCCTGAGCCCATAGTGCGTATCGTAGGTCGAAATG
    ACTACAAACATACCTAGGACTCGGGTATCACGCATAGCATCCAGCTTTAC
```

FIGURE 18D (CONT'D)

```
1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT

1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGATTGGTGTTAGAT
     AGTTCTTACTACCTTGGTAAAATTTAAACATATCACCTAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

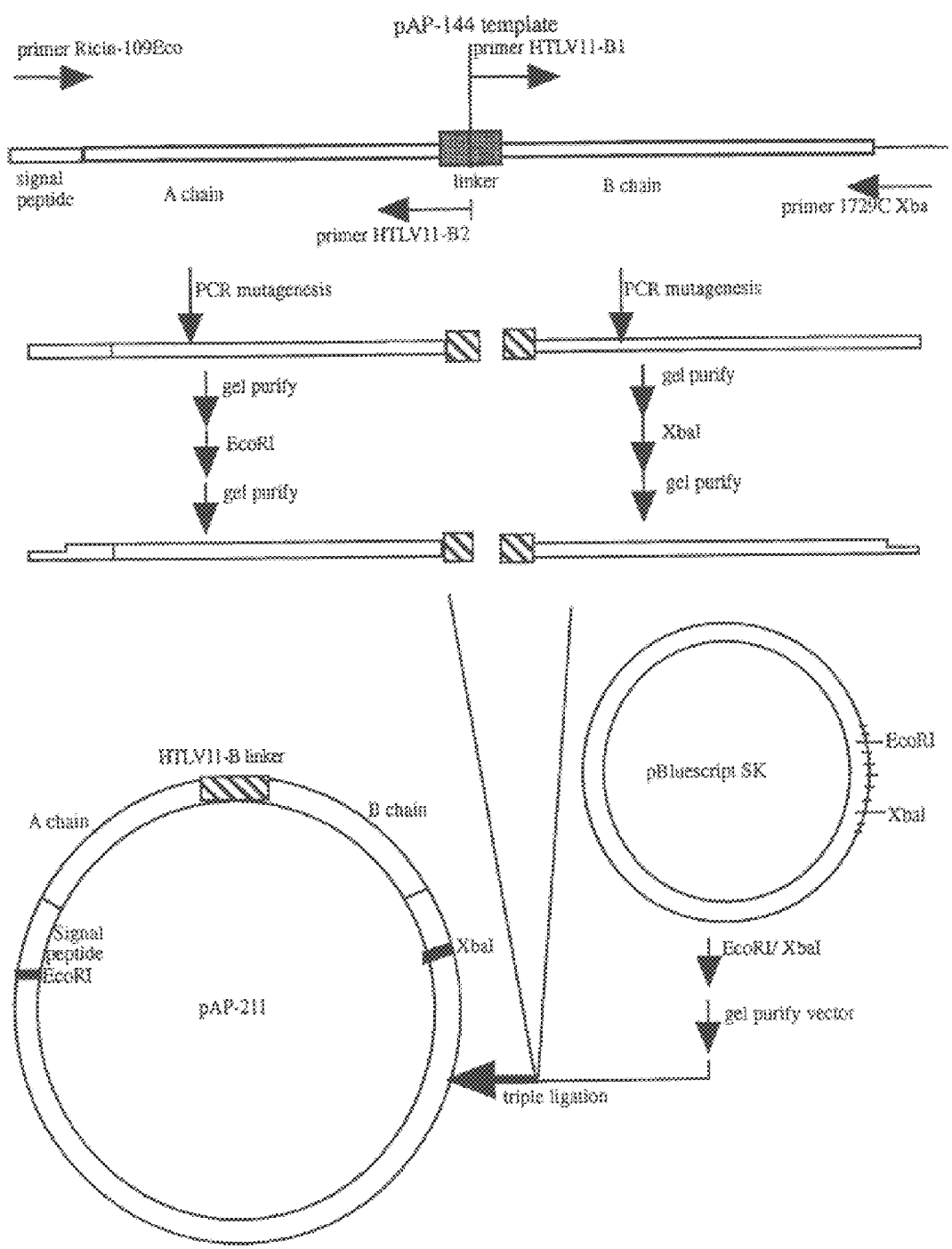

FIGURE 19B

WT preproricin linker

```
                        primer HTLV11-B1
                          5'- CCGATACTACATCCTAATGCTGATGTTTGT -3'
                              ** * * * *  **
          TCTTTGCTTATAAGGCCAGTGGTGCCAAATTTTAAT
          AGAAACGAATATTCCGGTCACCACGGTTTAAAATTA
            ** ** ** * ****
3'- AGCAGTGTCAAAAGATGCTGAGTTACAAAG-5'
              primer HTLV11-B2
```

PCR mutagenesis ligate with pBluescript SK pAP 211 linker
(HTLV11-B variant)

```
TCTACGACTCAATGTTTCCCGATACTACATCCTAAT
AGATGCTGAGTTACAAAGGGCTATGATGTAGGATTA
```

FIGURE 19D

```
           10         20         30         40         50
            |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGATATACCAGTGTTGCCAA
    AGCAAATTGTTGACCTCGACTACACTCTGTACTATATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT

701 GATCTGCACCAGATCCTAGCGTAATTACACTTGAGAATAGTTGGGGGAGA
    CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
    GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
    AGTTGACGTTTCTGCATTACCAAGGTTTAAGTCACACATGCTACACTCAT

851 TATTAATCCCTATCATAGCTCTCATGGTGTATAGATGCGCACCTCCACCA
    ATAATTAGGGATAGTATCGAGAGTACCACATATCTACGCGTGGAGGTGGT

901 TCGTCACAGTTTTCTACGACTCAATGTTTCCCGATACTACATCCTAATGC
    AGCAGTGTCAAAGATGCTGAGTTACAAAGGGCTATGATGTAGGATTACG

951 TGATGTTTGTATGGATCCTGAGCCCATAGTGCGTATCGTAGGTCGAAATG
    ACTACAAACATACCTAGGACTCGGGTATCACGCATAGCATCCAGCTTTAC
```

FIGURE 19D (CONT'D)

```
1001  GTCTATGTGTTGATGTTAGGGATGGAAGATTCCACAACGGAAACGCAATA
      CAGATACACAACTACAATCCCTACCTTCTAAGGTGTTGCCTTTGCGTTAT

1051  CAGTTGTGGCCATGCAAGTCTAATACAGATGCAAATCAGCTCTGGACTTT
      GTCAACACCGGTACGTTCAGATTATGTCTACGTTTAGTCGAGACCTGAAA

1101  GAAAAGAGACAATACTATTCGATCTAATGGAAAGTGTTTAACTACTTACG
      CTTTTCTCTGTTATGATAAGCTAGATTACCTTTCACAAATTGATGAATGC

1151  GGTACAGTCCGGGAGTCTATGTGATGATCTATGATTGCAATACTGCTGCA
      CCATGTCAGGCCCTCAGATACACTACTAGATACTAACGTTATGACGACGT

1201  ACTGATGCCACCCGCTGGCAAATATGGGATAATGGAACCATCATAAATCC
      TGACTACGGTGGGCGACCGTTTATACCCTATTACCTTGGTAGTATTTAGG

1251  CAGATCTAGTCTAGTTTTAGCAGCGACATCAGGGAACAGTGGTACCACAC
      GTCTAGATCAGATCAAAATCGTCGCTGTAGTCCCTTGTCACCATGGTGTG

1301  TTACAGTGCAAACCAACATTTATGCCGTTAGTCAAGGTTGGCTTCCTACT
      AATGTCACGTTTGGTTGTAAATACGGCAATCAGTTCCAACCGAAGGATGA

1351  AATAATACACAACCTTTTGTTACAACCATTGTTGGGCTATATGGTCTGTG
      TTATTATGTGTTGGAAAACAATGTTGGTAACAACCCGATATACCAGACAC

1401  CTTGCAAGCAAATAGTGGACAAGTATGGATAGAGGACTGTAGCAGTGAAA
      GAACGTTCGTTTATCACCTGTTCATACCTATCTCCTGACATCGTCACTTT

1451  AGGCTGAACAACAGTGGGCTCTTTATGCAGATGGTTCAATACGTCCTCAG
      TCCGACTTGTTGTCACCCGAGAAATACGTCTACCAAGTTATGCAGGAGTC

1501  CAAAACCGAGATAATTGCCTTACAAGTGATTCTAATATACGGGAAACAGT
      GTTTTGGCTCTATTAACGGAATGTTCACTAAGATTATATGCCCTTTGTCA

1551  TGTTAAGATCCTCTCTTGTGGCCCTGCATCCTCTGGCCAACGATGGATGT
      ACAATTCTAGGAGAGAACACCGGGACGTAGGAGACCGGTTGCTACCTACA

1601  TCAAGAATGATGGAACCATTTTAAATTTGTATAGTGGATTGGTGTTAGAT
      AGTTCTTACTACCTTGGTAAAATTTAAACATATCACCTAACCACAATCTA

1651  GTGAGGCGATCGGATCCGAGCCTTAAACAAATCATTCTTTACCCTCTCCA
      CACTCCGCTAGCCTAGGCTCGGAATTTGTTTAGTAAGAAATGGGAGAGGT

1701  TGGTGACCCAAACCAAATATGGTTACCATTATTTTGATAGACAGATTACT
      ACCACTGGGTTTGGTTTATACCAATGGTAATAAAACTATCTGTCTAATGA

1751  CTCTTGCAGTGTGTGTGTCCTGCCATGAAAATAGATGGCTTAAATAAAAA
      GAGAACGTCACACACACAGGACGGTACTTTTATCTACCGAATTTATTTTT

1801  GGACATTGTAAATTTTGTAACTGAAAGGACAGCAAGTTATATCGAATTCC
      CCTGTAACATTTAAAACATTGACTTTCCTGTCGTTCAATATAGCTTAAGG

1851  TGCAG
      ACGTC
```

FIGURE 20

```
Wild type Ricin linker:    A chain- S L L I R P V V P N F N -B chain pAP-205 linker:            A chain- S A P Q V L P V M H P N -B chain
pAP-206
(HTLV1-A linker)

pAP-207 linker:            A chain- S K T K V L V V Q P K N -B chain
pAP-208
(HTLV1-B linker)

pAP-209 linker:            A chain- S I R K I L F L D G I N -B chain
pAP-210
(HTLV11-A linker)

pAP-211 linker:            A chain- S T T Q C F P I L H P N -B chain
pAP-212
(HTLV11-B linker)
```

ANTIVIRAL RICIN-LIKE PROTEINS

This application is a national stage filing of PCT/CA97/00288. This application also claims benefit to Provisional Application No. 60/016,509 filed Apr. 30, 1996.

FIELD OF THE INVENTION

The invention relates to proteins having A and B chains of a ricin-like toxin, linked by a linker sequence which is specifically cleavable by a retroviral protease to release the active A chain. The invention also relates to a nucleic acid molecule encoding the protein and to expression vectors incorporating the nucleic acid molecule. Also provided is a method of inhibiting or destroying mammalian cells infected with a retrovirus utilizing the proteins of the invention and pharmaceutical compositions for treating HIV infection.

BACKGROUND OF THE INVENTION

Bacteria and plants are known to produce cytotoxic proteins which may consist of one, two or several polypeptides or subunits. Those proteins having a single subunit may be loosely classified as Type I proteins. Many of the cytotoxins which have evolved two subunit structures are referred to as type II proteins (Saelinger, C. B. in *Trafficking of Bacterial Toxins* (eds. Saelinger, C. B.) 1–13 (CRC Press Inc., Boca Raton, Fla., 1990). One subunit, the A chain, possesses the toxic activity whereas the second subunit, the B chain, binds cell surfaces and mediates entry of the toxin into a target cell. A subset of these toxins kill target cells by inhibiting protein biosynthesis. For example, bacterial toxins such as diphtheria toxin or Pseudomonas exotoxin inhibit protein synthesis by inactivating elongation factor 2. Plant toxins such as ricin work by directly inactivating ribosomes [Olsnes, S. & Phil, A. in Molecular action of toxins and viruses (eds. Cohen, P. & vanHeyningen, S.); 51–105 (Elsevier Biomedical Press, Amsterdam, 1982].

Ricin, derived from the seeds of *Ricinus communis* (castor oil plant), is the most potent of the plant toxins. It is estimated that a single ricin A chain is able to inactivate ribosomes at a rate of 1500 ribosomes/minute. Consequently, a single molecule of ricin is enough to kill a cell (Olsnes, S. & Phil, A. in *Molecular action of toxins and viruses* (eds. Cohen, P. & vanHeyningen, S.) 51–105 (Elsevier Biomedical Press, Amsterdam, 1982). The ricin toxin is a glycosylated heterodimer with A and B chain molecular masses of 30,625 Da and 31,431 Da respectively. The A chain of ricin has an N-glycosidase activity and catalyzes the excision of a specific adenine residue from the 28S rRNA of eukaryotic ribosomes (Endo, Y; & Tsurugi, K. *J. Biol. Chem.* 262:8128 (1987)). The B chain of ricin, although not toxic in itself, promotes the toxicity of the A chain by binding to galactose residues on the surface of eukaryotic cells and stimulating receptor-mediated endocytosis of the toxin molecule (Simmons et al. *Biol. Chem.* 261:7912 (1986)).

Protein toxins are initially produced in an inactive, precursor form. Ricin is initially produced as a single polypeptide (preproricin) with a 35 amino acid N-terminal presequence and 12 amino acid linker between the A and B chains. The pre-sequence is removed during translocation of the ricin precursor into the endoplasmic reticulum (Lord, J. M. *Eur. J. Biochem.* 146:403–409 (1985) and Lord, J. M. *Eur. J. Biochem.* 146:411–416 (1985)). The proricin is then translocated into specialized organelles called protein bodies where a plant protease cleaves the protein at a linker region between the A and B chains (Lord, J. M. et al., *FASAB Journal* 8:201–208 (1994)). The two chains, however, remain covalently attached by an interchain disulfide bond (cysteine 259 in the A chain to cysteine 4 in the B chain) and mature disulfide linked ricin is secreted from the plant cells. The A chain is inactive in the proricin (O'Hare, M., et al. *FEBS Lett.* 273:200–204 (1990)) and it is inactive in the disulfide-linked mature ricin (Richardson, P. T., et al. *FEBS Lett.* 255:15–20 (1989)). The ribosomes of the castor bean plant are themselves susceptible to inactivation by ricin A chain; however, as there is no cell surface galactose to permit B chain recognition the A chain cannot re-enter the cell. The exact mechanism of A chain release and activation in target cell cytoplasm is not known (Lord, J. M. et al., *FASAB Journal* 8:201–208 (1994)). However, it is known that for activation to take place the disulfide bond between the A and B chains must be reduced and, hence, the linkage between subunits broken.

The ricin gene has been cloned and sequenced, and the X-ray crystal structures of the A and B chains have been described (Rutenber, E., et al. Proteins 10:240–250 (1991); Weston et al., Mol. Bio. 244.410–422, 1994; Lamb and Lord *Eur. J. Biochem.* 14:265 (1985); Halling, K., et al. *Nucleic Acids Res.* 13:8019 (1985)). Due to its extreme toxicity there has been much interest in making ricin-based immunotoxins as therapeutic agents for destroying or inhibiting target cells or organisms (Vitetta et al., *Science* 238:1098–1104 (1987)). An immunotoxin is a conjugate of a specific cell-binding component, such as a monoclonal antibody or growth factor and the toxin in which the two protein components are covalently linked. Generally, the components are chemically coupled. However, the linkage may also be a peptide or disulfide bond. The antibody directs the toxin to cell types presenting a specific antigen thereby providing a specificity of action not possible with the natural toxin. Immunotoxins have been made both with the entire ricin molecule (i.e. both chains) and with the ricin A chain alone ( Spooner et al. *Mol. Immunol.* 31:117–125, (1994)).

Immunotoxins made with the ricin dimer (IT-Rs) are more potent toxins than those made with only the A chain (IT-As). The increased toxicity of IT-Rs is thought to be attributed to the dual role of the B chains in binding to the cell surface and in translocating the A chain to the cytosolic compartment of the target cell (Vitetta et al., *Science* 238:1098–1104(1987); Vitetta & Thorpe *Seminars in Cell Biology* 2:47–58 (1991)). However, the presence of the B chain in these conjugates also promotes the entry of the immunotoxin into nontarget cells. Even small amounts of B chain may override the specificity of the cell-binding component as the B chain binds nonspecifically to N-glycosylated galactose, present on most cells. IT-As are more specific and safer to use than IT-Rs. However, in the absence of the B chain the A chain has greatly reduced toxicity.

A number of immunotoxins have been designed to recognize antigens on the surfaces of tumour cells. A major problem with the use of ITs is that often the target antigen is also found on non-tumour cells (Vitetta et al., *Immunology Today* 14:252–259 (1993)). Also, due to the reduced potency of IT-As as compared to ITRs, large doses of IT-As must be administered to patients. The large doses frequently cause immune responses and production of neutralizing antibodies in patients (Vitetta et al., *Science* 238:1098–1104(1987)). IT-As and IT-Rs both suffer from reduced toxicity as the A chain is not released from the conjugate into the target cell cytoplasm.

The insertion of intramolecular cleavage sites between the cytotoxic and cell-binding components of a toxin can mimic the way that the natural toxin is activated. European patent application no. 466,222 describes the use of maize-derived pro-proteins which can be converted into active form by cleavage with extracellular blood enzymes such as factor Xa, thrombin or collagenase. Westby et al. (Bioconjugate Chem., 3:375–381, 1992) documented fusion proteins which have a specific cell binding component and proricin with a protease sensitive cleavage site specific for factor Xa within the linker sequence. O'Hare et al. (FEBS Lett. 273:200–204, 1990) also describe a recombinant fusion protein of RTA and staphylococcal protein A joined by a trypsin-sensitive cleavage site. In view of the prevalence of the extracellular proteases utilized in these approaches, such artificial activation of the toxin precursor or immunotoxin do not confer a mechanism for intracellular toxin activation, and the problems of target specificity and adverse immunological reactions to the cell-binding component of the immunotoxin remain.

In view of the extreme toxicity of proteins such as ricin, the lack of specificity of the immunotoxins may severely limit their usefulness as therapeutics for the treatment of cancer and infectious diseases. The preparation of a suitable specific cell binding component may be problematic. For example, antigens specific for the target cell may not be available and many potential target cells and infective organisms can alter their antigenic make up rapidly to avoid immune recognition.

The potential of bacterial and plant toxins for inhibiting mammalian retroviruses, particularly AIDS, has been investigated. Bacterial toxins such as Pseudomonas exotoxin-A and subunit A of diphtheria toxin; dual chain ribosomal inhibitory plant toxins, such as ricin and single chain ribosomal inhibitory proteins such as trichosanthin and poke weed antiviral protein have been used for the elimination of HIV infected cells (Olson et al. 1991, AIDS Res. and Human Retroviruses 7:1025–1030). The high toxicity of these toxins for mammalian cells, combined with a lack of specificity of action poses a major problem to the development of pharmaceuticals incorporating the toxins, such as immunotoxins.

Immunotoxins are designed such that their specificity of action is determined solely by the antibody component; antigen presenting cells are preferentially destroyed by the drug (Pastan et al., *Annals New York Academy of Sciences* 758:345–353 (1995)). The toxin protein of immunotoxin conjugates does not give the therapeutic any additional specificity of action; it will bring about the destruction of any cell it is delivered to.

SUMMARY OF THE INVENTION

The present inventors have prepared novel recombinant toxic proteins which are specifically toxic to cells infected with retroviruses and which do not depend for their specificity of action on a specific cell-binding component. The recombinant proteins of the invention have an A chain of a ricin-like toxin linked to a B chain by a linker sequence, which may be specifically cleaved by a retroviral protease within infected cells to activate the toxic A chain.

In one aspect, the present invention provides a purified and isolated nucleic acid having a nucleotide sequence encoding an A chain of a ricin-like toxin, a B chain of a ricin-like toxin and a heterlogous linker amino acid sequence, linking the A and B chains. The linker sequence is not a linker sequence of a ricin-like toxin, but rather the heterologous linker sequence contains a cleavage recognition site for a retroviral protease. The A and or the B chain may be those of ricin.

In an embodiment, the cleavage recognition site is the cleavage recognition site for an HIV protease. In a particular embodiment, the linker amino acid sequence comprises VSQNYPIVQNFN (SEQ ID NO:20); SKARVLAEAMSN (SEQ ID NO:21); or SIRKILFLDGIN (SEQ ID NO:22). In further particular embodiments, the nucleic acid has the nucleotide sequence shown in FIG. 8 (SEQ ID NO:23), FIG. 9 (SEQ ID NO:24) or FIG. 10 (SEQ ID NO:25).

In another embodiment, the cleavage recognition site is the cleavage recognition site for a human T-cell leukemia virus protease. In a particular embodiment, the linker amino acid sequence comprises SAPQVLPVMHPN (SEQ ID NO:55) or SKTKVLVVQPKN (SEQ ID NO:56) cleaved by a human T-cell leukemia virus-I (HTLV-I) protease; or, SKTKVLVVQPRN (SEQ ID NO:57) or STTQCFPILHPN (SEQ ID NO:58) cleaved by a human T-cell leukemia virus-II (HTLV-II) protease.

The present invention further provides a plasmid incorporating the nucleic acid of the invention. In an embodiment, the plasmid has the restriction map as shown in FIGS. 1A, 2A, 3A, 16A, 17A, 18A, or 19A.

In another embodiment, the present invention provides a baculovirus transfer vector incorporating the nucleic acid of the invention. In particular embodiments, the invention provides a baculovirus transfer vector having the restriction map as shown in FIGS. 5, 6, 7, 16C, 17C, 18C, or 19C or having the DNA sequence as shown in FIG. 11 (SEQ ID NO:26).

In a further aspect, the present invention provides a recombinant protein comprising an A chain of a ricin-like toxin, a B chain of a ricin-like toxin and a heterologous linker amino acid sequence, linking the A and B chains, wherein the linker sequence contains a cleavage recognition site for a retroviral protease. The A and or the B chain may be those of ricin.

In another aspect, the invention provides a method of inhibiting or destroying mammalian cells infected with a retrovirus having a protease, comprising the steps of preparing a recombinant protein of the invention having a heterologous linker sequence which contains a cleavage recognition site for the retrovirus protease and introducing the recombinant protein into the cells. In an embodiment, the retrovirus is HIV.

The present invention also relates to a method of treating a mammal infected with HIV by administering the recombinant proteins of the invention to the mammal.

Also provided is a process for preparing a pharmaceutical for treating a mammal infected with a retrovirus having a protease comprising the steps of preparing a purified and isolated nucleic acid having a nucleotide sequence encoding an A chain of a ricin-like toxin, a B chain of a ricin-like toxin and a heterologous linker amino acid sequence, linking the A and B chains, wherein the linker sequence contains a cleavage recognition site for the protease; introducing the nucleic acid into a host cell; expressing the nucleic acid in the host cell to obtain a recombinant protein comprising an A chain of a ricin-like toxin, a B chain of a ricin-like toxin and a heterlogous linker amino acid sequence, linking the A and B chains wherein the linker sequence contains the cleavage recognition site for the protease; and suspending the protein in a pharmaceutically acceptable carrier, diluent or excipient.

In an embodiment, a process is provided for preparing a pharmaceutical for treating a mammal infected with a retrovirus having a protease comprising the steps of identifying a cleavage recognition site for the protease; preparing a recombinant protein comprising an A chain of a ricin-like toxin, a B chain of a ricin-like toxin and a heterologous linker amino acid sequence, linking the A and B chains wherein the linker sequence contains the cleavage recognition site for the protease and suspending the protein in a pharmaceutically acceptable carrier, diluent or excipient.

In a further aspect, the invention provides a pharmaceutical composition for treating a retroviral infection, such as HIV, in a mammal comprising the recombinant protein of the invention and a pharmaceutically acceptable carrier, diluent or excipient.

The invention also contemplates a method for treating cancer cells containing an HTLV protease comprising (a) preparing a recombinant protein of the invention having a heterologous linker sequence which contains a cleavage recognition site for an HTLV protease; an (b) introducing the recombinant protein into the cells. The method can be used to treat a mammal with human T-cell leukemias involving HTLV. Compositions for treating human T-cell leukemias involving HTLV comprising the recombinant protein of the invention having a heterologous linker sequence which contains a cleavage recognition site for an HTLV protease, and a pharmaceutically acceptable carrier, diluent, or excipient are also provided.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

Figure 1A:
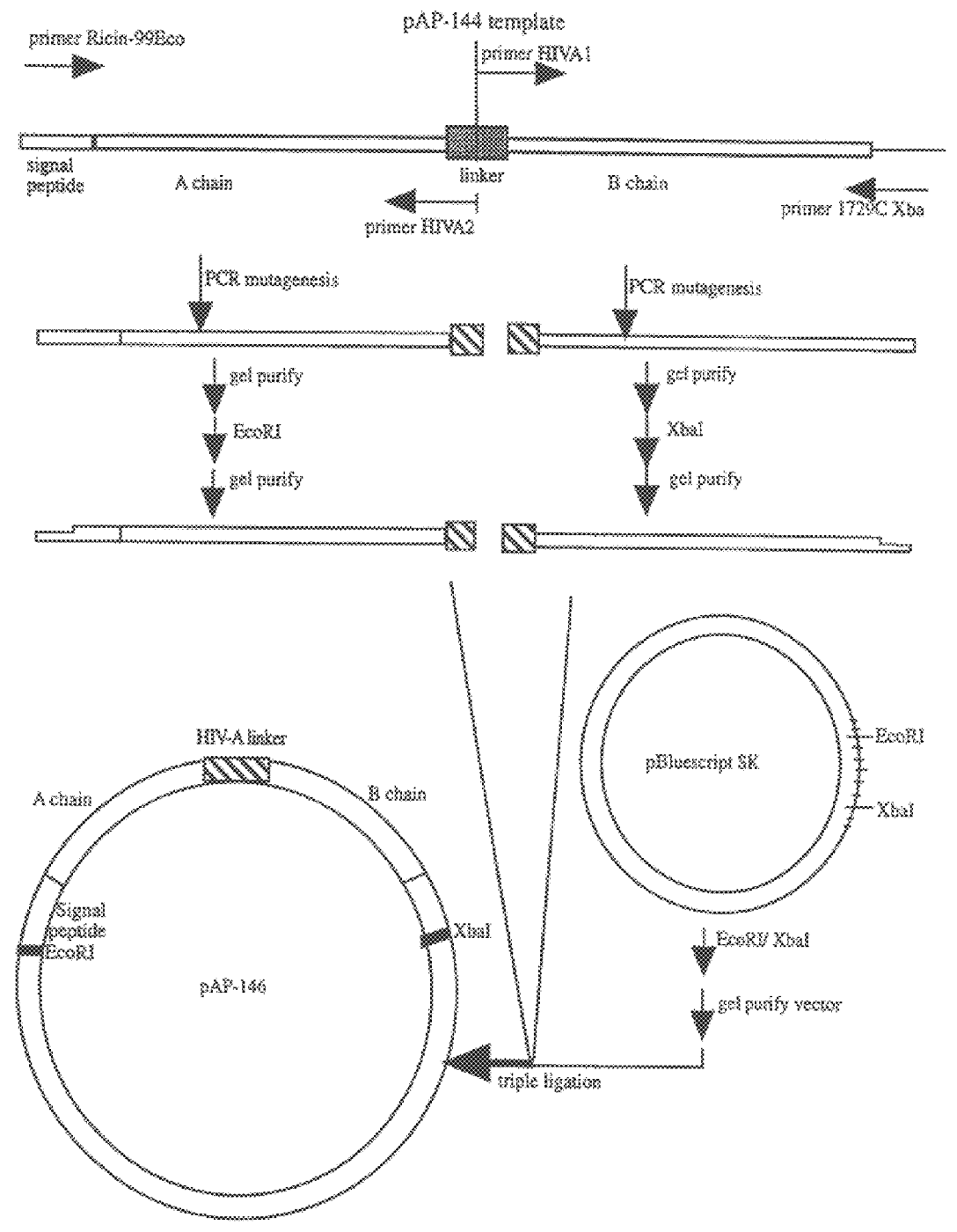

FIG. 1A summarizes the cloning strategy used to generate the pAP-146 construct;

FIG. 1B shows the nucleotide sequence of the HIV-A linker region of pAP-146 (SEQ ID NOS: 1–6);

FIG. 2A summarizes the cloning strategy used to generate the pAP-147 construct;

FIG. 2B shows the nucleotide sequence of the HIV-B linker region of pAP-147 (SEQ ID NOS: 7–12);

Figure 3A:
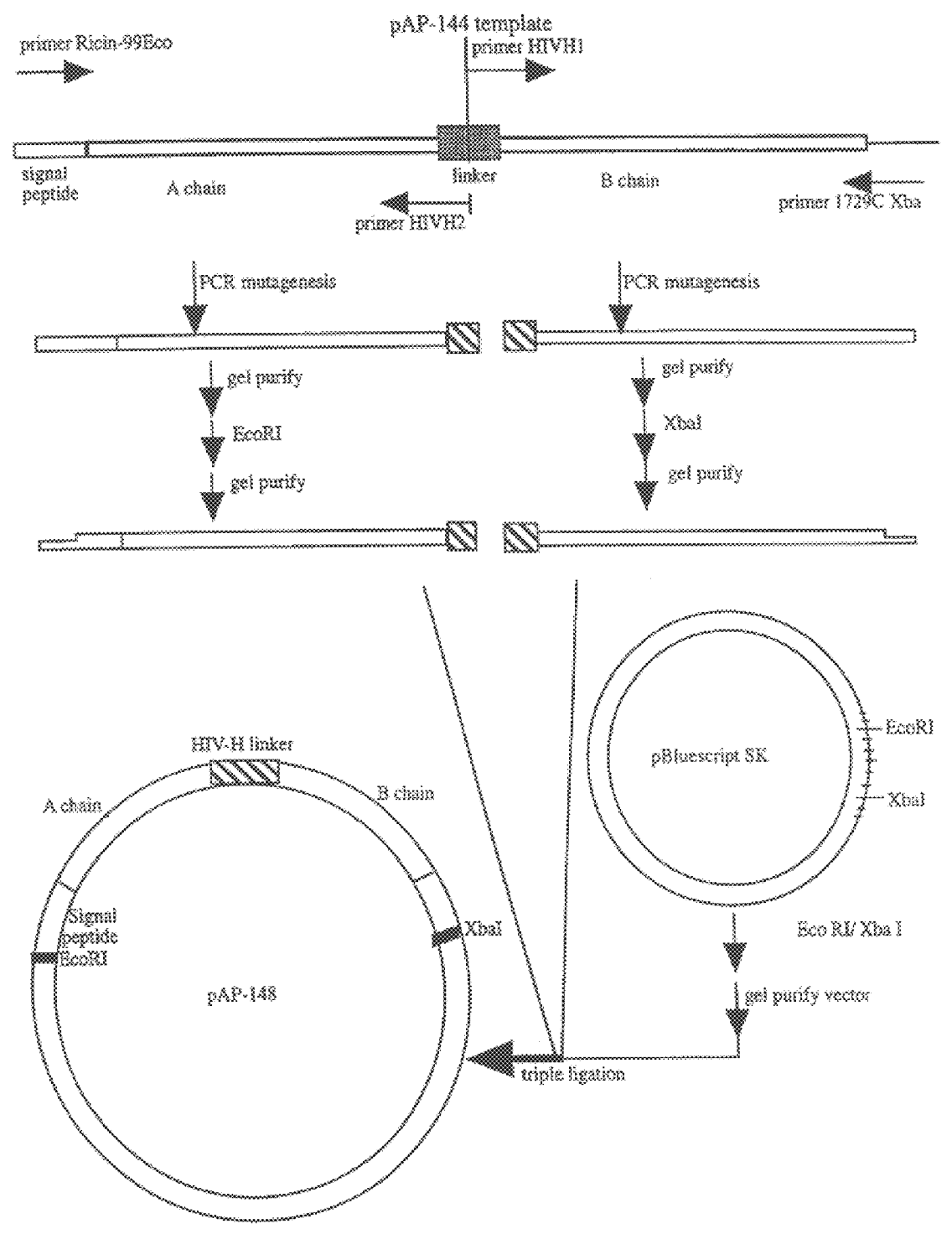

FIG. 3A summarizes the cloning strategy used to generate the pAP-148 construct;

FIG. 3B shows the nucleotide sequence of the HIV-H linker region of pAP-148;

FIG. 4 shows the amino acid sequences of the wild type ricin linker (SEQ ID NOS: 19), the pAP-146 (SEQ ID NO: 20) linker, the pAP-147 (SEQ ID NO:21) linker and the pAP-148 linker (SEQ ID NO:22);

FIG. 8 shows the DNA sequence of the pAP-190 insert (SEQ ID NO:23);

FIG. 9 shows the DNA sequence of the pAP-196 insert (SEQ ID NO: 24);

FIG. 10 shows the DNA sequence of the pAP-197 insert (SEQ ID NO: 25);

FIG. 11 shows the DNA sequence of the baculovirus transfer vector pVL1393(SEQ ID NO:26);

FIG. 13 shows a Western Blot of a pAP-190 proricin variant;

FIG. 16B shows the nucleotide sequence of the HTLV-I-A linker regions of pAP-205 (SEQ ID NO:27–32);

FIG. 16D shows the DNA sequence of the pAP-206 insert containing ricin and the HTLV-I-A linker (SEQ ID NO: 33);

FIG. 17B shows the nucleotide sequence of the HTLV-I-B linker regions of pAP-207 (SEQ ID NO:34–39)

FIG. 17D shows the DNA sequence of the pAP-208 insert containing ricin and the HTLV-I-B linker (SEQ ID NO:40);

FIG. 18B shows the nucleotide sequence of the HTLV-II-A linker regions of pAP-209 (SEQ ID NOS: 41–46)

FIG. 18D shows the DNA sequence of the pAP-210 insert containing ricin and the HTLV-II-A linker (SEQ ID NO: 47);

FIG. 19A is a diagram summarizing the cloning strategy used to generate the pAP-211 construct;

FIG. 19B shows the nucleotide sequence of the HTLV-II-B linker regions of pAP-211 (SEQ ID NOS: 48–53)

FIG. 19D shows the DNA sequence of the pAP-212 insert containing ricin and the HTLV- linker (SEQ ID NO:54); and FIG. 20 shows the amino acid sequences of the wild type ricin linker and HTLV protease-sensitive amino acid linkers contained in linkers pAP-205 to pAP-212 (SEQ ID NOS: 55–58).

DETAILED DESCRIPTION OF THE INVENTION

Nucleic Acid Molecules of the Invention

Figure 5:
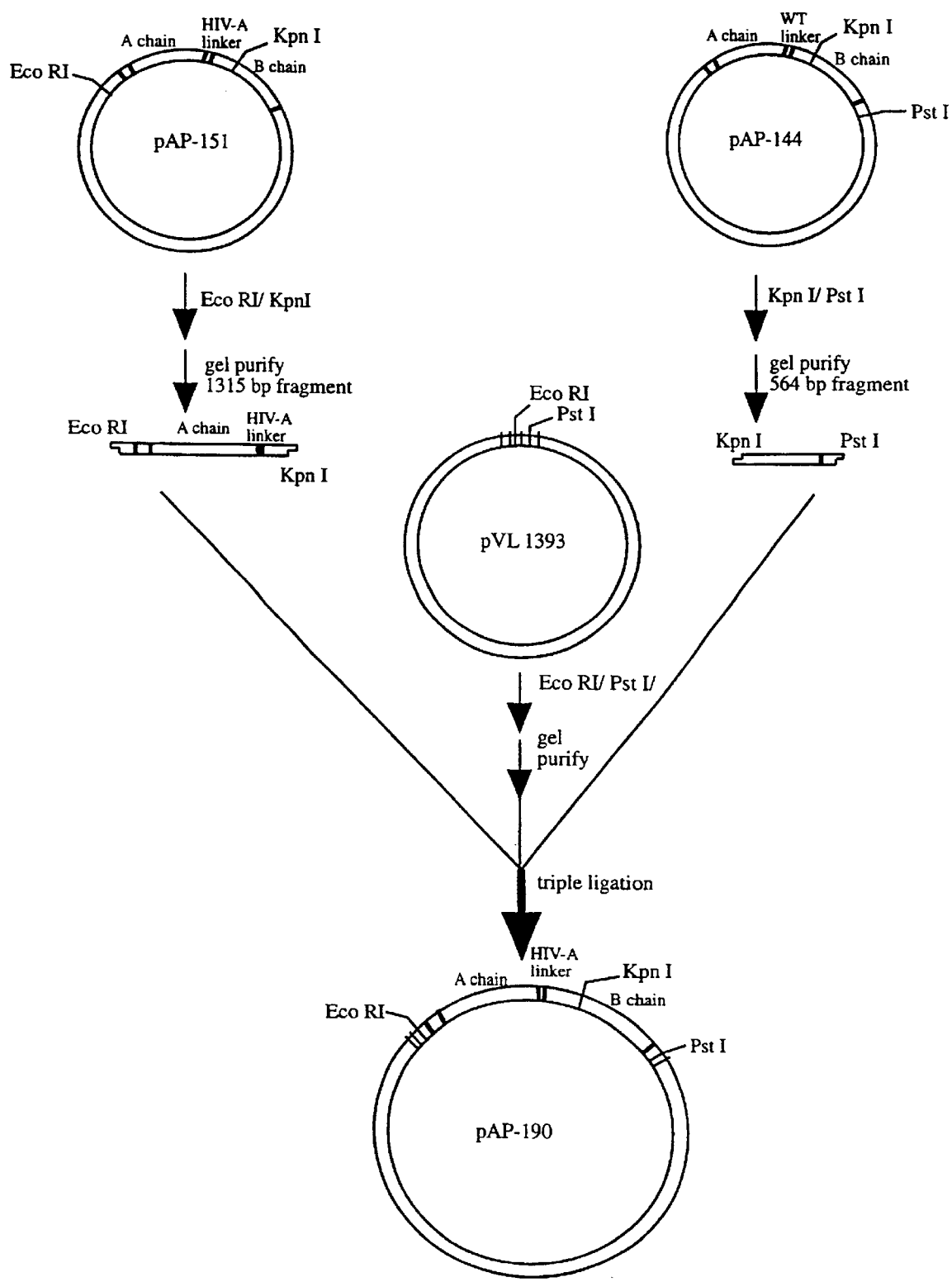
FIG. 5 shows the subcloning of the HIV-A linker variant into a baculovirus transfer vector.

The present inventors have cloned and expressed novel nucleic acid molecules having a nucleotide sequence encoding an A chain of a ricin-like toxin, a B chain of a ricin-like toxin and a heterologous linker amino acid sequence, linking the A and B chains. The heterologous linker sequence contains a cleavage recognition site for a retroviral protease such as a cleavage recognition site for HIV or a human T-cell leukemia virus protease.

The term "isolated and purified" as used herein refers to a nucleic acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e., sequences located at the 5' and 3' ends of the nucleic acid) from which the nucleic acid is derived. The term "nucleic acid" is intended to include DNA and RNA and can be either double stranded or single stranded.

The term "linker sequence" as used herein refers to an internal amino acid sequence within the protein encoded by the nucleic acid molecule of the invention which contains residues linking the A and B chain so as to render the A chain incapable of exerting its toxic effect, for example catalytically inhibiting translation of a eukaryotic ribosome. By heterologous is meant that the linker sequence is not a sequence native to the A or B chain of a ricin-like toxin or precursor thereof. However, preferably, the linker sequence may be of a similar length to the linker sequence of a ricin-like toxin and should not interfere with the role of the B chain in cell binding and transport into the cytoplasm. When the linker sequence is cleaved the A chain becomes active or toxic.

The nucleic acid molecule of the invention was cloned by subjecting a preproricin cDNA clone (pAP-144) to site-directed mutagenesis in order to generate a series of variants differing only in the sequence between the A and B chains (linker region). Oligonucleotides, corresponding to the extreme 5' and 3' ends of the preproricin gene were synthesized and used to PCR amplify the gene. Using the cDNA sequence for preproricin (Lamb et al., Eur. J. Biochem., 145:266–270, 1985), several oligonucleotide primers were designed to flank the start and stop codons of the preproricin open reading frame.

The preproricin cDNA was amplified using the upstream primer Ricin-99 (or Ricin-109 may be used) and the downstream primer Ricin729C with Vent DNA polymerase (New England Biolabs) using standard procedures (Sambrook et al., Molecular Cloning: A Laboratory Manual, Second Edition, (Cold Spring Harbor Laboratory Press, 1989)). The use of the upstream primer Ricin-109 circumvents the subcloning step into vector pSB2. The purified PCR fragment encoding the preproricin cDNA was then ligated into an Eco RV-digested pBluescript II SK plasmid (Stratagene), and used to transform competent XL1-Blue cells (Stratagene).

The cloned PCR product containing the putative preproricin gene was confirmed by DNA sequencing of the entire cDNA clone (pAP-144). The sequences and location of oligonucleotide primers used for sequencing are shown in Table 1 (SEQ ID NOS: 61–71).

The preproricin cDNA clone (pAP-144) was subjected to site-directed mutagenesis in order to generate a series of variants differing only in the sequence between the A and B chains (linker region). The wild-type preproricin linker region was replaced with the three linker sequences, pAP-146 (SEQ ID NO:20), pAP-147 (SEQ ID NO:21) and pAP-148 (SEQ ID NO: 22) shown in FIG. 4. The linker regions of the variants encode an HIV protease cleavage recognition sequence (Slalka et al., Cell, 56:911–913, 1989). The mutagenesis and cloning strategy used to generate the linker variants pAP-146, pAP-147 and pAP-148 are summarized in FIGS. 1A and 1B, 2A and 2B and 3A and 3B respectively. The first step involved a DNA amplification using a set of mutagenic primers (HIVA 1, 2 (SEQ ID NOS: 3–4); HIVB 1, 2 (SEQ ID NOS:9–10); HIVH 1, 2 (SEQ ID NOS: 15–16)) in combination with the two flanking primers Ricin-99Eco and Ricin1729Xba. Restriction digested PCR fragments were gel purified and then ligated with PBluescript SK which had been digested with Eco RI and Xba I. Ligation reactions were used to transform competent XL1-Blue cells (Stratagene). Recombinant clones were identified by restriction digests of plasmid miniprep DNA and the mutant linker sequences were confirmed by DNA sequencing.

Recombinant clones were subcloned into vector pSB2. The three constructs obtained were pAP-151, pAP-159, and pAP-163, with each having the mutant linker found in pAP-146, pAP-147, and pAP-148 respectively.

The cloning strategy described above may also be applied to the preparation of recombinant clones containing a cleavage recognition site for a human T-cell leukemia virus protease. For example, recombinant clones pAP-205, pAP-207, pAP-209, and pAP-211 were prepared using a method similar to the one described above.

The nucleic acid molecule of the invention has sequences encoding an A chain of a ricin-like toxin, a B chain of a ricin-like toxin and a heterologous linker sequence containing a cleavage recognition site for a retroviral protease, such as an HIV protease or an HTLV protease. The nucleic acid may be expressed to provide a recombinant protein having an A chain of a ricin-like toxin, a B chain of a ricin-like toxin and a heterologous linker sequence containing a cleavage recognition site for a retroviral protease, such as an HIV protease or an HTLV protease.

The nucleic acid molecule may comprise the A and/or B chain of ricin. The ricin gene has been cloned and sequenced, and the X-ray crystal structures of the A and B chains are published (Rutenber, E., et al. Proteins 10:240–250 (1991); Weston et al., Mol. Bio. 244:410–422, 1994; Lamb and Lord Eur. J. Biochem. 14:265 (1985); Halling, K., et al. Nucleic Acids Res. 13:8019 (1985)). It will be appreciated that the invention includes nucleic acid molecules encoding truncations of A and B chains of ricin-like proteins and analogs and homologs of A and B chains of ricin-like proteins and truncations thereof (i.e.,ricin-like proteins), as described herein. It will further be appreciated that variant forms of the nucleic acid molecules of the invention which arise by alternative splicing of an mRNA corresponding to a cDNA of the invention are encompassed by the invention.

Another aspect of the invention provides a nucleotide sequence which hybridizes under high stringency conditions to a nucleotide sequence encoding the A and/or B chains of a ricin-like protein. Appropriate stringency conditions which promote DNA hybridization are known to those skilled in the art, or can be found in Current Protocols in Molecular Biology, John Wiley & Sons, New York (1989), 6.3.1–6.3.6. For example, 6.0×sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

The nucleic acid molecule may comprise the A and/or B chain of a ricin-like toxin. Methods for cloning ricin-like toxins are known in the art and are described, for example, in E.P. 466,222. Sequences encoding ricin or ricin-like A and B chains may be obtained by selective amplification of a coding region, using sets of degenerate primers or probes for selectively amplifying the coding region in a genomic or cDNA library. Appropriate primers may be selected from the nucleic acid sequence of A and B chains of ricin or ricin-like toxins. It is also possible to design synthetic oligonucleotide primers from the nucleotide sequences for use in PCR. Suitable primers may be selected from the sequences encoding regions of ricin-like proteins which are highly conserved, as described for example in U.S. Pat. No. 5,101,025 and E.P. 466,222.

A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.). It will be appreciated that the methods described above may be used to obtain the coding sequence from plants, bacteria or fungi, preferably plants, which produce known ricin-like proteins and also to screen for the presence of genes encoding as yet unknown ricin-like proteins.

A sequence containing a cleavage recognition site for a retroviral protease may be selected based on the retrovirus which is to be targeted by the recombinant protein. The cleavage recognition site may be selected from sequences known to encode a cleavage recognition site for the retrovirus protease. Sequences encoding cleavage recognition sites may be identified by testing the expression product of the sequence for susceptibility to cleavage by a retroviral protease. An assay to identify peptides having cleavage recognition sites for HIV protease is described in PCT/US88/01849. The HIV protease encoded by the p17 gene of HIV and has the highly conserved Asp-Thr-Gly sequence characteristic of the active site of cellular aspartyl proteases. The HIV protease may be prepared by methods known in the art and used to test suspected cleavage recognition sites. For example, a polypeptide containing the suspected cleavage recognition site may be incubated with the protease and the amount of cleavage product determined (Dilannit, 1990, J. Biol. Chem. 285: 17345–17354). Substrates for HIV proteases are described in U.S. Pat. No. 5,235,039. The invention is not restricted to proteins including the cleavage recognition site for HIV proteases, but includes recognition sites of other retroviral proteases, including proteases of members of the subfamilies oncovirinae, lentivirinae and spumavirinae for example from HTLV, AMV, RSV, BLV, FeLV and MMTV. Examples of retroviral proteases and conserved sequences thereof are provided, for example, in Katoh et al., (Nature 329:654–656).

A sequence containing a cleavage recognition site for an HTLV protease may be selected using the conventional methods described herein. The preparation of human T-cell leukemia virus proteases, their substrates and enzymatic activity assay methodology have been described by Petit, S. C. et al. (J. Biol. Chem. 266:14539–14547 (1991)) and Blaha, I. et al. (FEBS Lett. 309:389–393 (1992)).

In an embodiment, the cleavage recognition site is the cleavage recognition site for an HIV protease. In a particular embodiment, the linker amino acid sequence comprises VSQNYPIVQNFN (SEQ ID NO:20); SKARVLAEAMSN (SEQ ID NO:21); or SIRKILFLDGIN (SEQ ID NO: 22). In further particular embodiments, the nucleic acid has the nucleotide sequence shown in FIG. 8 (SEQ ID NO:23), FIG. 9 (SEQ ID NO: 24) or FIG. 10 (SEQ ID NO:25).

In another embodiment, the cleavage recognition site is the cleavage recognition site for a human T-cell leukemia virus protease. In a particular embodiment, the linker amino acid sequence comprises SAPQVLPVMHPN or SKTKVLVVQPKN cleaved by a human T-cell leukemia virus-I (HTLV-I) protease; or, SKTKVLVVQPRN or STTQCFPIL-HPN cleaved by a human T-cell leukemia virus-II (HTLV-II) protease.

The nucleic acid molecule of the invention may be prepared by site directed mutagenesis. For example, the cleavage site of a retroviral protease may be prepared by site directed mutagenesis of the homologous linker sequence of a proricin-like toxin. Procedures for cloning proricin-like genes, encoding a linker sequence are described in EP 466,222. Site directed mutagenesis may be accomplished by DNA amplification of mutagenic primers in combination with flanking primers. Suitable procedures using the mutagenic primers HIVA1 (SEQ ID NO:3), HIVB1 (SEQ ID NO:9) and HIVH1 (SEQ ID NO: 15) are shown in FIGS. 1A to 3B, and FIGS. 16A, 16B, 17A, 17B, 18A, 19A and 19B.

The nucleic acid molecule of the invention may also encode a fusion protein. A sequence encoding a heterologous linker sequence containing a cleavage recognition site for a retroviral protease may be cloned from a cDNA or genomic library or chemically synthesized based on the known sequence of such cleavage sites. The heterologous linker sequence may then be fused in frame with the sequences encoding the A and B chains of the ricin-like toxin for expression as a fusion protein. It will be appreciated that a nucleic acid molecule encoding a fusion protein may contain a sequence encoding an A chain and a B chain from the same ricin-like toxin or the encoded A and B chains may be from different toxins. For example, the A chain may be derived from ricin and the B chain may be derived from abrin. A protein may also be prepared by chemical conjugation of the A and B chains and linker sequence using conventional coupling agents for covalent attachment.

An isolated and purified nucleic acid molecule of the invention which is RNA can be isolated by cloning a cDNA encoding an A and B chain and a linker into an appropriate vector which allows for transcription of the cDNA to produce an RNA molecule which encodes a protein of the invention. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

Recombinant Protein of the Invention

As previously mentioned, the invention provides novel recombinant proteins which incorporate the A and B chains of a ricin-like toxin linked by a heterologous linker sequence containing a cleavage recognition site for a retroviral protease, such as an HIV protease or an HTLV protease. It is an advantage of the recombinant proteins of the invention that they are non-toxic until the A chain is liberated from the B chain by specific cleavage of the linker by the retroviral protease, such as an HIV protease or an HTLV protease. Thus the protein may be used to specifically target cells infected with the retrovirus in the absence of additional specific cell-binding components to target infected cells. It is a further advantage that the retroviral protease cleaves the heterologous linker intracellularly thereby releasing the toxic A chain directly into the cytoplasm of the infected cell. As a result, infected cells are specifically targeted and non-infected cells are not directly exposed to the activated free A chain.

Ricin is a plant derived ribosome inhibiting protein which blocks protein synthesis in eukaryotic cells. Ricin may be derived from the seeds of *Ricinus communis* (castor oil plant).The ricin toxin is a glycosylated heterodimer with A and B chain molecular masses of 30,625 Da and 31,431 Da respectively. The A chain of ricin has an N-glycosidase activity and catalyzes the excision of a specific adenine residue from the 28S rRNA of eukaryotic ribosomes (Endo, Y; & Tsurugi, K. J. *Biol. Chem.* 262:8128 (1987)). The B chain of ricin, although not toxic in itself, promotes the toxicity of the A chain by binding to galactose residues on the surface of eukaryotic cells and stimulating receptor-mediated endocytosis of the toxin molecule (Simmons et al. *Biol. Chem.* 261:7912 (1986)).

Protein toxins are initially produced in an inactive, precursor form. Ricin is initially produced as a single polypeptide (preproricin) with a 35 amino acid N-terminal presequence and 12 amino acid linker between the A and B chains. The pre-sequence is removed during translocation of the ricin precursor into the endoplasmic reticulum (Lord, J. M. *Eur. J. Biochem.* 146:403–409 (1985) and Lord, J. M. *Eur. J. Biochem.* 146:411–416 (1985)). The proricin is then translocated into specialized organelles called protein bodies where a plant protease cleaves the protein at a linker region between the A and B chains 15 (Lord, J. M. et al., *FASAB Journal* 8:201–208 (1994)). The two chains, however, remain covalently attached by an interchain disulfide bond (cysteine 259 in the A chain to cysteine 4 in the B chain) and mature disulfide linked ricin is secreted from the plant cells. The A chain is inactive in the proricin (O'Hare, M., et al. *FEBS Lett.* 273:200–204 (1990)) and it is inactive in the disulfide-linked mature ricin(Richardson, P. T., et al. *FEBS Lett.* 255:15–20 (1989)). The ribosomes of the castor bean plant are themselves susceptible to inactivation by ricin A chain; however, as there is no cell surface galactose to permit B chain recognition the A chain cannot re-enter the cell.

Ricin-like proteins include bacterial, fungal and plant toxins which have A and B chains and inactivate ribosomes and inhibit protein synthesis. The A chain is an active polypeptide subunit which is responsible for the pharmacologic effect of the toxin. In most cases the active component of the A chain is an enzyme. The B chain is responsible for binding the toxin to the cell surface and is thought to facilitate entry of the A chain into the cell cytoplasm. The A and B chains in the mature toxins are linked by disulfide bonds. The toxins most similar in structure to ricin are plant toxins which have one A chain and one B chain. Examples of such toxins include abrin which may be isolated from the seeds of *Abrus precatorius,* ricin which may be isolated from the seeds of castor beans *Ricinus communis,* and modeccin.

Ricin-like bacterial proteins include diphtheria toxin, which is produced by *Corynebacterium diphtheriae,* Pseudomonas enterotoxin A and cholera toxin. It will be appreciated that the term ricin-like toxins is also intended to include the A chain of those toxins which have only an A chain. The recombinant proteins of the invention could include the A chain of these toxins conjugated to, or expressed as, a recombinant protein with the B chain of another toxin. Examples of plant toxins having only an A chain include trichosanthin, MMC and pokeweed antiviral proteins, dianthin 30, dianthin 32, crotin II, curcin II and wheat germ inhibitor. Examples of fungal toxins having only an A chain include alpha-sarcin, restrictocin, mitogillin, enomycin, phenomycin. Examples of bacterial toxins having only an A chain include cytotoxin from *Shigella dysenteriae* and related Shiga-like toxins. Recombinant trichosanthin and the coding sequence thereof is disclosed in U.S. Pat. Nos. 5,101,025 and 5,128,460.

In addition to the entire B or A chains of a ricin-like toxin, it will be appreciated that the recombinant protein of the invention may contain only that portion of the A chain which is necessary for exerting its cytotoxic effect. For example, the first 30 amino acids of the ricin A chain may be removed resulting in a truncated A chain which retains toxic activity. The truncated ricin or ricin-like A chain may be prepared by expression of a truncated gene or by proteolytic degradation, for example with Nagarase (Funmatsu et al., 1970, Jap. J. Med. Sci. Biol. 23:264–267). Similarly, the recombinant protein of the invention may contain only that portion of the B chain necessary for galactose recognition, cell binding and transport into the cell cytoplasm. Truncated B chains are described for example in EP 145,111. The A and B chains may be glycosylated or non-glycosylated. Glycosylated A and B chains may be obtained by expression in the appropriate host cell capable of glycosylation. Non-glycosylated chains may be obtained by expression in nonglycosylating host cells or by treatment to remove or destroy the carbohydrate moieties.

The proteins of the invention may be prepared using recombinant DNA methods. Accordingly, the nucleic acid molecules of the present invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, CA (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native A and B chains and/or its flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include E. coli, B. subtilis, Salmonella typhimurium, and various species within the genus' Pseudomonas, Streptomyces, and Staphylococcus, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20:231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:95, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.). Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Amann et al., (1988) Gene 69:301–315) and pET IId (Studier et al., Gene Expression Technology: Methods in Enzymology 185, Academic Press, San Diego, Calif. (1990) 60–89).

Yeast and fungi host cells suitable for carrying out the present invention include, but are not limited to Saccharomyces cerivisae, the genera Pichia or Kluyveromyces and various species of the genus Aspergillus. Examples of vectors for expression in yeast S. cerivisae include pYepSec1 (Baldari. et al., (1987) Embo J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.). Protocols for the transformation of yeast and fungi are well known to those of ordinary skill in the art. (see Hinnen et al., PNAS USA 75:1929, 1978; Itoh et al., J. Bacteriology 153:163, 1983, and Cullen et al. (Bio/Technology 5:369, 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., (1987) Nature 329:840) and pMT2PC (Kaufman et al. (1987), EMBO J. 6:187–195).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47–58, 1987, which reviews the use of Agrobacterium rhizogenes vectors; see also Zambryski et al., Genetic Engineering, Principles and Methods, Hollaender and Setlow (eds.), Vol. VI, pp. 253–278, Plenum Press, New York, 1984, which describes the use of expression vectors for plant cells, including, among others, pAS2022, pAS2023, and pAS2034).

Insect cells suitable for carrying out the present invention include cells and cell lines from Bombyx or Spodotera species. Baculovirus vectors available for expression of proteins in cultured insect cells (SF 9 cells) include the pAc series (Smith et al., (1983) Mol. Cell Biol. 3:2156–2165) and the pVL series (Lucklow, V. A., and Summers, M. D., (1989) Virology 170:31–39). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (see Hammer et al. (Nature 315:680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

The present invention also provides proteins comprising an A chain of a ricin-like toxin, a B chain of a ricin-like toxin and a heterologous linker amino acid sequence linking the A and B chains, wherein the linker sequence contains a cleavage recognition site for a retroviral protease, such as an HIV protease or an HTLV protease. Such a protein could be prepared other than by recombinant means, for example by chemical synthesis or by conjugation of A and B chains and a linker sequence isolated and purified from their natural plant, fungal or bacterial source. Such A and B chains could be prepared having the glycosylation pattern of the native ricin-like toxin.

N-terminal or C-terminal fusion proteins comprising the protein of the invention conjugated with other molecules, such as proteins may be prepared by fusing, through recombinant techniques. The resultant fusion proteins contain a protein of the invention fused to the selected protein or marker protein as described herein. The recombinant protein of the invention may also be conjugated to other proteins by known techniques. For example the proteins may be coupled using heterobifunctional thiol-containing linkers as described in WO 90/10457, N-succinimidyl-3-(2-pyridyldithio-proprionate) or N-succinimidyl-5-thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Utility of the Nucleic Acid Molecules and Proteins of the Invention

The proteins of the invention may be used to specifically inhibit or destroy mammalian cancer cells or mammalian cells infected with a retrovirus. It is an advantage of the recombinant proteins of the invention that they have specificity for the infected cells without the need for a cell binding component. The ricin-like B chain of the recombinant proteins recognize galactose moieties on the cell surface and ensure that the protein is taken up by the cell and released into the cytoplasm. When the protein is released into a non-infected cell, the A chain will remain inactive bound to the B chain. However, when the protein is released into a cell infected with a retrovirus or containing an HTLV or HIV protease, the retroviral protease will cleave the cleavage recognition site in the linker, releasing the toxic A chain.

The specificity of a recombinant protein of the invention may be tested by treating the protein with the retroviral protease, such as HIV protease or HTLV protease which is thought to be specific for the cleavage recognition site of the linker and assaying for cleavage products. Retroviral proteases such as HIV protease or HTLV protease may be isolated from infected cells or may be prepared recombinantly, for example following the procedures in Darket et al. (1988, J. Biol. Chem. 254:2307–2312). The cleavage products may be identified for example based on size, antigenicity or activity. The toxicity of the recombinant protein may be investigated by subjecting the cleavage products to an in vitro translation assay in cell lysates, for example using Brome Mosaic Virus mRNA as a template. Toxicity of the cleavage products may be determined using a ribosomal inactivation assay (Westby et al. 1992, Bioconjugate Chem. 3:377–382). The effect of the cleavage products on protein synthesis may be measured in standardized assays of in vitro translation utilizing partially defined cell free systems composed for example of a reticulocyte lysate preparation as a source of ribosomes and various essential cofactors, such as mRNA template and amino acids. Use of radiolabelled amino acids in the mixture allows quantitation of incorporation of free amino acid precursors into trichloroacetic acid precipitable proteins. Rabbit reticulocyte lysates may be conveniently used (O'Hare, FEBS Lett. 1990, 273:200–204).

The ability of the recombinant proteins of the invention to selectively inhibit or destroy mammalian cells infected with a retrovirus such as cancer cells associated with HTLV or cells associated with HIV may be readily tested in vitro using mammalian cell cultures infected with the retrovirus of interest, or cancer lines. The selective inhibitory effect of the recombinant proteins of the invention may be determined by demonstrating the selective inhibition of viral antigen expression in mammalian cells, or selective inhibition of cellular proliferation in cancer cells or infected cells. For example, a selective inhibitory effect may be demonstrated by the selective inhibition of viral antigen expression in HIV-infected mononuclear phagocytic lineage cells; selective inhibition of cellular proliferation as measured against protein and DNA synthesis levels in treated, noninfected T cells and; selective loss of T cell viability. For example, the below-noted culture systems may be used to test the ability of recombinant proteins having a heterlogous linker sequence containing a cleavage recognition site for the HIV protease to selectively inhibit HIV infected cells. The term HIV refers to a CD4+ dependent human immunodeficiency retrovirus, such as HIV-1 and variants thereof.

Normal human T lymphocytes may be prepared from peripheral blood samples and cultured in vitro, as generally described in U.S. Pat. No. 4,869,903. HIV infected cells may also be obtained from AIDS patients. The cells may be infected in vitro with HIV derived from an AIDS patient. The toxicity of the recombinant protein for infected and non-infected cultures may then be compared. HIV-infected T cells express HIV envelope protein on the cell surface, in particular the proteins gp120 and gp41. The ability of the recombinant protein of the invention to inhibit the expression of these viral antigens may be an important indicator of the ability of the protein to inhibit viral replication. Toxicity may be measured based upon cell death or lysis, or by a reduction in the expression of HIV antigens, such as the major envelope proteins gp120 and gp41 or the HIV core protein antigen p24.

Levels of these antigens may be measured in assays using labelled antibodies having specificity for the antigens. Inhibition of viral antigen expression has been correlated with inhibition of viral replication (U.S. Pat. No. 4,869,903). Similar assays may be carried out using other suitable mammalian cells which can be cultured in vitro and which are capable of maintaining retroviral replication. Examples of suitable cells include mononuclear phagocytic lineage cells. Toxicity may also be assessed based on a decrease in protein synthesis in target cells, which may be measured by known techniques, such as incorporation of labelled amino acids, such as [3H] leucine (O'Hare et al. 1990, FEBS Lett. 273:200–204). Infected cells may also be pulsed with radiolabelled thymidine and incorporation of the radioactive label into cellular DNA may be taken as a measure of cellular proliferation.

In the models of viral infection and replication for confirming the activity of the recombinant proteins of the invention, suitable mammalian cells used as hosts are those cells which can be cultured in vitro and which are capable of maintaining viral replication. Examples of suitable cells can be human T lymphocytes or mononuclear phagocytic lineage cells. Normal human T lymphocytes may be prepared from peripheral blood samples and cultured in vitro, as generally described in U.S. Pat. No. 4,869,903. Virally infected cells may also be obtained from the blood of infected patients. The toxicity of the recombinant protein for infected and non-infected cultures may then be compared. The ability of the recombinant protein of the invention to inhibit the expression of these viral antigens may be an important indicator of the ability of the protein to inhibit viral replication. Levels of these antigens may be measured in assays using labelled antibodies having specificity for the antigens. Inhibition of viral antigen expression has been correlated with inhibition of viral replication (U.S. Pat. No. 4,869,903).

Toxicity may also be assessed based on a decrease in protein synthesis in target cells, which may be measured by known techniques, such as incorporation of labelled amino acids, such as [3H] leucine (O'Hare et al. 1990, FEBS Lett. 273:200–204). Infected cells may also be pulsed with radiolabelled thymidine and incorporation of the radioactive label into cellular DNA may be taken as a measure of cellular proliferation. In addition, toxicity may be measured based on cell viability, for example the viability of infected and non-infected cell cultures exposed to the recombinant protein may be compared. Cell viability may be assessed by known techniques, such as trypan blue exclusion assays.

Although, the specificity of the proteins of the invention for retrovirally infected cells is mediated by the specific cleavage of the cleavage recognition site of the linker, it will be appreciated that specific cell binding components may optionally be conjugated to the proteins of the invention. Such cell binding components may be expressed as fusion proteins with the proteins of the invention or the cell binding component may be physically or chemically coupled to the protein component. Examples of suitable cell binding components include antibodies to retroviral proteins, or to cancer cell proteins.

Antibodies having specificity for a cell surface protein may be prepared by conventional methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated.

The term "antibody" as used herein is intended to include fragments thereof which also specifically react with a cell surface component. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a cell surface antigen (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive against cell surface components can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication W092/06193 or EP 0239400). Humanized antibodies can also be commercially produced (Scotgen Limited, 2 Holly Road, Twickenham, Middlesex, Great Britain.) Specific antibodies, or antibody fragments, reactive against cell surface components may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). Alternatively, a SCID-hu mouse, for example the model developed by Genpharm, can be used to produce antibodies, or fragments thereof.

The proteins of the invention may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The pharmaceutical compositions may be used in methods for treating mammals, including humans, infected with a retrovirus. It is anticipated that the compositions will be particularly useful for treating patients infected with HIV-1, HIV-2 or cancers involving retroviruses, such as human T-cell leukemias involving HTLV. The efficacy of such treatments may be monitored by assessing the health of the patient treated and by measuring the percentage of HIV positive monocytes in treated patients.

The dose of the recombinant protein to be administered will depend on a variety of factors which may be readily monitored in human subjects. Such factors include HIV antigen levels associated with HIV infected T cells or mononuclear phagocytes; HIV antigen levels in the bloodstream; reverse transcriptase activity associated with HIV-infected T cells or mononuclear phagocytes; and the ratio of viable HIV infected cells to uninfected cells. HIV antigen levels in plasma, for example, may be readily determined using an ELISA assay.

The following non-limiting examples are illustrative of the present invention:

EXAMPLES

Example 1

Cloning and Expression of Proricin Variants Activated by HIV Proteases
Isolation of Total RNA
The preproricin gene was cloned from new foliage of the castor bean plant. Total messenger RNA was isolated according to established procedures (Maniatis et al., *Molecular Cloning: A Lab Manual* (Cold Spring Harbour Press, Cold Spring Harbour, (1989)) and cDNA generated using reverse transcriptase.

cDNA Synthesis
Oligonucleotides, corresponding to the extreme 5' and 3' ends of the preproricin gene were synthesized and used to PCR amplify the gene. Using the cDNA sequence for preproricin (Lamb et al., Eur. J. Biochem., 145:266–270, 1985), several oligonucleotide primers were designed to flank the start and stop codons of the preproricin open reading frame. The oligonucleotides were synthesized using an Applied Biosystems Model 392 DNA/RNA Synthesizer. First strand cDNA synthesis was primed using the oligonucleotide Ricin1729C (Table 1). Three micrograms of total RNA was used as a template for oligo Ricin1729C primed synthesis of cDNA using Superscript II Reverse Transcriptase (BRL) following the manufacturer's protocol.

DNA Amplification and Cloning
The first strand cDNA synthesis reaction was used as template for DNA amplification by the polymerase chain reaction (PCR). The preproricin cDNA was amplified using the upstream primer Ricin-99 and the downstream primer Ricin1729C with Vent DNA polymerase (New England Biolabs) using standard procedures (Sambrook et al., Molecular Cloning: A Laboratory Manual, Second Edition, (Cold Spring Harbor Laboratory Press, 1989)). Amplification was carried out in a Biometra thermal cycler (TRIO-Thermalcycler) using the following cycling parameters: denaturation 95° C. for 1 min., annealing 52° C. for 1 min., and extension 72° C. for 2 min., (33 cycles), followed by a final extension cycle at 72° C. for 10 min. The 1846bp amplified product was fractionated on an agarose gel (Sambrook et al., Molecular Cloning: A Laboratory Manual, Second Edition, (Cold Spring Harbor Laboratory Press, 1989), and the DNA purified from the gel slice using Qiaex resin (Qiagen) following the manufacturer's protocol. The purified PCR fragment encoding the preproricin cDNA was then ligated (Sambrook et al., Molecular Cloning: A Laboratory Manual, Second Edition, (Cold Spring Harbor Laboratory Press, 1989)) into an Eco RV-digested pBluescript II SK plasmid (Stratagene), and used to transform competent XL1-Blue cells (Stratagene). Positive clones were confirmed by restriction digestion of purified plasmid DNA. Plasmid DNA was extracted using a Qiaprep Spin Plasmid Miniprep Kit (Qiagen).

DNA Sequencing
The cloned PCR product containing the putative preproricin gene was confirmed by DNA sequencing of the entire cDNA clone (pAP-144). Sequencing was performed using an Applied Biosystems 373A Automated DNA Sequencer, and confirmed by double-stranded dideoxy sequencing by the Sanger method using the Sequenase kit (USB). The oligonucleotide primers used for sequencing were as follows: Ricin267, Ricin486, Ricin725, Ricin937, Ricin1151, Ricin1399, Ricin1627, T3 primer (5'AATTAACCCTCACTAAAGGG-3') (SEQ ID NO: 59)and T7 primer (5'GTAATACGACTCACTATAGGGC-3) (SEQ ID NO: 60). Sequence data was compiled and analyzed using PC Gene software package (intelligenetics). The sequences and location of oligonucleotide primers is shown in Table 1.

Mutagenesis of Preproricin Linker
The preproricin cDNA clone (pAP-144) was subjected to site-directed mutagenesis in order to generate a series of variants differing only in the sequence between the A and B chains (linker region). The wild-type preproricin linker region (SEQ ID NO: 19)was replaced with the three linker sequences, pAP-146 (SEQ ID NO:20), pAP-147 (SEQ ID NO:20)and pAP-148 (SEQ ID NO:22) displayed in FIG. 4. The linker regions of the variants encode an HIV protease cleavage recognition sequence (Slalka et al., Cell, 56:911–913, 1989). The mutagenesis and cloning strategy used to generate the linker variant pAP-146 is summarized in FIGS. 1A and 1B (SEQ ID NOS:1–6). The mutagenesis and cloning strategy used to generate the linker variant pAP-147 is summarized in FIGS. 2A and 2B (SEQ ID NOS: 7–12). The mutagenesis and cloning strategy used to generate the linker variant pAP-148 is summarized in FIGS. 3A and 3B (SEQ ID NOS: 13–18). The first step involved a DNA amplification using a set of mutagenic primers (HIVA1; HIVB1; HIVH1) in combination with the two flanking primers Ricin-99Eco and Ricin1729Xba. The PCR protocol and conditions used were the same as described above. PCR products from each mutagenesis reaction were gel purified then restriction digested with either Eco RI for the A-chain encoding fragment, or Xba I for the B chain encoding fragment. Restriction digested PCR fragments were gel purified and then ligated with PBluescript SK which had been digested with Eco RI and Xba I. Ligation reactions were used to transform competent XL1-Blue cells (Stratagene). Recombinant clones were identified by restriction digests of plasmid miniprep DNA and the mutant linker sequence were confirmed by DNA sequencing.

Subcloning Preproricin Mutants into Vector pSB2

Figure 12:
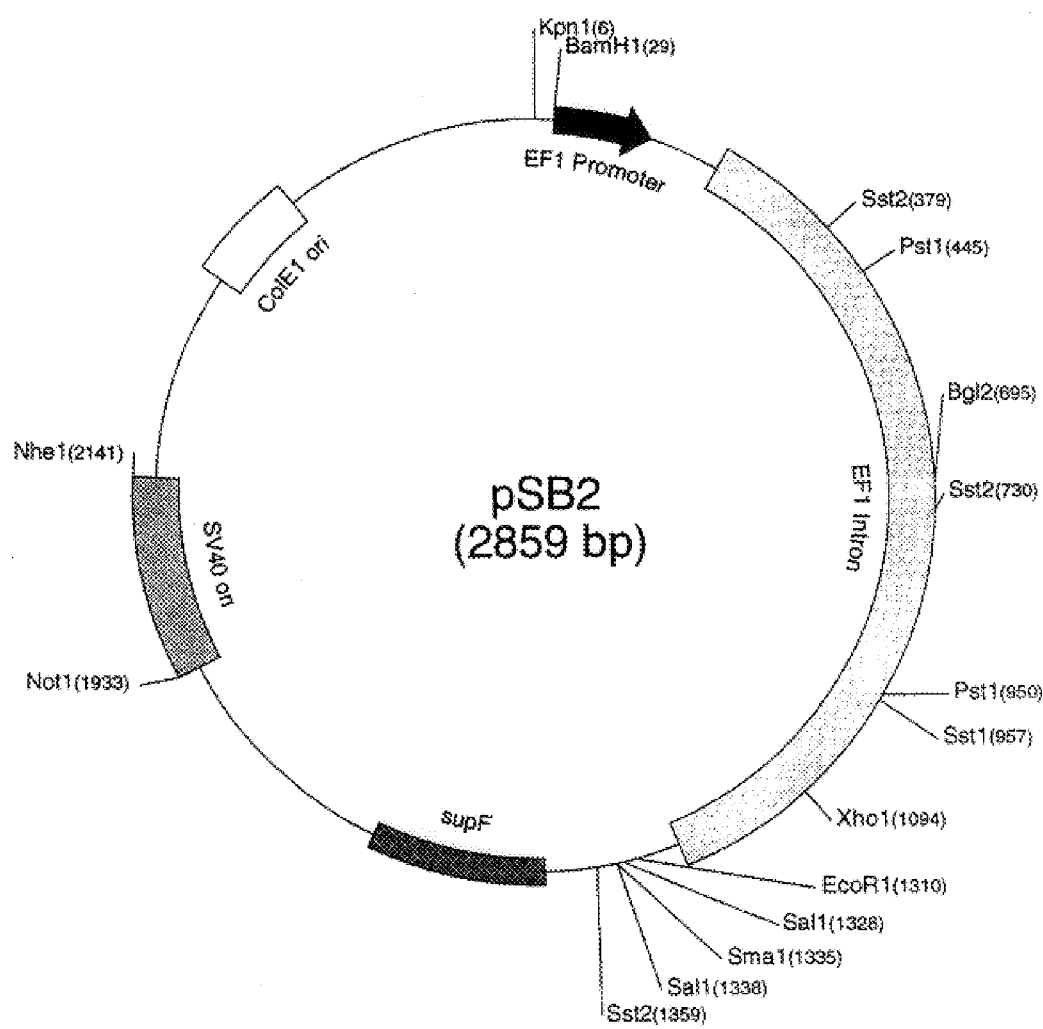
FIG. 12 is a diagram of the vector pSB2.

Full length preproricin cDNA was created from clones pAP-146, pAP-147, and pAP-148, which lack the first three nucleotides of the signal sequence (Halling et al, Nucleic Acids Research, 13:8019–8033, 1985). The missing ATG (start codon) was introduced into each mutant by site-directed mutagenesis using primers Ricin-109 and Ricin1729C. The DNA template for each reaction was pAP-146, pAP-147, or pAP-148, and the PCR conditions were the same as described above. PCR products were gel purified and then ligated with Sma I-digested pSB2 (see FIG. 12). Recombinant clones were identified by restriction digests of plasmid miniprep DNA, and the 5' and 3' junctions confirmed by DNA sequencing. The three constructs obtained were pAP-151, pAP-159, and pAP-163, with each having the mutant linker found in pAP-146, pAP-147, and pAP-148 respectively.

Subcloning Preproricin Mutants Into Vector pVL1393

Figure 6:
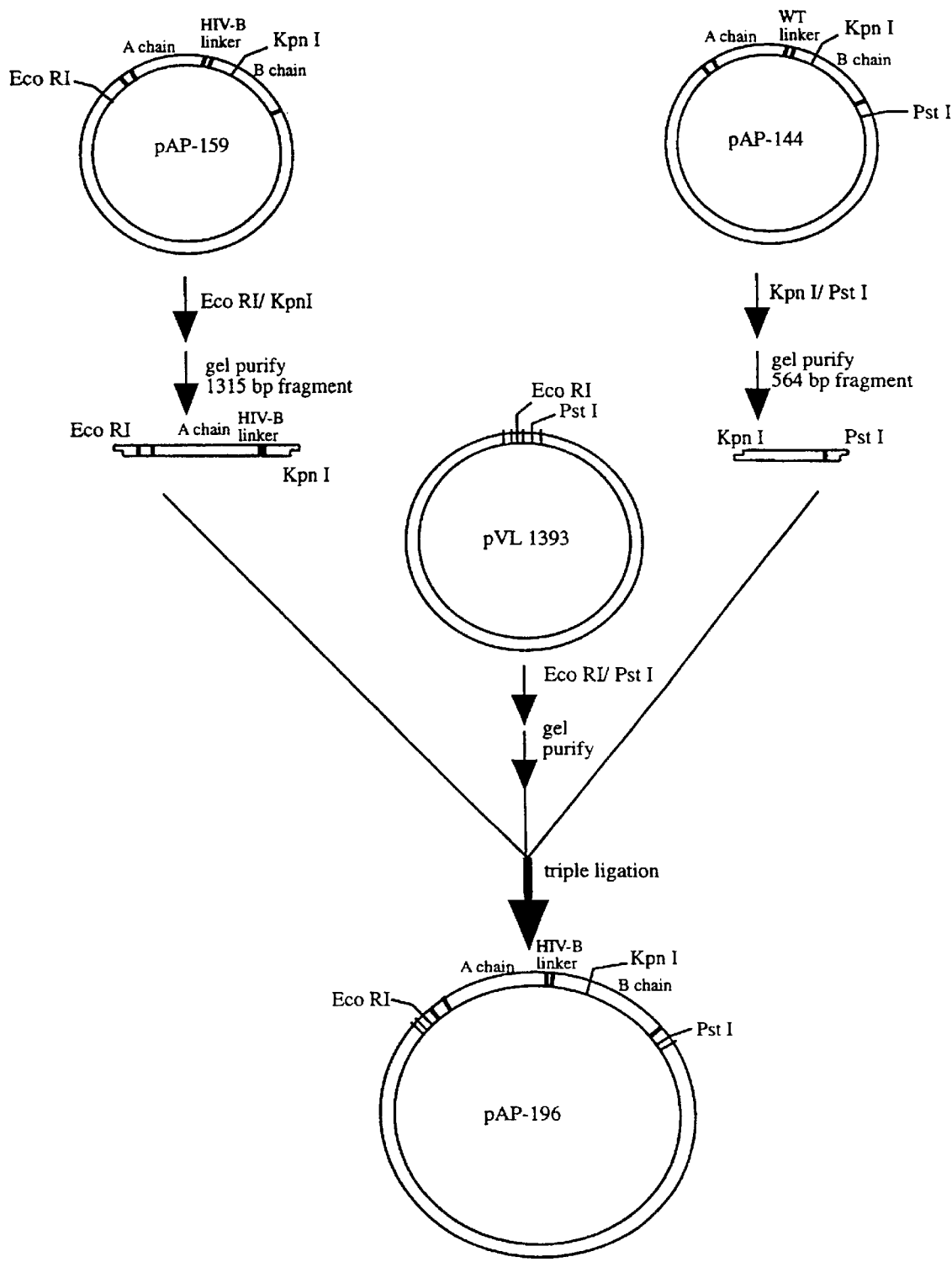
FIG. 6 shows the subcloning of the HIV-B linker variant into a baculovirus transfer vector.
Figure 7:
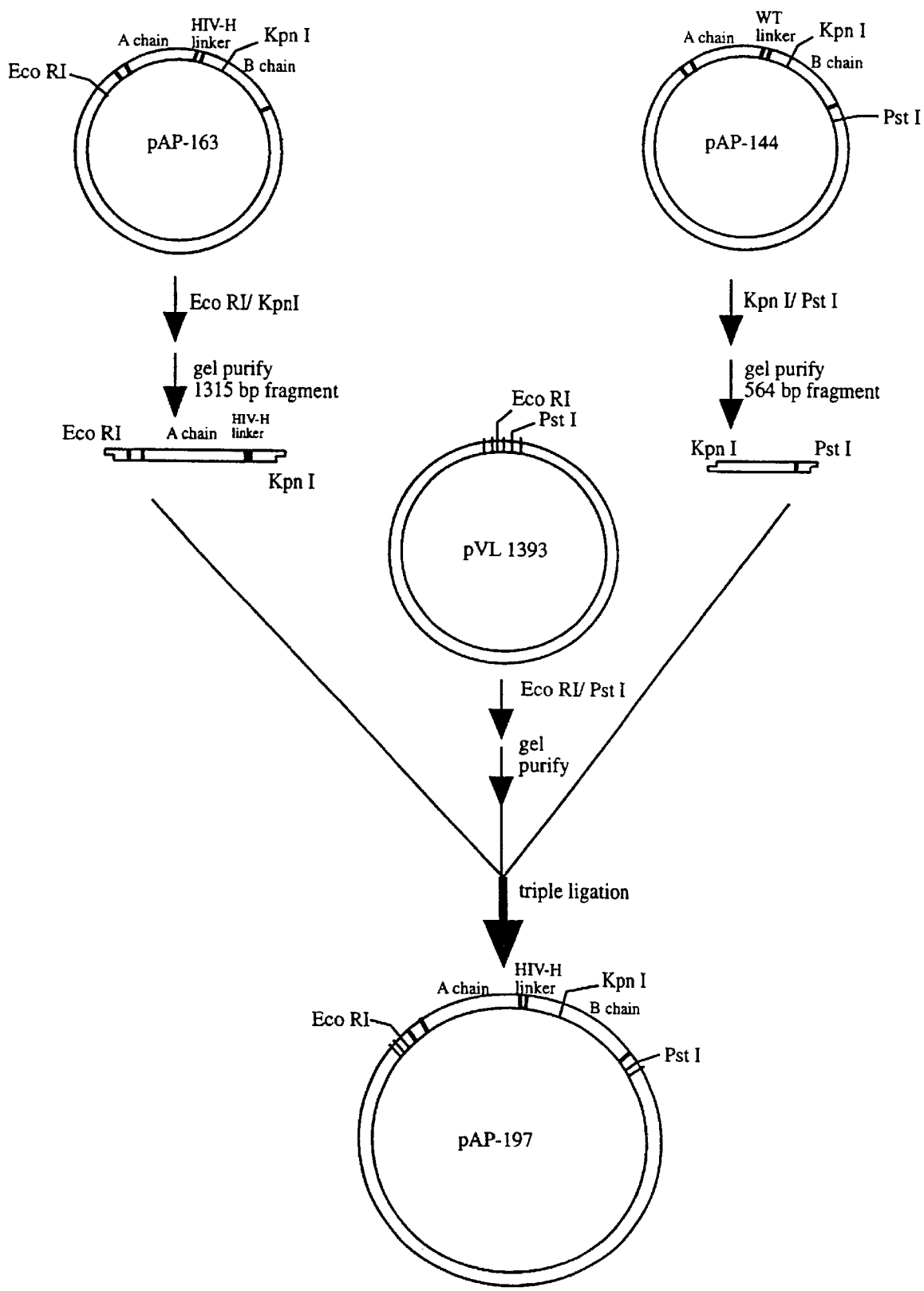
FIG. 7 shows the subcloning of the HIV-H linker variant into a baculovirus transfer vector.

Preproricin variants were subcloned into the baculovirus transfer vector pVL1393 (PharMingen, sequence shown in FIG. 11 (SEQ ID NO:26)). The subcloning strategy for the HIV-A linker variant is summarized in FIG. 5. The subcloning strategy for the HIV-B linker variant is summarized in FIG. 6. The subcloning strategy for the HIV-H linker variant is summarized in FIG. 7. The 1315 bp Eco RI/Kpn I fragment encoding the ricin A-chain and each mutant linker was isolated from each of the variant clones in pSB2 (pAP-151, pAP-159, and pAP-163). Each of these purified fragments was ligated with a 564 bp KpnI/PStI fragment obtained from pAP-144, and with Eco RI/Pst I cleaved pVL1393. Recombinant clones were identified by restriction digests of plasmid miniprep DNA and the 5' and 3' junctions confirmed by DNA sequencing. The three constructs obtained were pAP-190, pAP-196, and pAP-197, each having the mutant linker found in pAP-146, pAP-147, and pAP-148, respectively.

Isolation of Recombinant Baculoviruses

Insect cells *S. frugiperda* (Sf9), and *Trichoplusia ni* (Tn368 and BTI-TN-581-4 (High Five)) were maintained on TMN-FH medium supplemented with 10% total calf serum (Summers et al., A Manual of Methods of Baculovirus Vectors and Insect Cell Culture Procedures, (Texas Agricultural Experiment Station, 1987)). Two micrograms of recombinant pVL1393 DNA (pAP-190, pAP-196, or pAP-197) was co-transfected with 0.5 microgram of BaculoGold AcNPV DNA (Pharmingen) into $2 \times 10^6$ Tn368 insect cells following the manufacturer's protocol (Gruenwald et al., Baculovirus Expression Vector System: Procedures and Methods Manual, 2nd Edition, (San Diego, Calif., 1993)). On day 5 post-transfection, media were centrifuged and the supernatants tested in limiting dilution assays with Tn368 cells (Summers et al., A Manual of Methods of Baculovirus Vectors and Insect Cell Culture Procedures, (Texas Agricultural Experiment Station, 1987)). Recombinant viruses in the supernatants were then amplified by infecting Tn368 cells at a multiplicity of infection (moi) of 0.1, followed by collection of day 7 supernatants. A total of three rounds of amplification were performed for each recombinant following established procedures (Summers et al., A Manual of Methods of Baculovirus Vectors and Insect Cell Culture Procedures, (Texas Agricultural Experiment Station, 1987 and Gruenwald et al., Baculovirus Expression Vector System: Procedures and Methods Manual, 2nd Edition, (San Diego, Calif., 1993)).

Expression of Mutant Proricin

Recombinant baculoviruses (pAP-190baculo, pAP-196baculo, and pAP-197-baculo) were used to infect $2 \times 10^5$ Tn368 or sf9 cells of an moi of 5 in EX-CELL400 media (JRH Biosciences) with 25 mM α-lactose in spinner flasks. Media supernatants containing mutant proricins were collected on day 6 post-infection.

Purification of Mutant Proricin

Media supernatants were ultracentrifuged at 100,000 g for 1 hour. After the addition of 1 mM phenylmethylsulfonyl fluoride, the supernatants were concentrated using an Amicon 8050 Ultrafiltration Cell fitted with a Diaflo XM50 membrane. Supernatants were then dialysed extensively against 137 mN NaCl, 2.2 mM KCl, 2.6 mM $KH_2PO_4$, and 8.6 mM $Na_2HPO_4$, pH 7.4 containing 1 mM dithiothreitol (dialysis buffer). Recombinant proricin proteins were purified by affinity chromatography using lactose agarose (Sigma) as previously described for recombinant ricin-β chain (Ferrini et al., Eur. J. Biochem., 233:772–777, 1995). Fractions containing recombinant proricin were identified using SDS/PAGE, (Sambrook et al., Molecular Cloning: A Laboratory Manual, Second Edition, (Cold Spring Harbor Laboratory Press, 1989) and by Western blot analysis using anti-ricin antibodies (Sigma).

In Vitro HIV Protease Digestion of Proricin Variants

Affinity-purified mutant proricin was treated with HIV protease to confirm specific cleavage in the linker region. Proricin variants were eluted from the lactose-agarose matrix in protease digestion buffer (50 mM NaCl, 50 mM Na-acetate, pH 5.5, 1 mM dithiothreitol) containing 100 mM lactose. Proricin substrate was then incubated at 37° C. for 60 minutes with 400 ng/ml recombinant HIV protease (BACHEM Biosciences Inc.). The cleavage products of proricin (ricin A and B chains) were identified using SDS/PAGE (Sambrook et al., *Molecular Cloning: a Laboratory Manual,* 2nd. ed., Cold Spring Harbor Press, 1989), followed by Western blot analysis using anti-ricin antibodies (Sigma).

In Vitro Translation Assay

The activity of protease-treated proricin variants was monitored using a rabbit reticulocyte lysate in a non-radioactive (Amersham, ECL system) in vitro translation assay. Protease-treated proricin was added to a standard 50

µl translation reaction mix containing Brome Mosaic Virus mRNA as template (following the manufacturer's protocol). Active ricin variants inhibit the in vitro translation reaction by inactivating ribosomes. Therefore, in the presence of an active ricin variant, no viral proteins are synthesized.

Example 2

Harvesting and Affinity Column Purification of Pro-ricin Variants

Protein samples were harvested three days post transfection. The cells were removed by centrifuging the media at 1465 g for ten minutes using a SLA-1500 (Sorvall) centrifuge rotor. The supernatant was further clarified by centrifuging at 7970 g for fifteen minutes. Protease inhibitor phenylmethyl-sulfonyl fluoride (Sigma) was added to a final concentration of 1%. The samples were concentrated (five-fold) and dialyzed (four times five-fold) into dialysis buffer (1×baculo buffer (8.6 mM $Na_2HPO_4$, 2.6 mM $KH_2PO_4$, 137 mM naCl and 2.6 mM KCl, pH 7.4) containing 2.5 mM lactose, and 0.02% $NaN_3$) using a MINITAN concentrator (Millipore) with 30 kDa NMWL plates. Dithiothreitol (DTT) was then added to a final concentration of 1 mM, and the samples were centrifuged at 37000 g for one hour.

Following centrifugation, dialysis buffer containing 1 mM DTT was added to the samples to a final volume of 500 mL. The samples were degassed and applied overnight at 4° C. to an ASF-sepharose affinity column (prepared according to Pharmacia protocol) in a 10 mL chromatography column (Biorad). The column was washed with 300 mL of wash buffer (100 mM NaOAc, pH 5.2, 1 mM DTT, and 0.02% $NaN_3$). Elution of pro-ricin variant was performed by applying 500 mL of elution buffer (100 mM NaOAc, pH 5.2, 250 mM lactose, and 5 mM DTT). The eluate was concentrated using an Amicon 8050 concentrator (Amicon) with a YM10 176 mm membrane, utilizing argon gas to pressurize the chamber. The samples were further concentrated and dialyzed into 1×Baculo buffer using Ultrafree-15 Biomax (Millipore) 10 kDa NMWL filter devices, which were spun in a Beckman S4180 rotor (Beckman) at 2000 g. Samples were flash frozen in dry ice and stored at −20° C.

Purification of pAP 190 by Gel Filtration Chromatography

In order to purify the pro-ricin variant from processed material produced during fermentation, the protein was applied to a SUPERDEX 75 (16/60) column and SUPERDEX 200 (16/60) column (Pharmacia) connected in series equilibrated with 50 mM Tris, 100 mM NaCl, pH 7.5 containing 100 mM Lactose and 0.1% β-mercaptoethanol (βME). The flow rate of the column was 0.15 mL/min and fractions were collected every 25 minutes. The UV (280 nm) trace was used to determine the approximate location of the purified pAP 190 and thus determine the samples for Western analysis.

Western Analysis of Column Fractions

Fractions eluted from the SUPERDEX columns (Pharmacia) were analyzed for purity using standard Western blotting techniques. An aliquot of 10 µL from each fraction was boiled in 1×sample buffer (62.6 mM Tris-Cl, pH 6.8, 4.4% βME, 2% sodium dodecyl sulfate (SDS), 5% glycerol (all from Sigma) and 0.002% bromophenol blue (Biorad)) for five minutes. Denatured samples were loaded on 12% Tris-Glycine Gels (Biorad) along with 50 ng of $RCA_{60}$ (Sigma) and 5 µL of kaleidoscope prestained standards (Biorad). Electrophoresis was carried out for ninety minutes at 100V in 25 mM Tris-Cl, pH 8.3, 0.1% SDS, and 192 mM glycine using the BioRad Mini Protean II cells (Biorad).

Following electrophoresis gels were equilibrated in transfer buffer (48 mM Tris, 39 mM glycine, 0.0375% SDS, and 20% Methanol) for a few minutes. PVDF Biorad membrane was presoaked for one minute in 100% methanol and two minutes in transfer buffer. Whatman paper was soaked briefly in transfer buffer. Five pieces of Whatman paper, membrane, gel, and another five pieces of Whatman paper were arranged on the bottom cathode (anode) of the Pharmacia Novablot transfer apparatus (Pharmacia). Transfer was for one hour at constant current (2 mA/cm$^2$).

Transfer was confirmed by checking for the appearance of the prestained standards on the membrane. Non-specific sites on the membrane were blocked by incubating the blot for thirty minutes in 1×Phosphate Buffered Saline (1×PBS; 137 mM NaCl, 2.7 mM KCl, 8 mM $Na_2HPO_4$, 1.5 mM $KH_2PO_4$, pH 7.4) with 5% skim milk powder (Carnation). Primary antibody (Rabbit α-ricin, Sigma) was diluted 1:3000 in 1×PBS containing 0.1% Tween 20 (Sigma) and 2.5% skim milk and incubated with blot for forty five minutes on a orbital shaker (VWR). Non-specifically bound primary antibody was removed by washing the blot for ten minutes with 1×PBS containing 0.2% Tween 20. This was repeated four times. Secondary antibody donkey anti-rabbit (Amersham) was incubated with the blot under the same conditions as the primary antibody. Excess secondary antibody was washed as described above. Blots were developed with the ECL Western Blotting detection reagents according to the manufacturer's instructions. Blots were exposed to Medtec's Full Speed Blue Film (Medtee) or Amersham's ECL Hyperfilm (Amersham) for three to fifteen minutes. Film was developed in a KODAK Automatic Developer.

Determination of Lectin Binding Ability of Pro-ricin Variant

An Immulon 2 place (VDVR) was coated with 100 µl per well of 10 µg/ml of asialofetuin and left overnight at 4° C. The plate was washed with 3×300 µL per well with dd$H_2O$ using an automated plate washer (BioRad). The plate was blocked for one hour at 37° C. by adding 300 µL per well of PBS containing 1% ovalbumin. The plate was washed again as above. Pro-ricin variant pAP 190 was added to the plate in various dilutions in 1×Baculo. A standard curve of $RCA_{60}$ (Sigma) from 1–10 ng was also included. The plate was incubated for 1 h at 37° C. The plate was washed as above. Anti-ricin monoclonal antibody (Sigma) was diluted 1:3000 in 1×PBS containing 0.5% ovalbumin and 0.1% tween-20, added at 100 µL per well and incubated for 1 h at 37° C. The plate was washed as above. Donkey-anti rabbity polyclonal antibody was diluted 1:3000 in 1×PBS containing 0.5% ovalbumin, 0.1% Tween-20, and added at 100 µL per well and incubated for 1 h at 37° C. The plate was given a final wash as described above. Substrate was added to plate at 100 µL per well (1 mg/ml o-phenylenediamine (Sigma), 1 µL/ml $H_2O_2$, 25 µL of stop solution (20% $H_2SO_4$) was added and the absorbance read (A490 nm-A630 nm) using a SPECTRA MAX 340 plate reader (Molecular Devices).

Determination of pAP 190 Activity Using the Rabbit Reticulocyte Assay

Ricin sample were prepared for reduction.

A) $RCA_{60}$=3,500 ng/µL of $RCA_{60}$+997 µL 1×Endo buffer
   (25 mM Tris,
   25 mM KCl, 5 mM $MGCl_2$, pH 7.6)
   Reduction=95 µL of 10 ng/µL+5 µL β-mercaptoethanol B) Ricin variants
   Reduction=40 µL variant+2 µL β-mercaptoethanol
   The ricin standard and the variants were incubated for 30 minutes at room temperature.

Ricin—Rabbit Reticulocyte Lysate Reaction

The required number of 0.5 mL tubes were labelled. (2 tubes for each sample, + and − animline). To each of the sample tubes 20 µL of 1×endo buffer was added, and 30 µL of buffer was added to the controls. To the sample tubes either 10 μL of 10 ng/μL Ricin or 10 μL of variant was added. Finally, 30 μL of rabbit reticulocyte lysate was added to all the tubes. The samples were incubated for 30 minutes at 30° C. using the thermal block. Samples were removed from the eppendorf tube and contents added into a 1.5 mL tube containing 1 mL of TRIZOL (Gibco). Samples were incubated for 15 minutes at room temperature. After the incubation, 200 μL of chloroform was added, and the sample was vortexed and spun at 12,000 g for 15 minutes at 4° C. The top aqueous layer from the samples was removed and contents added to a 1 mL tube containing 500 μL of isopropanol. Samples were incubated for 15 minutes at room temperature and then centrifuged at 12,000 for 15 minutes at 4° C. Supernatant was removed and the pellets were washed with 1 mL of 70% ethanol. Centrifugation at 12,000 g for 5 minutes at 4° C. precipitated the RNA. All but approximately 20 μL of the supernatant was removed and the remaining liquid evaporated using the speed vacuum machine. The control samples (–aniline) were dissolved in 10 μL of 0.1×E buffer (36 mM Tris, 30 mM $NaH_2PO_4$, 1 mM EDTA, pH 7.8) and stored at –70° C. or on dry ice until later. Pellets from the other samples (+aniline samples) were dissolved in 20 μL of DEPC treated dd$H_2O$. An 80 μL aliquot of 1 M aniline (distilled) with 2.8 M acetic acid was added to these RNA samples and transferred to a fresh 0.5 mL tube. The samples were incubated in the dark for 3 minutes at 60° C. RNA was precipitated by adding 100 μL of 95% ethanol and 5μL of 3M sodium acetate, pH 5.2 to each tube and centrifuging at 12,000 g for 30 minutes at 4° C. Pellets were washed with 1 mL 70% ethanol and centrifuged again at 12,000 g for 5 minutes at 4° C. to precipitate RNA. The supernatant was removed and excess liquid evaporated using the speed vacuum machine. These pellets (+ aniline samples) were dissolved in 10 μL of 0.1×E buffer. To all samples (+ and – aniline), 10 μL of formamide loading dye was added. The RNA ladder (8 μL of ladder+8 μL of loading dye) was also included. Samples were incubated for 2 minutes at 70° C. on the thermal block. Electrophoresis was carried out on the samples using 1.2% agarose, 50% formamide gels in 0.1×E buffer+0.2% SDS. The gel was run for 90 minutes at 75 watts. RNA was visualized by staining the gel in 1 μg/μL ethidium bromide in running buffer for 45 minutes. The gel was examined on a 302 nm UV box and photographed using the gel documentation system.
Results
Protein Expression Yields Aliquots were taken at each stop of the harvesting/purification and tested. Yields of functional ricin variant were determined by ELISA. Typical results on an 800 mL prep of infected *T. ni* cells are given below,

| Aliquot | μg pAP 190 |
|---|---|
| Before concentration and dialysis | 648.5 |
| After concentration and dialysis | 364.4 |
| ASF column flow through | 62.1 |
| ASF column elution | 300.7 |

Yield: 300.7/648.5=46.4%
Purification of pAP 190 and Western Analysis of Column Fractions Partially purfied pAP 190 was applied to Superdex 75 and 200 (16/60) columns connected in series in order to remove the contaminating non-specifically processed pAP 190. Eluted fractions were tested via Western analysis and the fractions containing the most pure protein were pooled, concentrated and re-applied to the column. The variant was applied a total of three times to the column. The final purified pAP 190 has less than 1% processed variant. FIG. 13 shows that the purified pAP 190 is in three fractions and the processed material eluted in two separate fractions.

Figure 14:
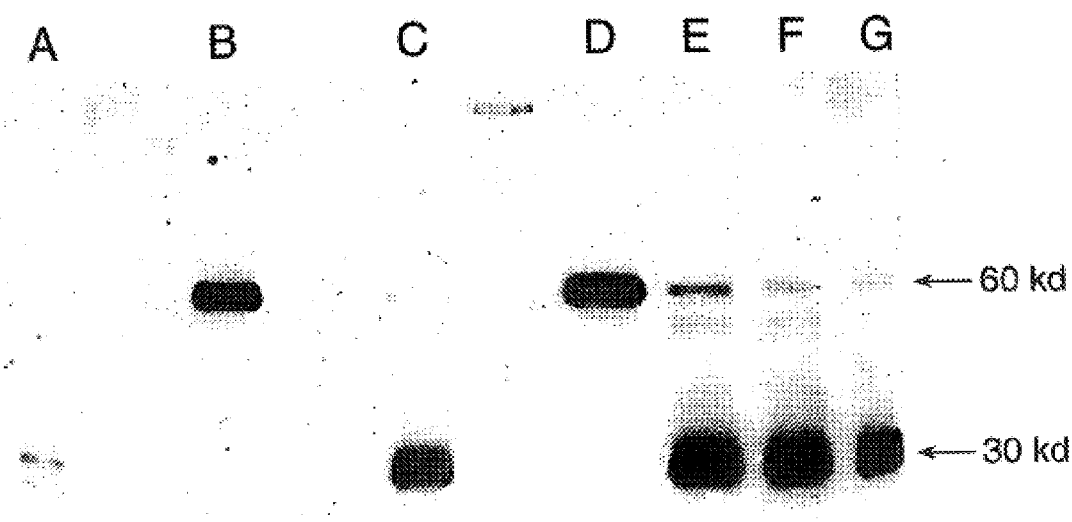
FIG. 14 is a blot showing cleavage of a pAp 190 proricin variant by HIV protease.
Figure 15:
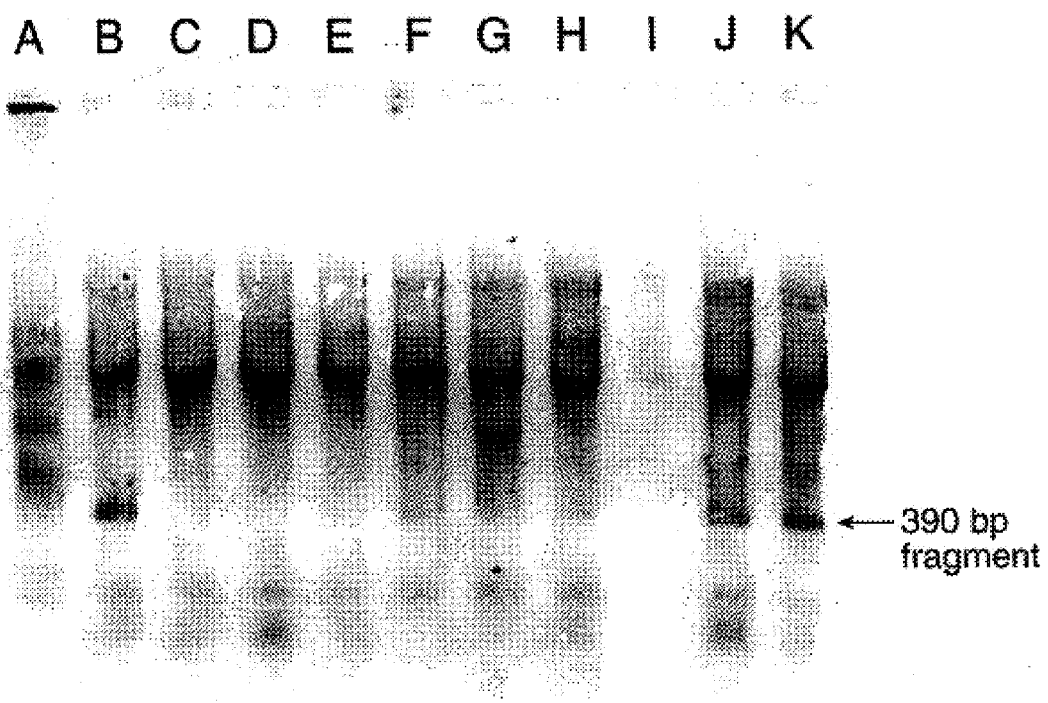
FIG. 15 is a blot showing activation of pAP-190 proricin variant by HIV protease.
Figure 16A:
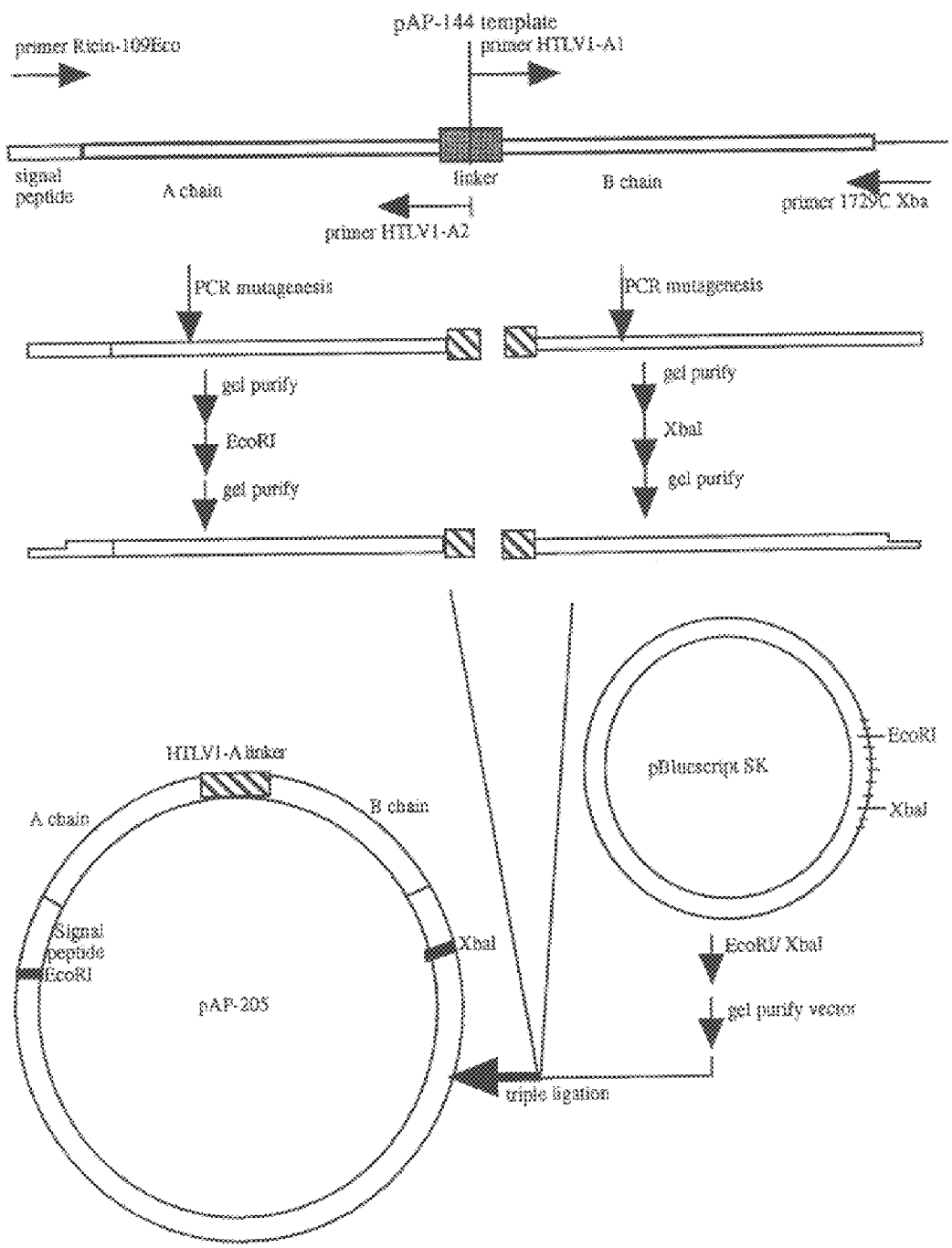
FIG. 16A is a diagram summarizing the cloning strategy used to generate the pAP-205 construct.
Figure 16C:
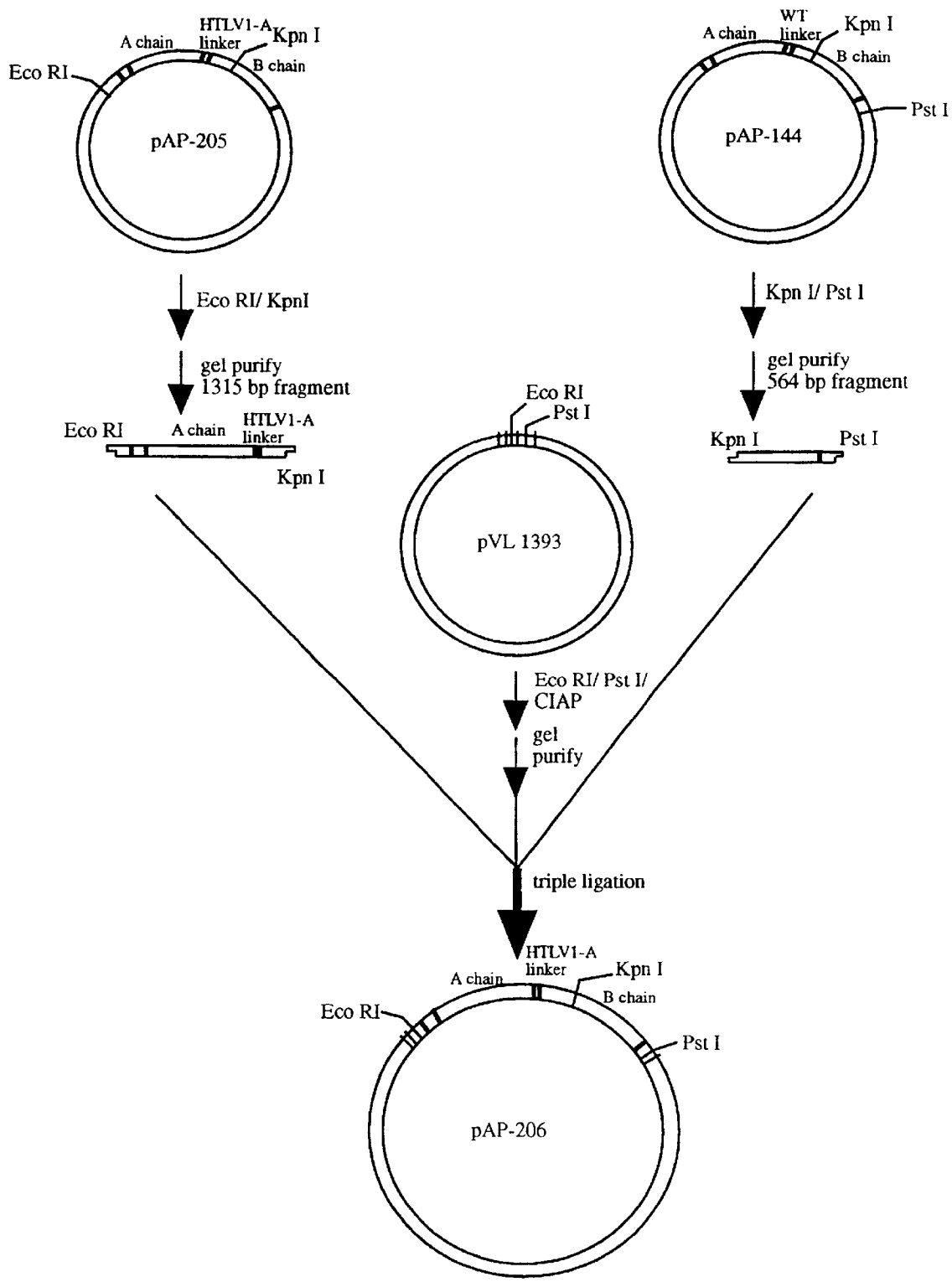
FIG. 16C is a diagram showing the subcloning of the HTLV-I-A linker variant into a baculovirus transfer vector.
Figure 17A:
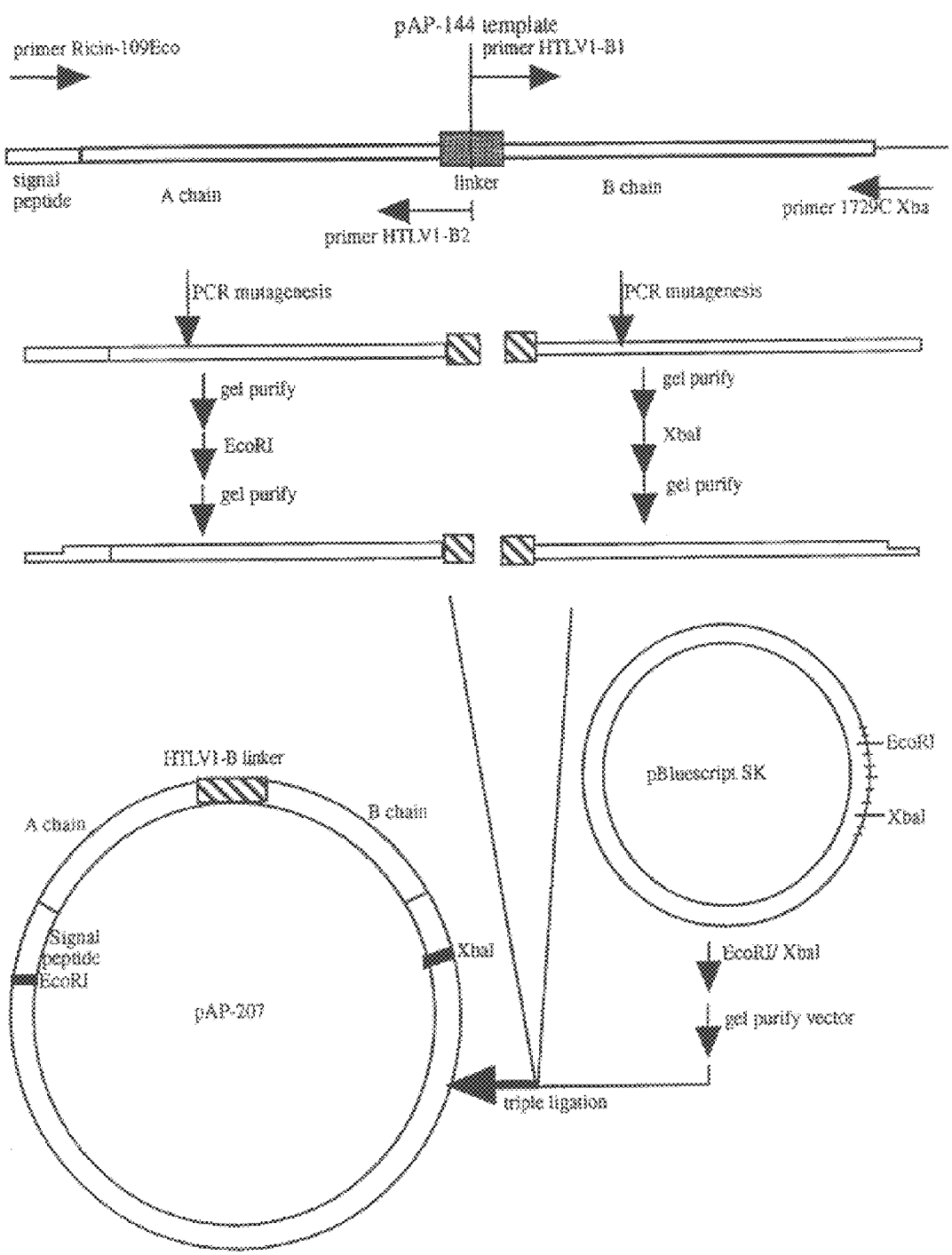
FIG. 17A is a diagram summarizing the cloning strategy used to generate the pAP-207 construct.
Figure 17C:
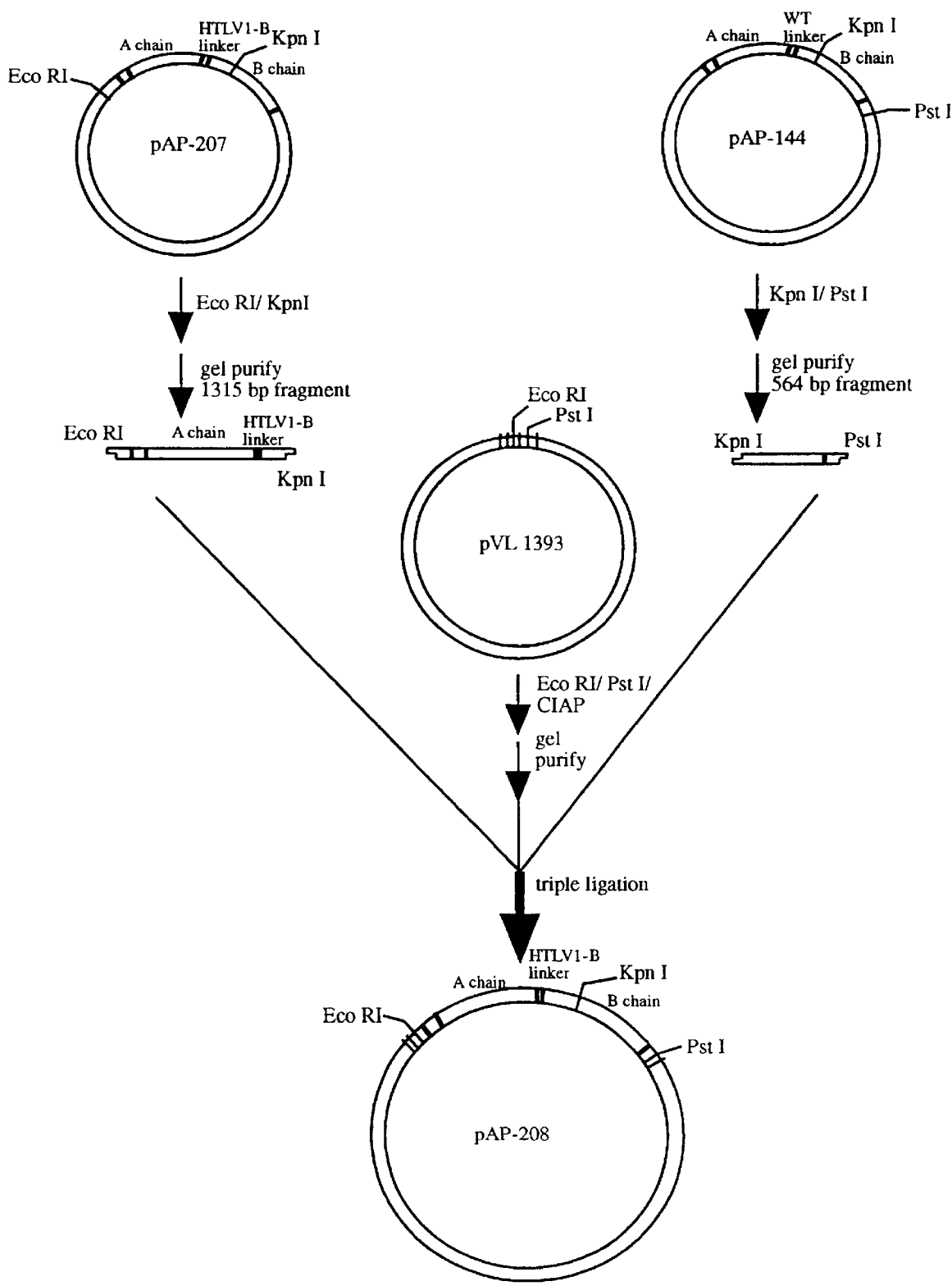
FIG. 17C is a diagram summarizing the subcloning of the HTLV-I-B linker variant into a baculovirus transfer vector.
Figure 18A:
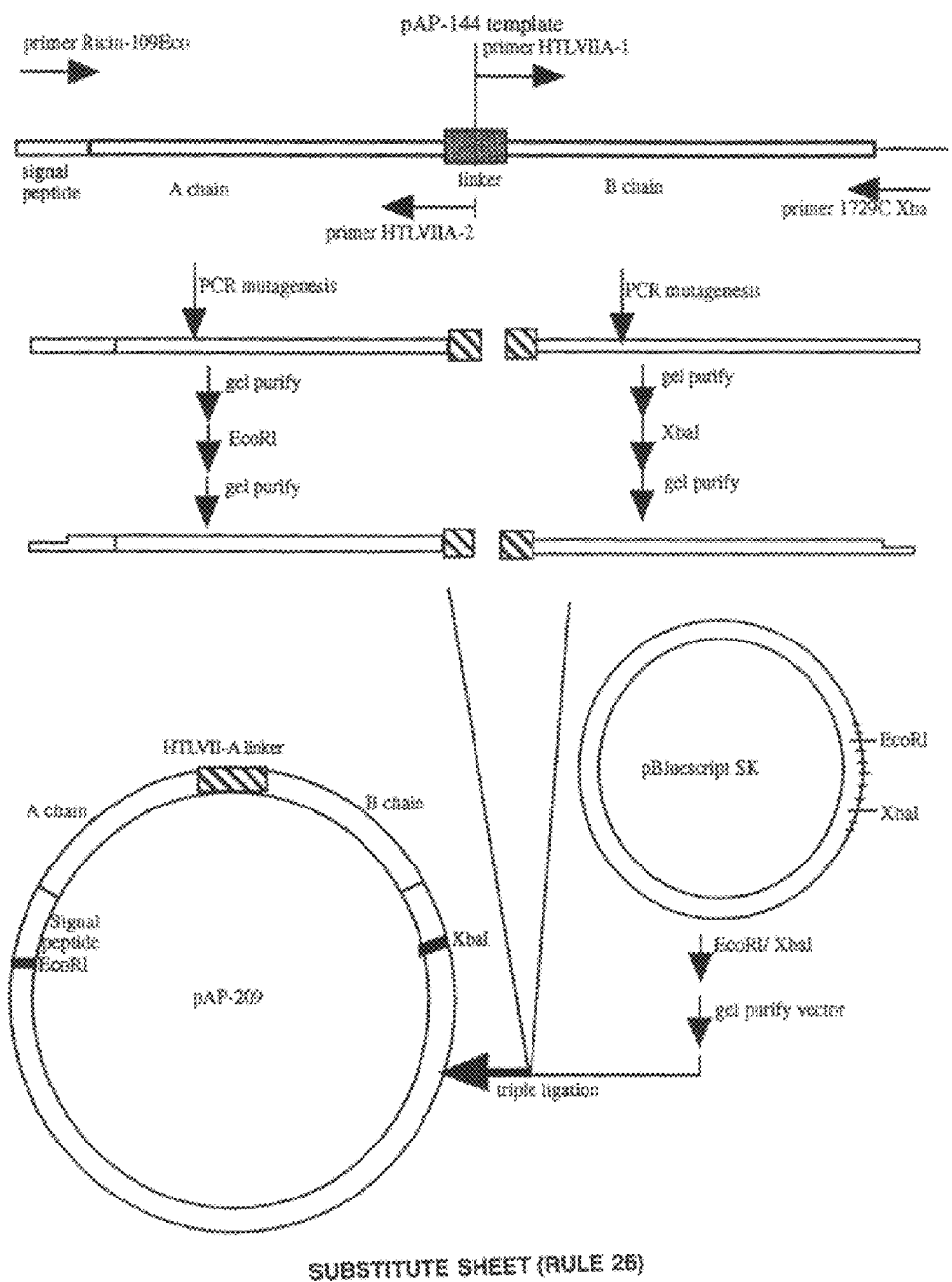
FIG. 18A is a diagram summarizing the cloning strategy used to generate the pAP-209construct.
Figure 18C:
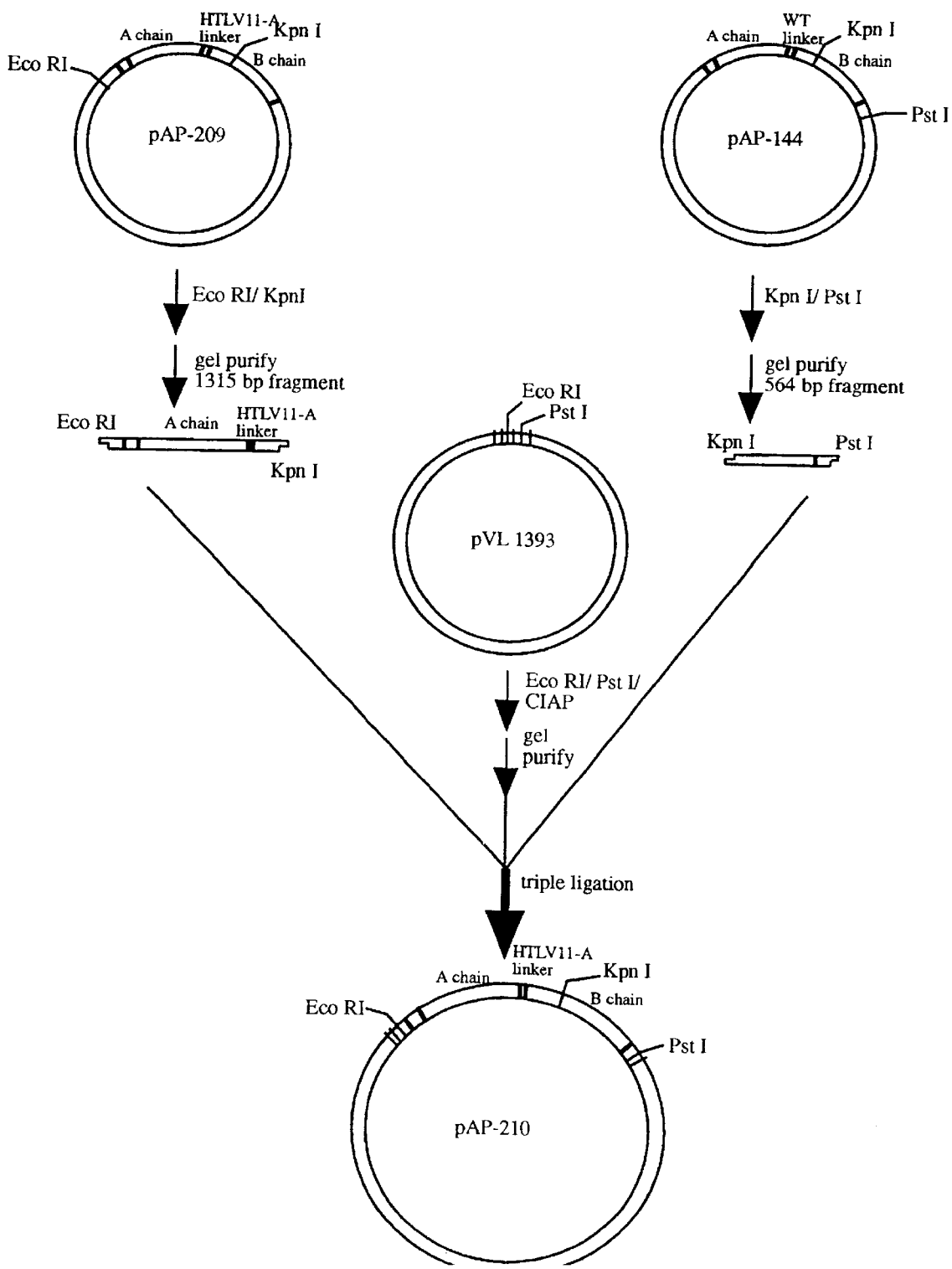
FIG. 18C is a diagram summarizing the subcloning of the HTLV-II-A linker variant into a baculovirus transfer vector.
Figure 19C:
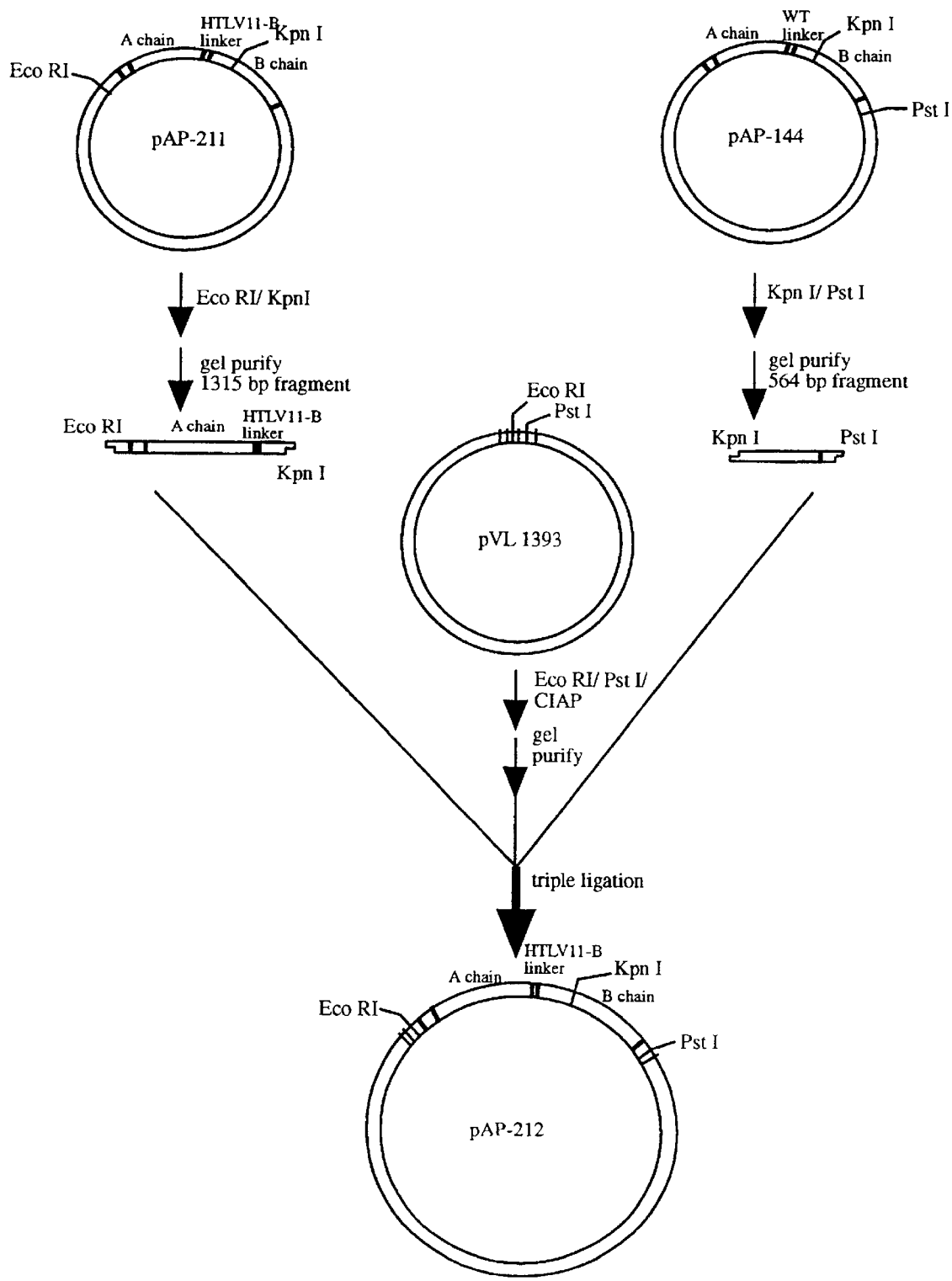
FIG. 19C is a diagram summarizing the subcloning of the HTLV-II-B linker variant into a baculovirus transfer vector.

The purified pAP 190 was tested for susceptibility to cleavage by HIV protease and for activation of the A-chain of the pro-ricin variant, (inhibition of protein synthesis). PAP 190 was incubated with and without HIV protease for a specified time period and then electrophoresed and blotted. Cleaved pAP 190 will run as two 30 kDa proteins (B is slightly larger) under reducing (SDS-PAGE) conditions. Unprocessed pAP 190, which contains the linker region, will run at 60 kDa. HIV protease was able to cleave the pAP 190 (shown in FIG. 14). Lanes B and D show untreated; while lanes C and E to G show HIV protease treated pAP 190.
Activation of pAP 190 Variant with HIV Protease Activation of HIV protease treated pAP 190 190, based on the method of May et al. (EMBO Journal. 8 301–8, 1989) was demonstrated in FIG. 15. The appearance of the 390 based pair product is observed in lane B, which is the positive control, and not observed in lane C, the negative control. Lanes D–G show that there was no N-glycosidase activity in the pAP 190 variant as predicted. Lanes H–K show that processed pAP 190 possesses N-glycosidase activity as predicted.

The pAP 190 variant has been expressed in insect cells, purified to greater than 99%, and activation of the variant has been demonstrated by cleavage with HIV protease.

Example 3
Cloning and Expression of Proricin Variants Activated by HTLV
Isolation of Total RNA The preproricin gene is cloned from new foliage of the castor bean plant. Total messenger RNA is isolated according to established procedures (Maniatis et al., Molecular Cloning: A Lab Manual (Cold Spring Harbour Press, Cold Spring Harbour, (1989)) and cDNA generated using reverse transcriptase.
cDNA Synthesis Oligonucleotides, corresponding to the extreme 5' and 3' ends of the preproricin gene are synthesized and used to PCR amplify the gene. Using the cDNA sequence for preproricin (Lamb et al., *Eur. J. Biochem.* 145:266–270 (1985)), several oligonucleotide primers are designed to flank the start and stop codons of the preproricin open reading frame. The oligonucleotides are synthesized using an Applied Biosystems Model 392 DNA/RNA Synthesizer. First strand cDNA synthesis is primed using the oligonucleotide Ricin1729C (Table 1). Three micrograms of total RNA is used as a template for oligo Ricin1729C primed synthesis of cDNA using Superscript II Reverse Transcriptase (BRL) following the manufacturer's protocol.
DNA Amplification and Cloning The first strand cDNA synthesis reaction is used as template for DNA amplification by the polymerase chain reaction (PCR). The preproricin cDNA is amplified using the upstream primer Ricin-109 and the downstream primer Ricin1729C with Vent DNA polymerase (New England Biolabs) using standard procedures (Sambrook et al., Molecular Cloning: A Laboratory Manual, Second Edition, (Cold Spring Harbor Laboratory Press, 1989)). Amplification is carried out in a Biometra thermal cycler (TRIO-Thermalcycler) using the following cycling parameters: denaturation 95° C. for 1 min., annealing 52° C. for 1 min., and extension 72° C. for 2 min., (33 cycles), followed by a final extension cycle at 72° C. for 10 min. The 1846 bp amplified product is fractionated on an agarose gel (Sambrook et al., Molecular Cloning: A Laboratory Manual, Second Edition, (Cold Spring Harbor Laboratory Press, 1989), and the DNA purified from the gel slice using Qiaex resin (Qiagen) following the manufacturer's protocol. The purified PCR fragment encoding the preproricin cDNA is then ligated (Sambrook et al., Molecular Cloning: A Laboratory Manual, Second Edition, (Cold Spring Harbor Laboratory Press, 1989)) into an Eco RI-digested pBluescript II SK plasmid (Stratagene), and used to transform competent XL1-Blue cells (Stratagene). Positive clones are confirmed by restriction digestion of purified plasmid DNA. Plasmid DNA is extracted using a Qiaprep Spin Plasmid Miniprep Kit (Qiagen).

DNA Sequencing

The cloned PCR product containing the putative preproricin gene is confirmed by DNA sequencing of the entire cDNA clone (pAP-144). Sequencing is performed using an Applied Biosystems 373A Automated DNA Sequencer, and confirmed by double-stranded dideoxy sequencing by the Sanger method using the Sequenase kit (USB). The oligonucleotide primers used for sequencing are as follows: Ricin267, Ricin486, Ricin725, Ricin937, Ricin1151, Ricin 1399, Ricin1627, T3 primer (5'AATTAACCCTCACTAAAGGG-3') and T 7 primer (5'GTAATACGACTCACTATAGGGC-3). Sequence data is compiled and analyzed using PC Gene software package (intelligenetics). The sequences and location of oligonucleotide primers is shown in Table 1.

Mutagenesis of Preproricin Linker

The preproricin cDNA clone (pAP-144) is subjected to site directed mutagenesis in order to generate a series of variants differing only in the sequence between the A and B chains (linker region). The wild-type preproricin linker region is replaced with the linker sequences displayed in FIG. 20 (SEQ ID NOS: 55–58). The linker regions of the variants encode a disease-specific protease cleavage recognition sequence (Slalka et al., Cell, 56:911–913, 1989). The mutagenesis and cloning strategy used to generate the HTLV protease-sensitive linker variants is summarized in FIGS. 16A, 17A, 18A and 19A.

The first step involves a DNA amplification using a set of mutagenic primers encoding for the disease-specific protease-sensitive linker in combination with the two flanking primers Ricin-109Eco and Ricin1729Xba. The PCR protocol and conditions used are the same as described above. PCR products from each mutagenesis reaction are gel purified then restriction digested with either Eco Rl for the A-chain encoding fragment, or Xba I for the B chain encoding fragment. Restriction digested PCR fragments are gel purified and then ligated with pBluescript SK which has been digested with Eco RI and Xba I. Ligation reactions are used to transform competent XL1-Blue cells (Stratagene). Recombinant clones are identified by restriction digests of plasmid miniprep DNA and the mutant linker sequence are confirmed by DNA sequencing.

Subcloning Preproricin Mutants into Vector pVL1393

Preproricin variants are subcloned into the baculovirus transfer vector pVL1393 (PharMingen). The subcloning strategy for the HTLV protease-sensitive linker variants is summarized in FIGS. 16C, 17C, 18C, and 19C. The 1315 bp Eco RI/Kpn I fragment encoding the ricin A-chain and each mutant linker is isolated from pAP-205, pAP-207, pAP-209 or pAP-211. Each of these purified fragments is ligated with a 564 bp KpnI/PStI fragment obtained from pAP-144, and with Eco RI/Pst I cleaved pVL1393. Recombinant clones are identified by restriction digests of plasmid miniprep DNA and the 5' and 3' junctions confirmed by DNA sequencing.

Isolation of Recombinant Baculoviruses

Insect cells S. frugiperda (Sf9), and Trichoplusia ni (Tn368 and BTI TN-581-4 (High Five)) are maintained on TMN-FH medium supplemented with 10% total calf serum (Summers et al., A Manual of Methods of Baculovirus Vectors and Insect Cell Culture Procedures, (Texas Agricultural Experiment Station, 1987)). Two micrograms of recombinant pVL1393 DNA (pAP-190, pAP-196, or pAP-197) is co-transfected with 0.5 microgram of BaculoGold AcNPV DNA (Pharmingen) into $2 \times 10^6$ Tn368 insect cells following the manufacturer's protocol (Gruenwald et al., Baculovirus Expression Vector System: Procedures and Methods Manual, 2nd Edition, (San Diego, Calif., 1993)). On day 5 post-transfection, media are centrifuged and the supernatants tested in limiting dilution assays with Tn368 cells (Summers et al., A Manual of Methods of Baculovirus Vectors and Insect Cell Culture Procedures, (Texas Agricultural Experiment Station, 1987)). Recombinant viruses in the supernatants are then amplified by infecting Tn368 cells at a multiplicity of infection (moi) of 0.1, followed by collection of day 7 supernatants. A total of three rounds of amplification are performed for each recombinant following established procedures (Summers et al., A Manual of Methods of Baculovirus Vectors and Insect Cell Culture Procedures, (Texas Agricultural Experiment Station, 1987 and Gruenwald et al., Baculovirus Expression Vector System: Procedures and Methods Manual, 2nd Edition, (San Diego, Calif., 1993)).

Expression of Mutant Proricin

Recombinant baculoviruses (pAP-206-baculo, pAP-208-baculo, pAP-210-baculo, and pAP-212-baculo) are used to infect $2 \times 10^5$ Tn368 or sf9 cells of an moi of 5 in EX-CELL400 media (JRH Biosciences) with 25 mM a-lactose in spinner flasks. Media supernatants containing mutant proricins are collected on day 6 post-infection.

Purification of Mutant Proricin

Media supernatants are ultracentrifuged at 100,000 g for 1 hour. After the addition of 1 mM phenylmethylsulfonyl fluoride, the supernatants are concentrated using an Amicon 8050 Ultrafiltration Cell fitted with a Diaflo XM50 membrane. Supernatants are then dialysed extensively against 137 mN NaCl, 2.2 mM KCl, 2.6 mM $KH_2PO_4$, and 8.6 mM $Na_2HPO_4$, pH 7.4 containing 1 mM dithiothreitol (dialysis buffer). Recombinant proricin proteins are purified by affinity chromatography using lactose agarose (Sigma) as previously described for recombinant ricin-B chain (Ferrini et al., Eur. J. Biochem. 233:772–777 (1995)). Fractions containing recombinant proricin are identified using SDS/PAGE, (Sambrook et al., Molecular Cloning: A Laboratory Manual, Second Edition, (Cold Spring Harbor Laboratory Press, 1989) and by Western blot analysis using anti-ricin antibodies (Sigma).

In Vitro Protease Digestion of Proricin Variants

Affinity-purified proricin variant is treated with individual disease-specific proteases to confirm specific cleavage in the linker region. Ricin-like toxin variants are eluted from the lactose-agarose matrix in protease digestion buffer (50 mM NaCl, 50 mM Na-acetate, pH 5.5, 1 mM dithiothreitol) containing 100 mM lactose. Proricin substrate is then incubated at 37° C. for 60 minutes with a disease-specific protease. The cleavage products consisting ricin A and B chains are identified using SDS/PAGE (Sambrook et al., Molecular Cloning: a Laboratory Manual, 2nd. ed., Cold Spring Harbor Press, 1989), followed by Western blot analysis using anti-ricin antibodies (Sigma).

HTLV proteases may be obtained from Bachem Bioscience. Cathepsin B may be obtained from Medcor or Calbiochem.

In Vitro Translation Assay

The activity of protease-treated ricin-like toxin variants is monitored using a rabbit reticulocyte lysate in a non-radioactive (Amersham, ECL system) in vitro translation assay. Protease-treated proricin is added to a standard 50 ml translation reaction mix containing Brome Mosaic Virus mRNA as template (following the manufacturer's protocol). Active ricin variants inhibit the in vitro translation reaction by inactivating ribosomes. Therefore, in the presence of an active ricin variant, no viral proteins are synthesized.

In Vitro Yeast Protein Synthesis Assay

The activity of protease-treated proricin-like toxins may also be assessed by a yeast protein synthesis assay. For example, Murakami, S et al., Mol., Cel. Biol. 2:588–592, 1982, teaches a yeast protein synthesis assay to determine ricin-like toxicity which is as sensitive as mammalian cell assays.

Six five mL cultures of *Saccharomyces cerevisiase* (Y235 cells and 2 cell wall mutants) in YPD medium (10 g/L yeast extract, 20 g/L peptone) are started by inoculating 800 uL of medium with 1 colony of *Saccharomyces cerevisiase*, vortexing, then adding 100 uL of this suspension to 5 mL of medium. Cultures are grown overnight at 30° C. with gentle agitation. Cells are expanded by inoculating 100 uL of YPD medium with one or more of the 5 mL overnight cultures and are grown at 30° C. with gentle agitation until a concentration of $1 \times 10^5$ cells/mL. Cells are washed with sterile double-distilled water, centrifuged at 1,200 g for 3 minutes and concentrated 3-fold in ZSM buffer(1 M sorbitol, 10 mM Tris-Cl, pH 7.5, 50 mM dithiotheitol (DDT)). Samples are incubated with gentle shaking for 10 minutes at 30° C., centrifuged at 1,200 g for 3 minutes and resuspended in ZSM buffer such that the cell concentration was $1 \times 10^8$ cells/ml. Cell walls are disrupted by adding 1 mL of beta-glucuronidase (Sigma, St. Louis, Mo.) to the samples and incubating for 1 hour at room temperature with gentle agitation. Cells are washed 3 times with ZSM and protoplast cells resuspended in regeneration medium (0.17% yeast nitrogen base without amino acids (Difco, Detroit, Mich.), 2 Dropout+all (essential amino acids), 10 mM Tris-Cl, pH 7.5, 2% glucose, 1M sorbitol) to a final concentration of $1 \times 10^8$ cells/mL. An activated proricin variant which has been dialysed in sterile 1xbaculo buffer (0.137 M) NaCl, 2.7 mM KCl, 2.6 mM $KH_2PO_4$ pH 7.4) is added to one half of the protoplast, while sterile 1xbaculo buffer alone is added to the other half of the protoplasts as control. Both sets of samples are incubated at room temperature with gentle agitation. At time periods of 0, 1, 2, and 3 hours, an aliquot of each culture is removed. The cells are diluted serially from $10^{-4}$ to $10^{-8}$ in ZSM and plated on soft agar (1:1 ZSM:YPD, 15% agar). Simultaneously, dilutions are made from $10^{-2}$ to $10^{-4}$ in sterile double-distilled water and 50 uL aliquots are plated onto YPD medium with 20% agar. Plates are incubated for 2 days at 30° C. after which times colonies were counted. A plot of cell count vs. time is used to compare the ricin test culture vs. the control culture with no ricin.

The activated proricin-like toxin variant inhibits in vitro protein synthesis through ribosomal inactivation. The rate of cell growth of the treatment group is expected to be substantially lower than that of the control group.

N-Glycosidase Activity of Proricin Variants on rRNA Oligonucleotides

Ricin-like toxins inhibit ribosomal function by hydrolysing the N-glycosidic bond between the nucleotide base and the ribose at position A4319 in eukaryotic 28S ribosomal RNA (rRNA). The ability of the activated ricin-like toxins to inhibit ribosomal RNA (rRNA) function may be examined in an in vitro ribonucleotide catalysis assay using a synthetic oligoribonucleotide possessing the secondary structure of the natural RNA hydrolytic cleavage domain.

A synthetic 32-nucleotide RNA oligomer (University of Calgary, DNA Core Services) that mimics the 28S rRNA toxin active site is used to test the N-glycosidase activity of proricin variants. The sequence of oligonucleotide and the general methodology are substantially as described in Gluck, A. and Wool I. G., *J. Mol. Biol.* 256:838–848, 1996.

A labelling reaction is set up to include: 50 pmol of oligonucleotide, 20 units of T4 polynucleotide kinase (PNK; Gibco-BRL, Gaithersburg, Mass.), 25 pmol of $\gamma$-$^{32}$P (Amersham, Arlington, Ill.), 1xT4 PNK buffer in a final volume of 50 uL. The samples are incubated for 30 minutes at 37° C. and them for 20 minutes at 65° C. The labelled oligonucleotide is precipitated with 95% ethanol an dried using a thermal cycler. A second ethanol precipitation step can be repeated to remove further trace contaminants. The RNA was resuspended to a final concentration of 1 ng/uL in 10 mM Tris-Cl (pH 7.6) and 50 mM NaCl (5 ng of oligonucleotide is used per sample).

Activated proricin variant is reduced in 1xbaculo buffer with 1% beta-mercaptoethanol for 30 minutes at room temperature prior to use. The oligonucleotides are heated at 90° C. for 1 minute in 10 mM Tris-Cl (pH 7.6), 50 mM NaCl and allowed to renature at 0° C. $CaCl_2$, EGTA and water are added to the renatured RNA to give the following concentrations: 3 mM Tris-HCl (pH 7.6), 15 mM NaCl, 5 mM $CaCl_2$, and 5 mM EGTA. An activated proricin variant or ricin A-chain (Sigma, St. Louis, Mo.) is added to each tube. The concentration of the ricin ranged from 1–10 uM and the proricin variant 10-fold greater. The tubes are incubated at 35° C. for 20 minutes and the reaction is stopped by the addition of sodium dodecylsulfate (SDS) at a final concentration of 0.5% (w/v). The oligonucleotide and 15 ug of added carrier tRNA (yeast tRNA; Gibco-BRL Gaithersburg, Mass.) are precipitated with 300 mM NaCl and 2.5 volumes of 95% ethanol. The pellets are washed once with 70% ethanol and dried on a CENTRIVAP (Labconco, Kansas City, Mo.). The RNA is dissolved in 5 uL of water, 25 uL of a solution of aniline and acetic acid (1 and 2.8 mM respectively) is added and the sample is incubated for 10 minutes at 40° C. The aniline-treated RNA is precipitate with ethanol and 300 mM NaCl, washed once in 70% ethanol and dried on the CENTRIVAP. The pellets are dissovled in 10 uL of DEPC-treated double-distilled water and 10 uL of 2xloading dy (178 mM Tris-HCl (pH 8.3), 178 mM boric acid, 5 mM EDTA, 0.05% (w/v) bromophenol blue and 14 M urea), and are electrophoresed for 3 hours at 50 watts in 10% (w/v) polyacrylamide gel containing 7 M urea in 1xTBE buffer (89 mM Tris-HCl (pH 8.3), 89 mM boric acid, 2.5 mM boric acid, 2.5 mM EDTA). Gels are exposed to KODAK full speed blue X-ray film and left at −70° C. After 2 days, film was developed in a KODAK automatic film processor.

When proricin variant activated with a disease-specific protease is added to the oligoribonucleotide, hydrolysis of the N-glycosidic bond at position 20 (depurination of adenosine) would occur and appearance of two bands on the autograph is expected. Proricin variant without pretreatment with the disease-specific protease would not cleave the RNA oligonucleotide and would result in a single band on the autoradiograph.

In Vitro Cytotoxicity Assay

Human ovarian cancer cells (e.g. MA148) are seeded in 96-well flat-bottom plates and are exposed to ricin-like toxin variants or control medium at 37° C. for 16 h. The viability of the cancer cells is determined by measuring [$^{35}$S] methionine incorporation and is significantly lower in wells treated with the toxin variants than those with control medium.

In Vivo Tumour Growth Inhibition Assay

Human breast cancer (e.g. MCF-7) cells are maintained in suitable medium containing 10% fetal calf serum. The cells are grown, harvested and subsequently injected subcutaneously into ovariectomized athymic nude mice. Tumour size is determined at intervals by measuring two right-angle measurements using calipers.

In Vivo Tumour Metastasis Assay

The metastasis study is performed substantially as described in Honn, K. V. et al. (*Biochem. Pharmacol.* 34:235–241 (1985)). Viable B16a melanoma tumour cells are prepared and injected subcutaneously into the left axillary region of syngeneic mice. The extent of tumour metastasis is measured after 4 weeks. The lungs are removed from the animals and are fixed in Bouin's solution and macroscopic pulmonary metastases are counted using a dissecting microscope. In general without therapeutic intervention, injection of $10^5$ viable tumour cells forms approximately 40–50 pulmonary metastases.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

Table I - Sequence and Location of Oligonucleotide Primers

| Name of Primer | Primer Sequence[†] | Corresponds to proricin nucleotide numbers (see FIGS. 8–10) |
|---|---|---|
| Ricin-109 | 5'-GGAGATGAAACCGGGAGGAAATACTATTGTAAT-3' (SEQ.ID.NO:61) | 27 to 59 |
| Ricin-99Eco | 5'-GCGGAATTCCGGGAGGAAATACTATTG AAT-3' (SEQ.ID.NO:62) | 37 to 59 |
| Ricin267 | 5'-ACGGTTTATTTTAGTTGA-3' (SEQ.ID.NO.63) | 300 to 317 |
| Ricin486 | 5'-ACTTGCTGGTAATCTGAG-3' (SEQ.ID.NO.64) | 519 to 536 |
| Ricin725 | 5'-AGAATAGTTGGGGGAGAC-3' (SEQ.ID.NO.65) | 758 to 775 |
| Ricin937 | 5'-AATGCTGATGTTTGTATG-3' (SEQ.ID.NO.66) | 970 to 987 |
| Ricin1151 | 5'-CGGGAGTCTATGTGATGA-3' (SEQ.ID.NO.67) | 1184 to 1201 |
| Ricin1399 | 5'-GCAAATAGTGGACAAGTA-3' (SEQ.ID.NO.68) | 1432 to 1449 |
| Ricin1627 | 5'-GGATTGGTGTTAGATGTG-3' (SEQ.ID.NO.69) | 1660 to 1677 |
| Ricin1729C | 5'-ATAACTTGCTGTCCTTTCA-3' (SEQ.ID.NO.70) | 1864 to 1846 |
| Ricin1729C Xba | 5'-CGCTCTAGATAACTTGCTGTCCTTTCA-3' (SEQ.ID.NO.71) | 1864 to 1846 |

[†]underlined sequences inserted for subcloning purposes and not included in final preproricin sequences

SEQUENCE LISTING (1) GENERAL INFORMATION:

(iii) NUMBER OF SEQUENCES: 71

(2) INFORMATION FOR SEQ ID NO:1:

&

(A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AGAAACGAAT ATTCCGGTCA CCACGGTTTA AAATTA                                      36

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TATCCAATAG TGCAAAATTT TAATGCGAT                                              29

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGTGGTAGCA GTGTCAAACA AAGCGTCTTG                                             30

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTTTCGCAGA ACTATCCAAT AGTGCAAAAT TTTAAT                                      36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CAAAGCGTCT TGATAGGTTA TCACGTTTTA AAATTA                                      36

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCTTTGCTTA TAAGGCCAGT GGTGCCAAAT TTTAAT                                      36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGAAACGAAT ATTCCGGTCA CCACGGTTTA AAATTA                                      36

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCGGAGGCAA TGTCTAATGC TGATGTTTGT                                             30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGCAGTGTCA AAAGATTCCG AGCTCACGAT                                             30

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TCTAAGGCTC GAGTGCTAGC GGAGGCAATG TCTAAT                                      36

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGATTCCGAG CTCACGATCG CCTCCGTTAC AGATTA                                        36

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TCTTTGCTTA TAAGGCCAGT GGTGCCAAAT TTTAAT                                        36

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AGAAACGAAT ATTCCGGTCA CCACGGTTTA AAATTA                                        36

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TTCCTGGACG GTATTAATGC TGATGTTTGT                                               30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AGCAGTGTCA AAAGATAAGC ATTTTAGGAT                                               30

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TCTATTCGTA AAATCCTATT CCTGGACGGT ATTAAT                                        36

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AGATTAAGCA TTTTAGGATA AGGACCTGCC ATAATTA                                              37

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ser Leu Leu Ile Arg Pro Val Val Pro Asn Phe Asn
1               5                   10

(2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Val Ser Gln Asn Tyr Pro Ile Val Gln Asn Phe Asn
1               5                   10

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Ser Lys Ala Arg Val Leu Ala Glu Ala Met Ser Asn
1               5                   10

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Ser Ile Arg Lys Ile Leu Phe Leu Asp Gly Ile Asn
1               5                   10

(2) INFORMATION FOR SEQ ID NO:23:

(i) SEQUENCE CHARACTERISTICS:
       (A) LENGTH: 1879 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:23:

```
GAATTCCCCT CGAGACGCGT CGACCCGGAG ATGAAACCGG GAGGAAATAC TATTGTAATA      60
TGGATGTATG CAGTGGCAAC ATGGCTTTGT TTTGGATCCA CCTCAGGGTG GTCTTTCACA     120
TTAGAGGATA CAACATATT  CCCCAAACAA TACCCAATTA TAAACTTTAC CACAGCGGGT     180
GCCACTGTGC AAAGCTACAC AAACTTTATC AGAGCTGTTC GCGGTCGTTT AACAACTGGA     240
GCTGATGTGA GACATGATAT ACCAGTGTTG CCAAACAGAG TTGGTTTGCC TATAAACCAA     300
CGGTTTATTT TAGTTGAACT CTCAAATCAT GCAGAGCTTT CTGTTACATT AGCGCTGGAT     360
GTCACCAATG CATATGTGGT CGGCTACCGT GCTGGAAATA GCGCATATTT CTTTCATCCT     420
GACAATCAGG AAGATGCAGA AGCAATCACT CATCTTTTCA CTGATGTTCA AAATCGATAT     480
ACATTCGCCT TTGGTGGTAA TTATGATAGA CTTGAACAAC TTGCTGGTAA TCTGAGAGAA     540
AATATCGAGT TGGGAAATGG TCCACTAGAG GAGGCTATCT CAGCGCTTTA TTATTACAGT     600
ACTGGTGGCA CTCAGCTTCC AACTCTGGCT CGTTCCTTTA TAATTTGCAT CCAAATGATT     660
TCAGAAGCAG CAAGATTCCA ATATATTGAG GGAGAAATGC GCACGAGAAT TAGGTACAAC     720
CGGAGATCTG CACCAGATCC TAGCGTAATT ACACTTGAGA ATAGTTGGGG GAGACTTTCC     780
ACTGCAATTC AAGAGTCTAA CCAAGGAGCC TTTGCTAGTC AATTCAACT  GCAAAGACGT     840
AATGGTTCCA AATTCAGTGT GTACGATGTG AGTATATTAA TCCCTATCAT AGCTCTCATG     900
GTGTATAGAT GCGCACCTCC ACCATCGTCA CAGTTTGTTT CGCAGAACTA TCCAATAGTG     960
CAAAATTTTA ATGCTGATGT TTGTATGGAT CCTGAGCCCA TAGTGCGTAT CGTAGGTCGA    1020
AATGGTCTAT GTGTTGATGT TAGGGATGGA AGATTCCACA ACGGAAACGC AATACAGTTG    1080
TGGCCATGCA AGTCTAATAC AGATGCAAAT CAGCTCTGGA CTTTGAAAAG AGACAATACT    1140
ATTCGATCTA ATGGAAAGTG TTTAACTACT TACGGGTACA GTCCGGGAGT CTATGTGATG    1200
ATCTATGATT GCAATACTGC TGCAACTGAT GCCACCCGCT GGCAAATATG GGATAATGGA    1260
ACCATCATAA ATCCCAGATC TAGTCTAGTT TTAGCAGCGA CATCAGGGAA CAGTGGTACC    1320
ACACTTACAG TGCAAACCAA CATTTATGCC GTTAGTCAAG GTTGGCTTCC TACTAATAAT    1380
ACACAACCTT TGTTACAAC  CATTGTTGGG CTATATGGTC TGTGCTTGCA AGCAAATAGT    1440
GGACAAGTAT GGATAGAGGA CTGTAGCAGT GAAAAGGCTG AACAACAGTG GGCTCTTTAT    1500
GCAGATGGTT CAATACGTCC TCAGCAAAAC CGAGATAATT GCCTTACAAG TGATTCTAAT    1560
ATACGGGAAA CAGTTGTTAA GATCCTCTCT TGTGGCCCTG CATCCTCTGG CCAACGATGG    1620
ATGTTCAAGA ATGATGGAAC CATTTTAAAT TTGTATAGTG GATTGGTGTT AGATGTGAGG    1680
CGATCGGATC CGAGCCTTAA ACAAATCATT CTTTACCCTC TCCATGGTGA CCCAAACCAA    1740
ATATGGTTAC CATTATTTTG ATAGACAGAT TACTCTCTTG CAGTGTGTGT GTCCTGCCAT    1800
GAAAATAGAT GGCTTAAATA AAAGGACAT  TGTAAATTTT GTAACTGAAA GGACAGCAAG    1860
TTATATCGAA TTCCTGCAG                                                 1879
```

(2) INFORMATION FOR SEQ ID NO:24:

(i) SEQUENCE CHARACTERISTICS:
    (A) LENGTH: 1879 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:24:

```
GAATTCCCCT CGAGACGCGT CGACCCGGAG ATGAAACCGG GAGGAAATAC TATTGTAATA      60

TGGATGTATG CAGTGGCAAC ATGGCTTTGT TTTGGATCCA CCTCAGGGTG GTCTTTCACA     120

TTAGAGGATA ACAACATATT CCCCAAACAA TACCCAATTA TAAACTTTAC CACAGCGGGT     180

GCCACTGTGC AAAGCTACAC AAACTTTATC AGAGCTGTTC GCGGTCGTTT AACAACTGGA     240

GCTGATGTGA GACATGATAT ACCAGTGTTG CCAAACAGAG TTGGTTTGCC TATAAACCAA     300

CGGTTTATTT TAGTTGAACT CTCAAATCAT GCAGAGCTTT CTGTTACATT AGCGCTGGAT     360

GTCACCAATG CATATGTGGT CGGCTACCGT GCTGGAAATA GCGCATATTT CTTTCATCCT     420

GACAATCAGG AAGATGCAGA AGCAATCACT CATCTTTTCA CTGATGTTCA AAATCGATAT     480

ACATTCGCCT TTGGTGGTAA TTATGATAGA CTTGAACAAC TTGCTGGTAA TCTGAGAGAA     540

AATATCGAGT TGGGAAATGG TCCACTAGAG GAGGCTATCT CAGCGCTTTA TTATTACAGT     600

ACTGGTGGCA CTCAGCTTCC AACTCTGGCT CGTTCCTTTA TAATTTGCAT CCAAATGATT     660

TCAGAAGCAG CAAGATTCCA ATATATTGAG GGAGAAATGC GCACGAGAAT TAGGTACAAC     720

CGGAGATCTG CACCAGATCC TAGCGTAATT ACACTTGAGA ATAGTTGGGG GAGACTTTCC     780

ACTGCAATTC AAGAGTCTAA CCAAGGAGCC TTTGCTAGTC CAATTCAACT GCAAAGACGT     840

AATGGTTCCA AATTCAGTGT GTACGATGTG AGTATATTAA TCCCTATCAT AGCTCTCATG     900

GTGTATAGAT GCGCACCTCC ACCATCGTCA CAGTTTTCTA AGGCTCGAGT GCTAGCGGAG     960

GCAATGTCTA ATGCTGATGT TTGTATGGAT CCTGAGCCCA TAGTGCGTAT CGTAGGTCGA    1020

AATGGTCTAT GTGTTGATGT TAGGGATGGA AGATTCCACA ACGGAAACGC AATACAGTTG    1080

TGGCCATGCA AGTCTAATAC AGATGCAAAT CAGCTCTGGA CTTTGAAAAG AGACAATACT    1140

ATTCGATCTA ATGGAAAGTG TTTAACTACT TACGGGTACA GTCCGGGAGT CTATGTGATG    1200

ATCTATGATT GCAATACTGC TGCAACTGAT GCCACCCGCT GGCAAATATG GGATAATGGA    1260

ACCATCATAA ATCCCAGATC TAGTCTAGTT TTAGCAGCGA CATCAGGGAA CAGTGGTACC    1320

ACACTTACAG TGCAAACCAA CATTTATGCC GTTAGTCAAG GTTGGCTTCC TACTAATAAT    1380

ACACAACCTT TGGTTACAAC CATTGTTGGG CTATATGGTC TGTGCTTGCA AGCAAATAGT    1440

GGACAAGTAT GGATAGAGGA CTGTAGCAGT GAAAAGGCTG AACAACAGTG GCTCTTTTAT    1500

GCAGATGGTT CAATACGTCC TCAGCAAAAC CGAGATAATT GCCTTACAAG TGATTCTAAT    1560

ATACGGGAAA CAGTTGTTAA GATCCTCTCT TGTGGCCCTG CATCCTCTGG CCAACGATGG    1620

ATGTTCAAGA ATGATGGAAC CATTTTAAAT TTGTATAGTG GATTGGTGTT AGATGTGAGG    1680

CGATCGGATC CGAGCCTTAA ACAAATCATT CTTTACCCTC TCCATGGTGA CCCAAACCAA    1740

ATATGGTTAC CATTATTTTG ATAGACAGAT TACTCTCTTG CAGTGTGTGT GTCCTGCCAT    1800

GAAAATAGAT GGCTTAAATA AAAGGACAT TGTAAATTTT GTAACTGAAA GGACAGCAAG    1860

TTATATCGAA TTCCTGCAG                                                 1879
```

(2) INFORMATION FOR SEQ ID NO:25:

(i) SEQUENCE CHARACTERISTICS:
        (A) LENGTH: 1879 base pairs (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:25:

```
GAATTCCCCT CGAGACGCGT CGACCCGGAG ATGAAACCGG GAGGAAATAC TATTGTAATA      60

TGGATGTATG CAGTGGCAAC ATGGCTTTGT TTTGGATCCA CCTCAGGGTG GTCTTTCACA     120

TTAGAGGATA CAACATATT  CCCCAAACAA TACCCAATTA TAAACTTTAC CACAGCGGGT     180

GCCACTGTGC AAAGCTACAC AAACTTTATC AGAGCTGTTC GCGGTCGTTT AACAACTGGA     240

GCTGATGTGA GACATGATAT ACCAGTGTTG CCAAACAGAG TTGGTTTGCC TATAAACCAA     300

CGGTTTATTT TAGTTGAACT CTCAAATCAT GCAGAGCTTT CTGTTACATT AGCGCTGGAT     360

GTCACCAATG CATATGTGGT CGGCTACCGT GCTGGAAATA GCGCATATTT CTTTCATCCT     420

GACAATCAGG AAGATGCAGA AGCAATCACT CATCTTTTCA CTGATGTTCA AAATCGATAT     480

ACATTCGCCT TTGGTGGTAA TTATGATAGA CTTGAACAAC TTGCTGGTAA TCTGAGAGAA     540

AATATCGAGT TGGGAAATGG TCCACTAGAG GAGGCTATCT CAGCGCTTTA TTATTACAGT     600

ACTGGTGGCA CTCAGCTTCC AACTCTGGCT CGTTCCTTTA TAATTTGCAT CCAAATGATT     660

TCAGAAGCAG CAAGATTCCA ATATATTGAG GGAGAAATGC GCACGAGAAT TAGGTACAAC     720

CGGAGATCTG CACCAGATCC TAGCGTAATT ACACTTGAGA ATAGTTGGGG GAGACTTTCC     780

ACTGCAATTC AAGAGTCTAA CCAAGGAGCC TTTGCTAGTC AATTCAACT  GCAAAGACGT     840

AATGGTTCCA AATTCAGTGT GTACGATGTG AGTATATTAA TCCCTATCAT AGCTCTCATG     900

GTGTATAGAT GCGCACCTCC ACCATCGTCA CAGTTTTCTA TTCGTAAAAT CCTATTCCTG     960

GACGGTATTA TGCTGATGT  TTGTATGGAT CCTGAGCCCA TAGTGCGTAT CGTAGGTCGA    1020

AATGGTCTAT GTGTTGATGT TAGGGATGGA AGATTCCACA ACGGAAACGC AATACAGTTG    1080

TGGCCATGCA AGTCTAATAC AGATGCAAAT CAGCTCTGGA CTTTGAAAAG AGACAATACT    1140

ATTCGATCTA ATGGAAAGTG TTTAACTACT TACGGGTACA GTCCGGGAGT CTATGTGATG    1200

ATCTATGATT GCAATACTGC TGCAACTGAT GCCACCCGCT GGCAAATATG GGATAATGGA    1260

ACCATCATAA ATCCCAGATC TAGTCTAGTT TTAGCAGCGA CATCAGGGAA CAGTGGTACC    1320

ACACTTACAG TGCAAACCAA CATTTATGCC GTTAGTCAAG GTTGGCTTCC TACTAATAAT    1380

ACACAACCTT TTGTTACAAC CATTGTTGGG CTATATGGTC TGTGCTTGCA AGCAAATAGT    1440

GGACAAGTAT GGATAGAGGA CTGTAGCAGT GAAAAGGCTG AACAACAGTG GGCTCTTTAT    1500

GCAGATGGTT CAATACGTCC TCAGCAAAAC CGAGATAATT GCCTTACAAG TGATTCTAAT    1560

ATACGGGAAA CAGTTGTTAA GATCCTCTCT TGTGGCCCTG CATCCTCTGG CCAACGATGG    1620

ATGTTCAAGA ATGATGGAAC CATTTTAAAT TTGTATAGTG GATTGGTGTT AGATGTGAGG    1680

CGATCGGATC CGAGCCTTAA ACAAATCATT CTTTACCCTC TCCATGGTGA CCCAAACCAA    1740

ATATGGTTAC CATTATTTTG ATAGACAGAT TACTCTCTTG CAGTGTGTGT GTCCTGCCAT    1800

GAAAATAGAT GGCTTAAATA AAAAGGACAT TGTAAATTTT GTAACTGAAA GGACAGCAAG    1860

TTATATCGAA TTCCTGCAG                                                 1879
```

(2) INFORMATION FOR SEQ ID NO:26:

(i) SEQUENCE CHARACTERISTICS:
        (A) LENGTH: 9639 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:26:

```
AAGCTTTACT CGTAAAGCGA GTTGAAGGAT CATATTTAGT TGCGTTTATG AGATAAGATT      60
GAAAGCACGT GTAAAATGTT TCCCGCGCGT TGGCACAACT ATTTACAATG CGGCCAAGTT     120
ATAAAAGATT CTAATCTGAT ATGTTTTAAA ACACCTTTGC GGCCCGAGTT GTTTGCGTAC     180
GTGACTAGCG AAGAAGATGT GTGGACCGCA GAACAGATAG TAAAACAAAA CCCTAGTATT     240
GGAGCAATAA TCGATTTAAC CAACACGTCT AAATATTATG ATGGTGTGCA TTTTTTGCGG     300
GCGGGCCTGT TATACAAAAA AATTCAAGTA CCTGGCCAGA CTTTGCCGCC TGAAAGCATA     360
GTTCAAGAAT TTATTGACAC GGTAAAAGAA TTTACAGAAA AGTGTCCCGG CATGTTGGTG     420
GGCGTGCACT GCACACACGG TATTAATCGC ACCGGTTACA TGGTGTGCAG ATATTTAATG     480
CACACCCTGG GTATTGCGCC GCAGGAAGCC ATAGATAGAT TCGAAAAAGC CAGAGGTCAC     540
AAAATTGAAA GACAAAATTA CGTTCAAGAT TTATTAATTT AATTAATATT ATTTGCATTC     600
TTTAACAAAT ACTTTATCCT ATTTTCAAAT TGTTGCGCTT CTTCCAGCGA ACCAAAACTA     660
TGCTTCGCTT GCTCCGTTTA GCTTGTAGCC GATCAGTGGC GTTGTTCCAA TCGACGGTAG     720
GATTAGGCCG GATATTCTCC ACCACAATGT TGGCAACGTT GATGTTACGT TTATGCTTTT     780
GGTTTTCCAC GTACGTCTTT TGGCCGGTAA TAGCCGTAAA CGTAGTGCCG TCGCGCGTCA     840
CGCACAACAC CGGATGTTTG CGCTTGTCCG CGGGGTATTG AACCGCGCGA TCCGACAAAT     900
CCACCACTTT GGCAACTAAA TCGGTGACCT GCGCGTCTTT TTTCTGCATT ATTTCGTCTT     960
TCTTTTGCAT GGTTTCCTGG AAGCCGGTGT ACATGCGGTT TAGATCAGTC ATGACGCGCG    1020
TGACCTGCAA ATCTTTGGCC TCGATCTGCT TGTCCTTGAT GGCAACGATG CGTTCAATAA    1080
ACTCTTGTTT TTTAACAAGT TCCTCGGTTT TTTGCGCCAC CACCGCTTGC AGCGCGTTTG    1140
TGTGCTCGGT GAATGTCGCA ATCAGCTTAG TCACCAACTG TTTGCTCTCC TCCTCCCGTT    1200
GTTTGATCGC GGGATCGTAC TTGCCGGTGC AGAGCACTTG AGGAATTACT TCTTCTAAAA    1260
GCCATTCTTG TAATTCTATG GCGTAAGGCA ATTTGGACTT CATAATCAGC TGAATCACGC    1320
CGGATTTAGT AATGAGCACT GTATGCGGCT GCAAATACAG CGGGTCGCCC CTTTTCACGA    1380
CGCTGTTAGA GGTAGGGCCC CCATTTTGGA TGGTCTGCTC AAATAACGAT TTGTATTTAT    1440
TGTCTACATG AACACGTATA GCTTTATCAC AAACTGTATA TTTTAAACTG TTAGCGACGT    1500
CCTTGGCCAC GAACCGGACC TGTTGGTCGC GCTCTAGCAC GTACCGCAGG TTGAACGTAT    1560
CTTCTCCAAA TTTAAATTCT CCAATTTTAA CGCGAGCCAT TTTGATACAC GTGTGTCGAT    1620
TTTGCAACAA CTATTGTTTT TTAACGCAAA CTAAACTTAT TGTGGTAAGC AATAATTAAA    1680
TATGGGGAA CATGCGCCGC TACAACACTC GTCGTTATGA ACGCAGACGG CGCCGGTCTC    1740
GGCGCAAGCG GCTAAAACGT GTTGCGCGTT CAACGCGGCA AACATCGCAA AAGCCAATAG    1800
TACAGTTTTG ATTTGCATAT TAACGGCGAT TTTTTAAATT ATCTTATTTA ATAAATAGTT    1860
ATGACGCCTA CAACTCCCCG CCCGCGTTGA CTCGCTGCAC CTCGAGCAGT TCGTTGACGC    1920
CTTCCTCCGT GTGGCCGAAC ACGTCGAGCG GGTGGTCGAT GACCAGCGGC GTGCCGCACG    1980
CGACGCACAA GTATCTGTAC ACCGAATGAT CGTCGGGCGA AGGCACGTCG GCCTCCAAGT    2040
GGCAATATTG GCAAATTCGA AAATATATAC AGTTGGGTTG TTTGCGCATA TCTATCGTGG    2100
CGTTGGGCAT GTACGTCCGA ACGTTGATTT GCATGCAAGC CGAAATTAAA TCATTGCGAT    2160
TAGTGCGATT AAAACGTTGT ACATCCTCGC TTTTAATCAT GCCGTCGATT AAATCGCGCA    2220
```

-continued

```
ATCGAGTCAA GTGATCAAAG TGTGGAATAA TGTTTTCTTT GTATTCCCGA GTCAAGCGCA    2280

GCGCGTATTT TAACAAACTA GCCATCTTGT AAGTTAGTTT CATTTAATGC AACTTTATCC    2340

AATAATATAT TATGTATCGC ACGTCAAGAA TTAACAATGC GCCCGTTGTC GCATCTCAAC    2400

ACGACTATGA TAGAGATCAA ATAAAGCGCG AATTAAATAG CTTGCGACGC AACGTGCACG    2460

ATCTGTGCAC GCGTTCCGGC ACGAGCTTTG ATTGTAATAA GTTTTTACGA AGCGATGACA    2520

TGACCCCCGT AGTGACAACG ATCACGCCCA AAGAACTGC CGACTACAAA ATTACCGAGT     2580

ATGTCGGTGA CGTTAAAACT ATTAAGCCAT CCAATCGACC GTTAGTCGAA TCAGGACCGC    2640

TGGTGCGAGA AGCCGCGAAG TATGGCGAAT GCATCGTATA ACGTGTGGAG TCCGCTCATT    2700

AGAGCGTCAT GTTTAGACAA GAAAGCTACA TATTTAATTG ATCCCGATGA TTTTATTGAT    2760

AAATTGACCC TAACTCCATA CACGGTATTC TACAATGGCG GGGTTTTGGT CAAAATTTCC    2820

GGACTGCGAT TGTACATGCT GTTAACGGCT CCGCCCACTA TTAATGAAAT TAAAAATTCC    2880

AATTTTAAAA AACGCAGCAA GAGAAACATT TGTATGAAAG AATGCGTAGA AGGAAAGAAA    2940

AATGTCGTCG ACATGCTGAA CAACAAGATT AATATGCCTC CGTGTATAAA AAAAATATTG    3000

AACGATTTGA AGAAAACAA TGTACCGCGC GGCGGTATGT ACAGGAAGAG GTTTATACTA     3060

AACTGTTACA TTGCAAACGT GGTTTCGTGT GCCAAGTGTG AAAACCGATG TTTAATCAAG    3120

GCTCTGACGC ATTTCTACAA CCACGACTCC AAGTGTGTGG GTGAAGTCAT GCATCTTTTA    3180

ATCAAATCCC AAGATGTGTA TAAACCACCA AACTGCCAAA AATGAAAAC TGTCGACAAG     3240

CTCTGTCCGT TTGCTGGCAA CTGCAAGGGT CTCAATCCTA TTTGTAATTA TTGAATAATA    3300

AAACAATTAT AAATGCTAAA TTTGTTTTTT ATTAACGATA CAAACCAAAC GCAACAAGAA    3360

CATTTGTAGT ATTATCTATA ATTGAAAACG CGTAGTTATA ATCGCTGAGG TAATATTTAA    3420

AATCATTTTC AAATGATTCA CAGTTAATTT GCGACAATAT AATTTTATTT TCACATAAAC    3480

TAGACGCCTT GTCGTCTTCT TCTTCGTATT CCTTCTCTTT TTCATTTTTC TCCTCATAAA    3540

AATTAACATA GTTATTATCG TATCCATATA TGTATCTATC GTATAGAGTA AATTTTTTGT    3600

TGTCATAAAT ATATATGTCT TTTTTAATGG GGTGTATAGT ACCGCTGCGC ATAGTTTTTC    3660

TGTAATTTAC AACAGTGCTA TTTTCTGGTA GTTCTTCGGA GTGTGTTGCT TTAATTATTA    3720

AATTTATATA ATCAATGAAT TTGGGATCGT CGGTTTTGTA CAATATGTTG CCGGCATAGT    3780

ACGCAGCTTC TTCTAGTTCA ATTACACCAT TTTTTAGCAG CACCGGATTA ACATAACTTT    3840

CCAAAATGTT GTACGAACCG TTAAACAAAA ACAGTTCACC TCCCTTTTCT ATACTATTGT    3900

CTGCGAGCAG TTGTTTGTTG TTAAAAATAA CAGCCATTGT AATGAGACGC ACAAACTAAT    3960

ATCACAAACT GGAAATGTCT ATCAATATAT AGTTGCTGAT ATCATGGAGA TAATTAAAAT    4020

GATAACCATC TCGCAAATAA ATAAGTATTT TACTGTTTTC GTAACAGTTT TGTAATAAAA    4080

AAACCTATAA ATATTCCGGA TTATTCATAC CGTCCCACCA TCGGGCGCGG ATCCCGGGTA    4140

CCTTCTAGAA TTCCGGAGCG GCCGCTGCAG ATCTGATCCT TTCCTGGGAC CCGGCAAGAA    4200

CCAAAAACTC ACTCTCTTCA AGGAAATCCG TAATGTTAAA CCCGACACGA TGAAGCTTGT    4260

CGTTGGATGG AAAGGAAAAG AGTTCTACAG GGAAACTTGG ACCCGCTTCA TGGAAGACAG    4320

CTTCCCCATT GTTAACGACC AAGAAGTGAT GGATGTTTTC CTTGTTGTCA ACATGCGTCC    4380

CACTAGACCC AACCGTTGTT ACAAATTCCT GGCCCAACAC GCTCTGCGTT GCGACCCCGA    4440

CTATGTACCT CATGACGTGA TTAGGATCGT CGAGCCTTCA TGGGTGGGCA GCAACAACGA    4500

GTACCGCATC AGCCTGGCTA AGAAGGGCGG CGGCTGCCCA ATAATGAACC TTCACTCTGA    4560
```

```
GTACACCAAC TCGTTCGAAC AGTTCATCGA TCGTGTCATC TGGGAGAACT TCTACAAGCC    4620

CATCGTTTAC ATCGGTACCG ACTCTGCTGA AGAGGAGGAA ATTCTCCTTG AAGTTTCCCT    4680

GGTGTTCAAA GTAAAGGAGT TTGCACCAGA CGCACCTCTG TTCACTGGTC CGGCGTATTA    4740

AAACACGATA CATTGTTATT AGTACATTTA TTAAGCGCTA GATTCTGTGC GTTGTTGATT    4800

TACAGACAAT TGTTGTACGT ATTTTAATAA TTCATTAAAT TTATAATCTT TAGGGTGGTA    4860

TGTTAGAGCG AAAATCAAAT GATTTTCAGC GTCTTTATAT CTGAATTTAA ATATTAAATC    4920

CTCAATAGAT TTGTAAAATA GGTTTCGATT AGTTTCAAAC AAGGGTTGTT TTTCCGAACC    4980

GATGGCTGGA CTATCTAATG GATTTTCGCT CAACGCCACA AAACTTGCCA AATCTTGTAG    5040

CAGCAATCTA GCTTTGTCGA TATTCGTTTG TGTTTTGTTT TGTAATAAAG GTTCGACGTC    5100

GTTCAAAATA TTATGCGCTT TTGTATTTCT TTCATCACTG TCGTTAGTGT ACAATTGACT    5160

CGACGTAAAC ACGTTAAATA AAGCTTGGAC ATATTTAACA TCGGGCGTGT TAGCTTTATT    5220

AGGCCGATTA TCGTCGTCGT CCCAACCCTC GTCGTTAGAA GTTGCTTCCG AAGACGATTT    5280

TGCCATAGCC ACACGACGCC TATTAATTGT GTCGGCTAAC ACGTCCGCGA TCAAATTTGT    5340

AGTTGAGCTT TTTGGAATTA TTTCTGATTG CGGGCGTTTT TGGGCGGGTT TCAATCTAAC    5400

TGTGCCCGAT TTTAATTCAG ACAACACGTT AGAAAGCGAT GGTGCAGGCG GTGGTAACAT    5460

TTCAGACGGC AAATCTACTA ATGGCGGCGG TGGTGGAGCT GATGATAAAT CTACCATCGG    5520

TGGAGGCGCA GGCGGGGCTG GCGGCGGAGG CGGAGGCGGA GGTGGTGGCG GTGATGCAGA    5580

CGGCGGTTTA GGCTCAAATG TCTCTTTAGG CAACACAGTC GGCACCTCAA CTATTGTACT    5640

GGTTTCGGGC GCCGTTTTTG GTTTGACCGG TCTGAGACGA GTGCGATTTT TTTCGTTTCT    5700

AATAGCTTCC AACAATTGTT GTCTGTCGTC TAAAGGTGCA GCGGGTTGAG GTTCCGTCGG    5760

CATTGGTGGA GCGGGCGGCA ATTCAGACAT CGATGGTGGT GGTGGTGGTG GAGGCGCTGG    5820

AATGTTAGGC ACGGGAGAAG GTGGTGGCGG CGGTGCCGCC GGTATAATTT GTTCTGGTTT    5880

AGTTTGTTCG CGCACGATTG TGGGCACCGG CGCAGGCGCC GCTGGCTGCA CAACGGAAGG    5940

TCGTCTGCTT CGAGGCAGCG CTTGGGGTGG TGGCAATTCA ATATTATAAT TGGAATACAA    6000

ATCGTAAAAA TCTGCTATAA GCATTGTAAT TTCGCTATCG TTTACCGTGC CGATATTTAA    6060

CAACCGCTCA ATGTAAGCAA TTGTATTGTA AAGAGATTGT CTCAAGCTCC GCACGCCGAT    6120

AACAAGCCTT TCATTTTTA CTACAGCATT GTAGTGGCGA GACACTTCGC TGTCGTCGAC    6180

GTACATGTAT GCTTTGTTGT CAAAAACGTC GTTGGCAAGC TTTAAAATAT TTAAAAGAAC    6240

ATCTCTGTTC AGCACCACTG TGTTGTCGTA AATGTTGTTT TTGATAATTT GCGCTTCCGC    6300

AGTATCGACA CGTTCAAAAA ATTGATGCGC ATCAATTTTG TTGTTCCTAT TATTGAATAA    6360

ATAAGATTGT ACAGATTCAT ATCTACGATT CGTCATGGCC ACCACAAATG CTACGCTGCA    6420

AACGCTGGTA CAATTTTACG AAAACTGCAA AACGTCAAA ACTCGGTATA AAATAATCAA    6480

CGGGCGCTTT GGCAAAATAT CTATTTTATC GCACAAGCCC ACTAGCAAAT TGTATTTGCA    6540

GAAAACAATT TCGGCGCACA ATTTTAACGC TGACGAAATA AAAGTTCACC AGTTAATGAG    6600

CGACCACCCA AATTTTATAA AAATCTATTT TAATCACGGT TCCATCAACA ACCAAGTGAT    6660

CGTGATGGAC TACATTGACT GTCCCGATTT ATTTGAAACA CTACAAATTA AAGGCGAGCT    6720

TTCGTACCAA CTTGTTAGCA ATATTATTAG ACAGCTGTGT GAAGCGCTCA ACGATTTGCA    6780

CAAGCACAAT TTCATACACA ACGACATAAA ACTCGAAAAT GTCTTATATT TCGAAGCACT    6840

TGATCGCGTG TATGTTTGCG ATTACGGATT GTGCAAACAC GAAAACTCAC TTAGCGTGCA    6900

CGACGGCACG TTGGAGTATT TTAGTCCGGA AAAAATTCGA CACACAACTA TGCACGTTTC    6960
```

```
GTTTGACTGG TACGCGGCGT GTTAACATAC AAGTTGCTAA CCGGCGGTTC GTAATCATGG    7020

TCATAGCTGT TTCCTGTGTG AAATTGTTAT CCGCTCACAA TTCCACACAA CATACGAGCC    7080

GGAAGCATAA AGTGTAAAGC CTGGGGTGCC TAATGAGTGA GCTAACTCAC ATTAATTGCG    7140

TTGCGCTCAC TGCCCGCTTT CCAGTCGGGA AACCTGTCGT GCCAGCTGCA TTAATGAATC    7200

GGCCAACGCG CGGGGAGAGG CGGTTTGCGT ATTGGGCGCT CTTCCGCTTC CTCGCTCACT    7260

GACTCGCTGC GCTCGGTCGT TCGGCTGCGG CGAGCGGTAT CAGCTCACTC AAAGGCGGTA    7320

ATACGGTTAT CCACAGAATC AGGGGATAAC GCAGGAAAGA ACATGTGAGC AAAAGGCCAG    7380

CAAAAGGCCA GGAACCGTAA AAAGGCCGCG TTGCTGGCGT TTTTCCATAG GCTCCGCCCC    7440

CCTGACGAGC ATCACAAAAA TCGACGCTCA AGTCAGAGGT GGCGAAACCC GACAGGACTA    7500

TAAAGATACC AGGCGTTTCC CCCTGGAAGC TCCCTCGTGC GCTCTCCTGT TCCGACCCTG    7560

CCGCTTACCG GATACCTGTC CGCCTTTCTC CCTTCGGGAA GCGTGGCGCT TTCTCATAGC    7620

TCACGCTGTA GGTATCTCAG TTCGGTGTAG GTCGTTCGCT CCAAGCTGGG CTGTGTGCAC    7680

GAACCCCCCG TTCAGCCCGA CCGCTGCGCC TTATCCGGTA ACTATCGTCT TGAGTCCAAC    7740

CCGGTAAGAC ACGACTTATC GCCACTGGCA GCAGCCACTG GTAACAGGAT TAGCAGAGCG    7800

AGGTATGTAG GCGGTGCTAC AGAGTTCTTG AAGTGGTGGC CTAACTACGG CTACACTAGA    7860

AGGACAGTAT TTGGTATCTG CGCTCTGCTG AAGCCAGTTA CCTTCGGAAA AAGAGTTGGT    7920

AGCTCTTGAT CCGGCAAACA AACCACCGCT GGTAGCGGTG GTTTTTTTGT TTGCAAGCAG    7980

CAGATTACGC GCAGAAAAAA AGGATCTCAA GAAGATCCTT TGATCTTTTC TACGGGGTCT    8040

GACGCTCAGT GGAACGAAAA CTCACGTTAA GGGATTTTGG TCATGAGATT ATCAAAAAGG    8100

ATCTTCACCT AGATCCTTTT AAATTAAAAA TGAAGTTTTA AATCAATCTA AGTATATAT    8160

GAGTAAACTT GGTCTGACAG TTACCAATGC TTAATCAGTG AGGCACCTAT CTCAGCGATC    8220

TGTCTATTTC GTTCATCCAT AGTTGCCTGA CTCCCCGTCG TGTAGATAAC TACGATACGG    8280

GAGGGCTTAC CATCTGGCCC CAGTGCTGCA ATGATACCGC GAGACCCACG CTCACCGGCT    8340

CCAGATTTAT CAGCAATAAA CCAGCCAGCC GGAAGGGCCG AGCGCAGAAG TGGTCCTGCA    8400

ACTTTATCCG CCTCCATCCA GTCTATTAAT TGTTGCCGGG AAGCTAGAGT AAGTAGTTCG    8460

CCAGTTAATA GTTTGCGCAA CGTTGTTGCC ATTGCTACAG GCATCGTGGT GTCACGCTCG    8520

TCGTTTGGTA TGGCTTCATT CAGCTCCGGT TCCCAACGAT CAAGGCGAGT TACATGATCC    8580

CCCATGTTGT GCAAAAAAGC GGTTAGCTCC TTCGGTCCTC CGATCGTTGT CAGAAGTAAG    8640

TTGGCCGCAG TGTTATCACT CATGGTTATG GCAGCACTGC ATAATTCTCT TACTGTCATG    8700

CCATCCGTAA GATGCTTTTC TGTGACTGGT GAGTACTCAA CCAAGTCATT CTGAGAATAG    8760

TGTATGCGGC GACCGAGTTG CTCTTGCCCG GCGTCAATAC GGGATAATAC CGCGCCACAT    8820

AGCAGAACTT TAAAAGTGCT CATCATTGGA AAACGTTCTT CGGGGCGAAA ACTCTCAAGG    8880

ATCTTACCGC TGTTGAGATC CAGTTCGATG TAACCCACTC GTGCACCCAA CTGATCTTCA    8940

GCATCTTTTA CTTTCACCAG CGTTTCTGGG TGAGCAAAAA CAGGAAGGCA AAATGCCGCA    9000

AAAAAGGGAA TAAGGGCGAC ACGGAAATGT TGAATACTCA TACTCTTCCT TTTTCAATAT    9060

TATTGAAGCA TTTATCAGGG TTATTGTCTC ATGAGCGGAT ACATATTTGA ATGTATTTAG    9120

AAAAATAAAC AAATAGGGGT TCCGCGCACA TTTCCCCGAA AAGTGCCACC TGACGTCTAA    9180

GAAACCATTA TTATCATGAC ATTAACCTAT AAAAATAGGC GTATCACGAG GCCCTTTCGT    9240

CTCGCGCGTT TCGGTGATGA CGGTGAAAAC CTCTGACACA TGCAGCTCCC GGAGACGGTC    9300
```

```
ACAGCTTGTC TGTAAGCGGA TGCCGGGAGC AGACAAGCCC GTCAGGGCGC GTCAGCGGGT      9360

GTTGGCGGGT GTCGGGGCTG GCTTAACTAT GCGGCATCAG AGCAGATTGT ACTGAGAGTG      9420

CACCATATGC GGTGTGAAAT ACCGCACAGA TGCGTAAGGA GAAAATACCG CATCAGGCGC      9480

CATTCGCCAT TCAGGCTGCG CAACTGTTGG GAAGGGCGAT CGGTGCGGGC CTCTTCGCTA      9540

TTACGCCAGC TGGCGAAAGG GGGATGTGCT GCAAGGCGAT TAAGTTGGGT AACGCCAGGG      9600

TTTTCCCAGT CACGACGTTG TAAAACGACG GCCAGTGCC                            9639
```

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
TCTTTGCTTA TAAGGCCAGT GGTGCCAAAT TTTAAT                               36
```

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
AGAAACGAAT ATTCCGGTCA CCACGGTTTA AAATTA                               36
```

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
CCGGTGATGC ATCCTAATGC TGATGTTTGT                                      30
```

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
AGCAGTGTCA AAAGACGCGG AGTTCACGAT                                      30
```

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:31:

TCTGCGCCTC AAGTGCTACC GGTGATGCAT CCTAAT                                    36

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

AGACGCGGAG TTCACGATGG CCACTACGTA GGATTA                                    36

(2) INFORMATION FOR SEQ ID NO:33:

(i) SEQUENCE CHARACTERISTICS:
        (A) LENGTH: 1855 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GAATTCATGA AACCGGGAGG AAATACTATT GTAATATGGA TGTATGCAGT GGCAACATGG         60

CTTTGTTTTG GATCCACCTC AGGGTGGTCT TTCACATTAG AGGATAACAA CATATTCCCC         120

AAACAATACC CAATTATAAA CTTTACCACA GCGGGTGCCA CTGTGCAAAG CTACACAAAC         180

TTTATCAGAG CTGTTCGCGG TCGTTTAACA ACTGGAGCTG ATGTGAGACA TGATATACCA         240

GTGTTGCCAA ACAGAGTTGG TTTGCCTATA AACCAACGGT TTATTTTAGT TGAACTCTCA         300

AATCATGCAG AGCTTTCTGT TACATTAGCG CTGGATGTCA CCAATGCATA TGTGGTCGGC         360

TACCGTGCTG GAAATAGCGC ATATTTCTTT CATCCTGACA ATCAGGAAGA TGCAGAAGCA         420

ATCACTCATC TTTTCACTGA TGTTCAAAAT CGATATACAT TCGCCTTTGG TGGTAATTAT         480

GATAGACTTG AACAACTTGC TGGTAATCTG AGAGAAAATA TCGAGTTGGG AAATGGTCCA         540

CTAGAGGAGG CTATCTCAGC GCTTTATTAT TACAGTACTG GTGGCACTCA GCTTCCAACT         600

CTGGCTCGTT CCTTTATAAT TTGCATCCAA ATGATTTCAG AAGCAGCAAG ATTCCAATAT         660

ATTGAGGGAG AAATGCGCAC GAGAATTAGG TACAACCGGA GATCTGCACC AGATCCTAGC         720

GTAATTACAC TTGAGAATAG TTGGGGGAGA CTTTCCACTG CAATTCAAGA GTCTAACCAA         780

GGAGCCTTTG CTAGTCCAAT TCAACTGCAA AGACGTAATG GTTCCAAATT CAGTGTGTAC         840

GATGTGAGTA TATTAATCCC TATCATAGCT CTCATGGTGT ATAGATGCGC ACCTCCACCA         900

TCGTCACAGT TTTCTGCGCC TCAAGTGCTA CCGGTGATGC ATCCTAATGC TGATGTTTGT         960

ATGGATCCTG AGCCCATAGT GCGTATCGTA GGTCGAAATG GTCTATGTGT TGATGTTAGG         1020

GATGGAAGAT TCCACAACGG AAACGCAATA CAGTTGTGGC CATGCAAGTC TAATACAGAT         1080

GCAAATCAGC TCTGGACTTT GAAAAGAGAC AATACTATTC GATCTAATGG AAAGTGTTTA         1140

ACTACTTACG GGTACAGTCC GGGAGTCTAT GTGATGATCT ATGATTGCAA TACTGCTGCA         1200

ACTGATGCCA CCCGCTGGCA AATATGGGAT AATGGAACCA TCATAAATCC CAGATCTAGT         1260

CTAGTTTTAG CAGCGACATC AGGGAACAGT GGTACCACAC TTACAGTGCA AACCAACATT         1320

```
TATGCCGTTA GTCAAGGTTG GCTTCCTACT AATAATACAC AACCTTTTGT TACAACCATT    1380

GTTGGGCTAT ATGGTCTGTG CTTGCAAGCA AATAGTGGAC AAGTATGGAT AGAGGACTGT    1440

AGCAGTGAAA AGGCTGAACA ACAGTGGGCT CTTTATGCAG ATGGTTCAAT ACGTCCTCAG    1500

CAAAACCGAG ATAATTGCCT TACAAGTGAT TCTAATATAC GGGAAACAGT TGTTAAGATC    1560

CTCTCTTGTG GCCCTGCATC CTCTGGCCAA CGATGGATGT TCAAGAATGA TGGAACCATT    1620

TTAAATTTGT ATAGTGGATT GGTGTTAGAT GTGAGGCGAT CGGATCCGAG CCTTAAACAA    1680

ATCATTCTTT ACCCTCTCCA TGGTGACCCA AACCAAATAT GGTTACCATT ATTTTGATAG    1740

ACAGATTACT CTCTTGCAGT GTGTGTGTCC TGCCATGAAA ATAGATGGCT TAAATAAAAA    1800

GGACATTGTA AATTTTGTAA CTGAAAGGAC AGCAAGTTAT ATCGAATTCC TGCAG         1855

(2) INFORMATION FOR SEQ ID NO:34:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:34:

TCTTTGCTTA TAAGGCCAGT GGTGCCAAAT TTTAAT                                36

(2) INFORMATION FOR SEQ ID NO:35:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:35:

AGAAACGAAT ATTCCGGTCA CCACGGTTTA AAATTA                                36

(2) INFORMATION FOR SEQ ID NO:36:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:36:

GTGGTGCAAC CTAAGAATGC TGATGTTTGT                                        30

(2) INFORMATION FOR SEQ ID NO:37:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:37:

AGCAGTGTCA AAAGATTCTG ATTTCACGAT                                        30
```

(2) INFORMATION FOR SEQ ID NO:38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
TCTAAGACTA AAGTGCTAGT GGTGCAACCT AAGAAT                                   36
```

(2) INFORMATION FOR SEQ ID NO:39:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
AGATTCTGAT TTCACGATCA CCACGTTGGA TTCTTA                                   36
```

(2) INFORMATION FOR SEQ ID NO:40:

(i) SEQUENCE CHARACTERISTICS:
        (A) LENGTH: 1855 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
GAATTCATGA AACCGGGAGG AAATACTATT GTAATATGGA TGTATGCAGT GGCAACATGG         60
CTTTGTTTTG GATCCACCTC AGGGTGGTCT TCACATTAG AGGATAACAA CATATTCCCC         120
AAACAATACC CAATTATAAA CTTTACCACA GCGGGTGCCA CTGTGCAAAG CTACACAAAC        180
TTTATCAGAG CTGTTCGCGG TCGTTTAACA ACTGGAGCTG ATGTGAGACA TGATATACCA        240
GTGTTGCCAA ACAGAGTTGG TTTGCCTATA AACCAACGGT TTATTTTAGT TGAACTCTCA        300
AATCATGCAG AGCTTTCTGT TACATTAGCG CTGGATGTCA CCAATGCATA TGTGGTCGGC        360
TACCGTGCTG GAAATAGCGC ATATTTCTTT CATCCTGACA ATCAGGAAGA TGCAGAAGCA        420
ATCACTCATC TTTTCACTGA TGTTCAAAAT CGATATACAT TCGCCTTTGG TGGTAATTAT        480
GATAGACTTG AACAACTTGC TGGTAATCTG AGAGAAAATA TCGAGTTGGG AAATGGTCCA        540
CTAGAGGAGG CTATCTCAGC GCTTTATTAT TACAGTACTG GTGGCACTCA GCTTCCAACT        600
CTGGCTCGTT CCTTTATAAT TTGCATCCAA ATGATTTCAG AAGCAGCAAG ATTCCAATAT        660
ATTGAGGGAG AAATGCGCAC GAGAATTAGG TACAACCGGA GATCTGCACC AGATCCTAGC        720
GTAATTACAC TTGAGAATAG TTGGGGGAGA CTTTCCACTG CAATTCAAGA GTCTAACCAA        780
GGAGCCTTTG CTAGTCCAAT TCAACTGCAA AGACGTAATG GTTCCAAATT CAGTGTGTAC        840
GATGTGAGTA TATTAATCCC TATCATAGCT CTCATGGTGT ATAGATGCGC ACCTCCACCA        900
TCGTCACAGT TTTCTAAGAC TAAAGTGCTA GTGGTGCAAC CTAAGAATGC TGATGTTTGT        960
ATGGATCCTG AGCCCATAGT GCGTATCGTA GGTCGAAATG GTCTATGTGT TGATGTTAGG       1020
GATGGAAGAT TCCACAACGG AAACGCAATA CAGTTGTGGC CATGCAAGTC TAATACAGAT       1080
```

-continued

```
GCAAATCAGC TCTGGACTTT GAAAAGAGAC AATACTATTC GATCTAATGG AAAGTGTTTA      1140

ACTACTTACG GGTACAGTCC GGGAGTCTAT GTGATGATCT ATGATTGCAA TACTGCTGCA      1200

ACTGATGCCA CCCGCTGGCA AATATGGGAT AATGGAACCA TCATAAATCC CAGATCTAGT      1260

CTAGTTTTAG CAGCGACATC AGGGAACAGT GGTACCACAC TTACAGTGCA AACCAACATT      1320

TATGCCGTTA GTCAAGGTTG GCTTCCTACT AATAATACAC AACCTTTTGT TACAACCATT      1380

GTTGGGCTAT ATGGTCTGTG CTTGCAAGCA AATAGTGGAC AAGTATGGAT AGAGGACTGT      1440

AGCAGTGAAA AGGCTGAACA ACAGTGGGCT CTTTATGCAG ATGGTTCAAT ACGTCCTCAG      1500

CAAAACCGAG ATAATTGCCT TACAAGTGAT TCTAATATAC GGGAAACAGT TGTTAAGATC      1560

CTCTCTTGTG GCCCTGCATC CTCTGGCCAA CGATGGATGT TCAAGAATGA TGGAACCATT      1620

TTAAATTTGT ATAGTGGATT GGTGTTAGAT GTGAGGCGAT CGGATCCGAG CCTTAAACAA      1680

ATCATTCTTT ACCCTCTCCA TGGTGACCCA AACCAAATAT GGTTACCATT ATTTTGATAG      1740

ACAGATTACT CTCTTGCAGT GTGTGTGTCC TGCCATGAAA ATAGATGGCT TAAATAAAAA      1800

GGACATTGTA AATTTTGTAA CTGAAAGGAC AGCAAGTTAT ATCGAATTCC TGCAG          1855
```

(2) INFORMATION FOR SEQ ID NO:41:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
TCTTTGCTTA TAAGGCCAGT GGTGCCAAAT TTTAAT                                36
```

(2) INFORMATION FOR SEQ ID NO:42:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
AGAAACGAAT ATTCCGGTCA CCACGGTTTA AAATTA                                36
```

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
GTGGTGCAAC CTAGGAATGC TGATGTTTGT                                       30
```

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

AGCAGTGTCA AAAGATTCTG ATTTCACGAT                                           30

(2) INFORMATION FOR SEQ ID NO:45:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

TCTAAGACTA AAGTGCTAGT GGTGCAACCT AGGAAT                                    36

(2) INFORMATION FOR SEQ ID NO:46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

AGATTCTGAT TTCACGATCA CCACGTTGGA TCCTTA                                    36

(2) INFORMATION FOR SEQ ID NO:47:

(i) SEQUENCE CHARACTERISTICS:
        (A) LENGTH: 1855 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GAATTCATGA AACCGGGAGG AAATACTATT GTAATATGGA TGTATGCAGT GGCAACATGG           60

CTTTGTTTTG GATCCACCTC AGGGTGGTCT TTCACATTAG AGGATAACAA CATATTCCCC          120

AAACAATACC CAATTATAAA CTTTACCACA GCGGGTGCCA CTGTGCAAAG CTACACAAAC          180

TTTATCAGAG CTGTTCGCGG TCGTTTAACA ACTGGAGCTG ATGTGAGACA TGATATACCA          240

GTGTTGCCAA ACAGAGTTGG TTTGCCTATA AACCAACGGT TTATTTTAGT TGAACTCTCA          300

AATCATGCAG AGCTTTCTGT TACATTAGCG CTGGATGTCA CCAATGCATA TGTGGTCGGC          360

TACCGTGCTG GAAATAGCGC ATATTTCTTT CATCCTGACA ATCAGGAAGA TGCAGAAGCA          420

ATCACTCATC TTTTCACTGA TGTTCAAAAT CGATATACAT TCGCCTTTGG TGGTAATTAT          480

GATAGACTTG AACAACTTGC TGGTAATCTG AGAGAAAATA TCGAGTTGGG AAATGGTCCA          540

CTAGAGGAGG CTATCTCAGC GCTTTATTAT TACAGTACTG GTGGCACTCA GCTTCCAACT          600

CTGGCTCGTT CCTTTATAAT TTGCATCCAA ATGATTTCAG AAGCAGCAAG ATTCCAATAT          660

ATTGAGGGAG AAATGCGCAC GAGAATTAGG TACAACCGGA GATCTGCACC AGATCCTAGC          720

GTAATTACAC TTGAGAATAG TTGGGGGAGA CTTTCCACTG CAATTCAAGA GTCTAACCAA          780

GGAGCCTTTG CTAGTCCAAT TCAACTGCAA AGACGTAATG GTTCCAAATT CAGTGTGTAC          840

GATGTGAGTA TATTAATCCC TATCATAGCT CTCATGGTGT ATAGATGCGC ACCTCCACCA          900

```
TCGTCACAGT TTTCTAAGAC TAAAGTGCTA GTGGTGCAAC CTAGGAATGC TGATGTTTGT      960

ATGGATCCTG AGCCCATAGT GCGTATCGTA GGTCGAAATG GTCTATGTGT TGATGTTAGG     1020

GATGGAAGAT TCCACAACGG AAACGCAATA CAGTTGTGGC CATGCAAGTC TAATACAGAT     1080

GCAAATCAGC TCTGGACTTT GAAAAGAGAC AATACTATTC GATCTAATGG AAAGTGTTTA     1140

ACTACTTACG GGTACAGTCC GGGAGTCTAT GTGATGATCT ATGATTGCAA TACTGCTGCA     1200

ACTGATGCCA CCCGCTGGCA AATATGGGAT AATGGAACCA TCATAAATCC CAGATCTAGT     1260

CTAGTTTTAG CAGCGACATC AGGGAACAGT GGTACCACAC TTACAGTGCA AACCAACATT     1320

TATGCCGTTA GTCAAGGTTG GCTTCCTACT AATAATACAC AACCTTTTGT TACAACCATT     1380

GTTGGGCTAT ATGGTCTGTG CTTGCAAGCA AATAGTGGAC AAGTATGGAT AGAGGACTGT     1440

AGCAGTGAAA AGGCTGAACA ACAGTGGGCT CTTTATGCAG ATGGTTCAAT ACGTCCTCAG     1500

CAAAACCGAG ATAATTGCCT TACAAGTGAT TCTAATATAC GGGAAACAGT TGTTAAGATC     1560

CTCTCTTGTG GCCCTGCATC CTCTGGCCAA CGATGGATGT TCAAGAATGA TGGAACCATT     1620

TTAAATTTGT ATAGTGGATT GGTGTTAGAT GTGAGGCGAT CGGATCCGAG CCTTAAACAA     1680

ATCATTCTTT ACCCTCTCCA TGGTGACCCA AACCAAATAT GGTTACCATT ATTTTGATAG     1740

ACAGATTACT CTCTTGCAGT GTGTGTGTCC TGCCATGAAA ATAGATGGCT TAAATAAAAA     1800

GGACATTGTA AATTTTGTAA CTGAAAGGAC AGCAAGTTAT ATCGAATTCC TGCAG         1855

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

TCTTTGCTTA TAAGGCCAGT GGTGCCAAAT TTTAAT                                 36

(2) INFORMATION FOR SEQ ID NO:49:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AGAAACGAAT ATTCCGGTCA CCACGGTTTA AAATTA                                 36

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

CCGATACTAC ATCCTAATGC TGATGTTTGT                                        30
```

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
AGCAGTGTCA AAAGATGCTG AGTTACAAAG                                30
```

(2) INFORMATION FOR SEQ ID NO:52:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
TCTACGACTC AATGTTTCCC GATACTACAT CCTAAT                         36
```

(2) INFORMATION FOR SEQ ID NO:53:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
AGATGCTGAG TTACAAAGGG CTATGATGTA GGATTA                         36
```

(2) INFORMATION FOR SEQ ID NO:54:

(i) SEQUENCE CHARACTERISTICS:
        (A) LENGTH: 1855 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
GAATTCATGA AACCGGGAGG AAATACTATT GTAATATGGA TGTATGCAGT GGCAACATGG   60
CTTTGTTTTG GATCCACCTC AGGGTGGTCT TCACATTAG AGGATAACAA CATATTCCCC   120
AAACAATACC CAATTATAAA CTTTACCACA GCGGGTGCCA CTGTGCAAAG CTACACAAAC   180
TTTATCAGAG CTGTTCGCGG TCGTTTAACA ACTGGAGCTG ATGTGAGACA TGATATACCA   240
GTGTTGCCAA ACAGAGTTGG TTTGCCTATA AACCAACGGT TTATTTTAGT TGAACTCTCA   300
AATCATGCAG AGCTTTCTGT TACATTAGCG CTGGATGTCA CCAATGCATA TGTGGTCGGC   360
TACCGTGCTG GAAATAGCGC ATATTTCTTT CATCCTGACA ATCAGGAAGA TGCAGAAGCA   420
ATCACTCATC TTTTCACTGA TGTTCAAAAT CGATATACAT TCGCCTTTGG TGGTAATTAT   480
GATAGACTTG AACAACTTGC TGGTAATCTG AGAGAAAATA TCGAGTTGGG AAATGGTCCA   540
CTAGAGGAGG CTATCTCAGC GCTTTATTAT TACAGTACTG GTGGCACTCA GCTTCCAACT   600
CTGGCTCGTT CCTTTATAAT TTGCATCCAA ATGATTTCAG AAGCAGCAAG ATTCCAATAT   660
```

```
ATTGAGGGAG AAATGCGCAC GAGAATTAGG TACAACCGGA GATCTGCACC AGATCCTAGC    720

GTAATTACAC TTGAGAATAG TTGGGGGAGA CTTTCCACTG CAATTCAAGA GTCTAACCAA    780

GGAGCCTTTG CTAGTCCAAT TCAACTGCAA AGACGTAATG GTTCCAAATT CAGTGTGTAC    840

GATGTGAGTA TATTAATCCC TATCATAGCT CTCATGGTGT ATAGATGCGC ACCTCCACCA    900

TCGTCACAGT TTTCTACGAC TCAATGTTTC CCGATACTAC ATCCTAATGC TGATGTTTGT    960

ATGGATCCTG AGCCCATAGT GCGTATCGTA GGTCGAAATG GTCTATGTGT TGATGTTAGG   1020

GATGGAAGAT TCCACAACGG AAACGCAATA CAGTTGTGGC CATGCAAGTC TAATACAGAT   1080

GCAAATCAGC TCTGGACTTT GAAAAGAGAC AATACTATTC GATCTAATGG AAAGTGTTTA   1140

ACTACTTACG GGTACAGTCC GGGAGTCTAT GTGATGATCT ATGATTGCAA TACTGCTGCA   1200

ACTGATGCCA CCCGCTGGCA AATATGGGAT AATGGAACCA TCATAAATCC CAGATCTAGT   1260

CTAGTTTTAG CAGCGACATC AGGGAACAGT GGTACCACAC TTACAGTGCA AACCAACATT   1320

TATGCCGTTA GTCAAGGTTG GCTTCCTACT AATAATACAC AACCTTTTGT TACAACCATT   1380

GTTGGGCTAT ATGGTCTGTG CTTGCAAGCA AATAGTGGAC AAGTATGGAT AGAGGACTGT   1440

AGCAGTGAAA AGGCTGAACA ACAGTGGGCT CTTTATGCAG ATGGTTCAAT ACGTCCTCAG   1500

CAAAACCGAG ATAATTGCCT TACAAGTGAT TCTAATATAC GGGAAACAGT TGTTAAGATC   1560

CTCTCTTGTG GCCCTGCATC CTCTGGCCAA CGATGGATGT TCAAGAATGA TGGAACCATT   1620

TTAAATTTGT ATAGTGGATT GGTGTTAGAT GTGAGGCGAT CGGATCCGAG CCTTAAACAA   1680

ATCATTCTTT ACCCTCTCCA TGGTGACCCA AACCAAATAT GGTTACCATT ATTTTGATAG   1740

ACAGATTACT CTCTTGCAGT GTGTGTGTCC TGCCATGAAA ATAGATGGCT TAAATAAAAA   1800

GGACATTGTA AATTTTGTAA CTGAAAGGAC AGCAAGTTAT ATCGAATTCC TGCAG        1855
```

(2) INFORMATION FOR SEQ ID NO:55:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

Ser Ala Pro Gln Val Leu Pro Val Met His Pro Asn
1               5                   10

(2) INFORMATION FOR SEQ ID NO:56:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

Ser Lys Thr Lys Val Leu Val Val Gln Pro Lys Asn
1               5                   10

(2) INFORMATION FOR SEQ ID NO:57:

(i) SEQUENCE CHARACTERISTICS:
        (A) LENGTH: 12 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:57:

Ser Lys Thr Lys Val Leu Val Val Gln Pro Arg Asn
1               5                   10

(2) INFORMATION FOR SEQ ID NO:58:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:58:

Ser Thr Thr Gln Cys Phe Pro Ile Leu His Pro Asn
1               5                   10

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

AATTAACCCT CACTAAAGGG                                                   20

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

GTAATACGAC TCACTATAGG GC                                                22

(2) INFORMATION FOR SEQ ID NO:61:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

GGAGATGAAA CCGGGAGGAA ATACTATTGT AAT                                    33

(2) INFORMATION FOR SEQ ID NO:62:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

GCGGAATTCC GGGAGGAAAT ACTATTGTAA T                           31

(2) INFORMATION FOR SEQ ID NO:63:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

ACGGTTTATT TTAGTTGA                                          18

(2) INFORMATION FOR SEQ ID NO:64:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

ACTTGCTGGT AATCTGAG                                          18

(2) INFORMATION FOR SEQ ID NO:65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

AGAATAGTTG GGGGAGAC                                          18

(2) INFORMATION FOR SEQ ID NO:66:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

AATGCTGATG TTTGTATG                                          18

(2) INFORMATION FOR SEQ ID NO:67:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

-continued

```
CGGGAGTCTA TGTGATGA                                              18

(2) INFORMATION FOR SEQ ID NO:68:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

GCAAATAGTG GACAAGTA                                              18

(2) INFORMATION FOR SEQ ID NO:69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

GGATTGGTGT TAGATGTG                                              18

(2) INFORMATION FOR SEQ ID NO:70:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

ATAACTTGCT GTCCTTTCA                                             19

(2) INFORMATION FOR SEQ ID NO:71:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

CGCTCTAGAT AACTTGCTGT CCTTTCA                                    27
```

TABLE OF CONCORDANCE

| SEQ. ID. NOS | LOCATION IN APPLICATION |
|---|---|
| SEQ. ID. NOS. 1–6 | Page 6, line 16; page 25, line 20; and Figure 1B |
| SEQ. ID. NOS. 7–12 | Page 6, line 18; page 9; line 10; page 25, line 21; and Figure 2B |
| SEQ. ID. NOS 13–18 | Page 6, line 20; page 25, line 23; page 12, line 3; page 9, line 10 |
| SEQ. ID. NOS. 19–22 | Page 6, line 21; page 9, line 6; page 25, line 17; Figure 4 |
| SEQ. ID. NO. 23 | Page 4, line 25; page 6, line 29; page 11, line 27; Page 41, line 18; Figure 8 |
| SEQ. ID. NO. 24 | Page 4, line 25; page 6, line 30; page 11, line 27; page 41, line 18; Figure 9 |
| SEQ. ID. NO. 25 | Page 4, line 25; page 6, line 31; page 11, line 28, page 41, line 18; Figure 10 |

-continued

TABLE OF CONCORDANCE

| SEQ. ID. NOS | LOCATION IN APPLICATION |
|---|---|
| SEQ. ID. NO. 26 | Page 5, line 1; page 6, line 32; page 26, line 10; page 41, line 37 |
| SEQ. ID NOS. 27–32 | Page 7, line 4; page 12, line 4; Figure 16B |
| SEQ. ID. NO. 33 | Page 7, line 8; Figure 16D |
| SEQ. ID. NOS. 34–39 | Page 7, line 12; Page 12, line 4; and Figure 17B |
| SEQ. ID. NO. 40 | Page 7, line 16; and Figure 17D |
| SEQ. ID. NOS. 41–46 | Page 7, line 20; Figure 18B |
| SEQ. ID. NO. 47 | Page 7, line 24; Figure 18D |
| SEQ. ID. NOS. 48–53 | Page 7, line 28; page 12, line 4; Figure 19B |
| SEQ. ID. NO. 54 | Page 7, line 32; Figure 19D |
| SEQ. ID. NOS. 55–58 | Page 7, line 34; page 33, line 31; Figure 20 |
| SEQ. ID. NO. 59 | Page 25, line 9 |
| SEQ. ID. NO. 60 | Page 25, line 10 |
| SEQ. ID. NOS. 61–71 | Table 1 |

What is claimed is:

1. A purified and isolated nucleic acid having a nucleotide sequence encoding an A chain of a ricin-like toxin, a B chain of a ricin-like toxin and a heterologous linker amino acid sequence, linking the A and B chains, wherein the linker sequence contains a cleavage recognition site for a retroviral protease.

2. The nucleic acid of claim 1 wherein the A chain is ricin A chain.

3. The nucleic acid of claim 1 wherein the B chain is ricin B chain.

4. The nucleic acid of claim 1 wherein the cleavage recognition site is the cleavage recognition site for an HIV protease.

5. The nucleic acid of claim 1 wherein the linker amino acid sequence comprises VSQNYPIVQNFN (SEQ. ID. NO:20); SKARVLAEAMSN (SEQ. ID. NO:21); or SIRKILFLDGIN (SEQ. ID. NO:22).

6. The nucleic acid of claim 1 having the nucleotide sequence shown in FIG. 8, FIG. 9 or FIG. 10.

7. The nucleic acid of claim 1 wherein the cleavage recognition site is the cleavage recognition site for a human T-cell leukemia virus (HTLV) protease.

8. The nucleic acid of claim 7 wherein the linker amino acid sequence comprises SAPQVLPVMHPN (SEQ. ID. NO:55); SKTKVLVVQPKN (SEQ. ID. NO:56); SKTVLVQPRN (SEQ. ID. NO:57, or STTQCFPILHPN (SEQ. ID. NO:58).

9. A plasmid incorporating the nucleic acid of claim 1.

10. A plasmid as claimed in claim 7 having the restriction map as shown in FIGS. 1A, 2A, 3A, 16A, 17A or 18A.

11. A baculovirus transfer vector incorporating the nucleic acid of claim 1.

12. A baculovirus transfer vector as claimed in claim 11 having the restriction map as shown in FIGS. 5, 6, 7, 16C, 17C, or 18C.

13. A baculovirus transfer vector as claimed in claim 11 having the DNA sequence as shown in FIG. 11.

14. A recombinant protein comprising an A chain of a ricin-like toxin, a B chain of a ricin-like toxin and a heterologous linker amino acid sequence, linking the A and B chains, wherein the linker sequence contains a cleavage recognition site for a retroviral protease.

15. The recombinant protein of claim 14 wherein the A chain is ricin A chain.

16. The recombinant protein of claim 14 wherein the B chain is ricin B chain.

17. The recombinant protein of claim 14 wherein the cleavage recognition site is the cleavage recognition site for an HIV protease.

18. The recombinant protein of claim 14 wherein the linker amino acid sequence comprises VSQNYPIVQNFN (SEQ.ID.NO:20); SKARVLAEAMSN (SEQ.ID.NO:21); or SIRKILFLDGIN (SEQ.ID.NO;22).

19. A recombinant protein comprising an A chain of a ricin-like toxin, a B chain of a ricin-like toxin and a heterologous linker amino acid sequence, linking the A and B chains, wherein the linker sequence contains a cleavage recognition site for a HTLV protease.

20. The recombinant protein of claim 19 wherein the linker amino acid sequence comprises SAPQVLPVMHPN (SEQ.ID.NO:55); SKTKVLWQPKN (SEQ.ID.NO:56); SKTKVLVVQPRN (SEQ.ID.NO:57) or STTQCFPILHPN (SEQ.ID.NO:58).

21. A method of inhibiting or destroying mammalian cells infected with a retrovirus having a protease, comprising the steps of preparing a recombinant protein of claim 14 wherein the linker sequence contains a cleavage recognition site for the retrovirus protease and administering the fusion protein to the cells.

22. A method as claimed in claim 21, wherein the retrovirus is HIV.

23. A method as claimed in claim 21 wherein the mammalian cells are human cells.

24. A method of treating a mammal infected with HIV, comprising the steps of preparing a recombinant protein of claim 14 and administering the protein to the mammal.

25. A process for preparing a pharmaceutical for treating a mammal infected with a retrovirus having a protease comprising the steps of preparing a purified and isolated nucleic acid having a nucleotide sequence encoding an A chain of a ricin-like toxin, a B chain of a ricin-like toxin and a heterologous linker amino acid sequence, linking the A and B chains, wherein the linker sequence contains a cleavage recognition site for the protease; introducing the nucleic acid into a host cell; expressing the nucleic acid in the host cell to obtain a recombinant protein comprising an A chain of a ricin-like toxin, a B chain of a ricin-like toxin and a linker amino acid sequence, linking the A and B chains wherein the linker sequence contains the cleavage recognition site for the protease, and suspending the protein in a pharmaceutically acceptable carrier, diluent or excipient.

26. A process for preparing a pharmaceutical for treating a mammal infected with a retrovirus having a protease comprising the steps of identifying a cleavage recognition site for the protease; preparing a recombinant protein comprising an A chain of a ricin-like toxin, a B chain of a ricin-like toxin and a heterologous linker amino acid sequence, linking the A and B chains, wherein the linker sequence contains the cleavage recognition site for the protease and suspending the protein in a pharmaceutically acceptable carrier, diluent or excipient.

27. A pharmaceutical composition for treating a retroviral infection in a mammal comprising the recombinant protein of claim 14 and a pharmaceutically acceptable carrier, diluent or excipient.

28. A pharmaceutical composition for treating HIV infection in a mammal comprising the recombinant protein of claim 14 and a pharmaceutically acceptable carrier, diluent or excipient.

* * * * *

UNITED STATES PATENT AND TRADEMARK OFFICE
CERTIFICATE OF CORRECTION

PATENT NO. : 6,333,303 B1
DATED : June 20, 2002
INVENTOR(S) : Thor Borgford

It is certified that error appears in the above-identified patent and that said Letters Patent is hereby corrected as shown below:

Column 79,
Line 44, replace "SKTVLVVQPRN" by -- SKTKVLVVQPRN --;

Column 80,
Line 15, replace "SKTKVLWQPKN" by -- SKTKVLVVQPKN --.

Signed and Sealed this

Ninth Day of July, 2002

Attest:

Attesting Officer

JAMES E. ROGAN
Director of the United States Patent and Trademark Office